US011248240B2

(12) United States Patent
Bastianelli et al.

(10) Patent No.: US 11,248,240 B2
(45) Date of Patent: Feb. 15, 2022

(54) METHOD FOR INDUCING TARGETED MEIOTIC RECOMBINATIONS

(71) Applicants: MEIOGENIX, Paris (FR); INSTITUT CURIE, Paris (FR); CENTRE NATIONAL DE LA RECHERCHE SCIENTIFIQUE, Paris (FR); SORBONNE UNIVERSITE, Paris (FR)

(72) Inventors: Giacomo Bastianelli, Paris (FR); Alexandre Serero, Colombes (FR); Alain Nicolas, Paris (FR)

(73) Assignees: MEIOGENIX, Paris (FR); INSTITUT CURIE, Paris (FR); CENTRE NATIONAL DE LA RECHERCHE SCIENTIFIQUE, Paris (FR); SORBONNE UNIVERSITE, Paris (FR)

( * ) Notice: Subject to any disclaimer, the term of this patent is extended or adjusted under 35 U.S.C. 154(b) by 0 days.

(21) Appl. No.: 15/547,084

(22) PCT Filed: Jan. 29, 2016

(86) PCT No.: PCT/EP2016/052000
§ 371 (c)(1),
(2) Date: Jul. 28, 2017

(87) PCT Pub. No.: WO2016/120480
PCT Pub. Date: Aug. 4, 2016

(65) Prior Publication Data
US 2018/0023091 A1 Jan. 25, 2018

(30) Foreign Application Priority Data

Jan. 29, 2015 (FR) ...................... 1550707
Jun. 22, 2015 (FR) ...................... 1555725

(51) Int. Cl.
| | | |
|---|---|---|
| *C12N 15/90* | (2006.01) | |
| *C12N 9/22* | (2006.01) | |
| *C12N 9/90* | (2006.01) | |
| *C12N 15/11* | (2006.01) | |
| *C12N 15/65* | (2006.01) | |
| *C12N 15/81* | (2006.01) | |
| *C12N 15/82* | (2006.01) | |

(52) U.S. Cl.
CPC ............ *C12N 15/905* (2013.01); *C12N 9/22* (2013.01); *C12N 9/90* (2013.01); *C12N 15/11* (2013.01); *C12N 15/65* (2013.01); *C12N 15/81* (2013.01); *C12N 15/8213* (2013.01); *C12N 15/902* (2013.01); *C12Y 599/01003* (2013.01); *C07K 2319/09* (2013.01); *C12N 2310/20* (2017.05); *C12N 2800/22* (2013.01)

(58) Field of Classification Search
CPC .. C12N 2310/20; C12N 15/8213; C12N 9/22; C12N 15/82; C12N 15/8201; C12N 15/823–15/8233; C12N 15/81; C12N 15/905; C12N 9/90; C12Y 599/01003; C07K 2319/09
See application file for complete search history.

(56) References Cited

U.S. PATENT DOCUMENTS

| | | | | |
|---|---|---|---|---|
| 7,273,758 B2 * | 9/2007 | Nicolas | ................ | C07K 14/395 435/463 |
| 7,279,334 B2 * | 10/2007 | Nicolas | ................ | C07K 14/415 435/419 |
| 2004/0033494 A1 | 2/2004 | Nicolas et al. | | |
| 2015/0307868 A1 * | 10/2015 | Nicolas | ..................... | C12N 1/16 506/2 |
| 2016/0017393 A1 * | 1/2016 | Jacobson | ................ | C12N 9/22 435/91.53 |

FOREIGN PATENT DOCUMENTS

| | | | | | |
|---|---|---|---|---|---|
| FR | 2998898 A1 * | 6/2014 | ............... | C12N 1/16 | |
| WO | WO-2014083142 A1 * | 6/2014 | ............... | C12N 1/16 | |
| WO | WO-2014099744 A1 * | 6/2014 | ............. | C12N 15/10 | |
| WO | WO 2014/104878 | 7/2014 | | | |
| WO | WO-2016054326 A1 * | 4/2016 | ........... | C12N 15/102 | |

OTHER PUBLICATIONS

Li et al. Double-stranded DNA breaks and gene functions in recombination in meiosis. Cell Research, vol. 16, pp. 402-412, 2006. (Year: 2006).*
Bassett et al. CRISPR/Cas9 and genome editing in *Drosophila*. Journal of Genetics and Genomics, vol. 41, pp. 7-19, 2014, published online Dec. 18, 2013. (Year: 2013).*
Liti et al. Advances in quantative trait analysis in yeast. PLoS Genetics, vol. 8, No. 8, e1002912, Aug. 16, 2012, printed as p. 1-7. (Year: 2012).*
Machine translation of FR2998898, printed as pp. 1-27 on Apr. 25, 2019. (Year: 2019).*
Bowles et al. Retinoid signaling determines germ cell fate in mice. Science, vol. 312, No. 5773, pp. 596-600, 2006. (Year: 2006).*
Milo et al. "What are the concentrations of different ions in cells?" http://book.bionumbers.org/what-are-the-concentrations-of-different-ions-in-cells, printed as pp. 1/5-5/5 on Dec. 20, 2016 from the online version of Cell Biology by the Numbers, published Dec. 7, 2015. (Year: 2015).*
Scott et al. Targeted genome regulation and modification using transcription activator-like effectors. vol. 281, No. 20, pp. 4583-4597, Sep. 6, 2014. (Year: 2014).*

(Continued)

*Primary Examiner* — Jennifer Dunston
(74) *Attorney, Agent, or Firm* — Saliwanchik, Lloyd & Eisenschenk

(57) ABSTRACT

The present invention relates to a fusion protein comprising a Cas9 domain and a Spo11 domain, as well as the use of this protein to induce targeted meiotic recombinations in a eukaryotic cell.

7 Claims, 12 Drawing Sheets
Specification includes a Sequence Listing.

(56) References Cited

OTHER PUBLICATIONS

Carroll, D. A CRISPR approach to gene targeting. Molecular Therapy, vol. 20, No. 9, pp. 1658-1660, Sep. 2012. (Year: 2012).*
Nishimasu et al. Crystal structure of Cas9 in complex with guide RNA and target DNA. Cell, vol. 156, pp. 935-949, Feb. 27, 2014. (Year: 2014).*
Ding et al. Recent advances in genome editing using CRISPR/Cas9. Frontiers in Plant Science, vol. 7, 703, May 24, 2016, printed as pp. 1-12. (Year: 2016).*
Hunter et al. Synaptonemal complexities and commonalities. Molecular Cell, vol. 12, pp. 533-539, Sep. 2003. (Year: 2003 ).*
Lam et al. Mechanism and regulation of meiotic recombination initiation. Cold Spring Harbor Perspectives in Biology, vol. 7, No. 1, a016634, Oct. 2014, printed as pp. 1-25. (Year: 2014).*
Baudat et al. SPO11: une activite de coupure de l'ADN indispensable a la meiose. Medicine/Sciences, vol. 20, pp. 213-218, 2004, including pp. 1/7-7/7 of machine translation. (Year: 2004).*
Sun et al. Reconstitution of gametogenesis in vitro: Meiosis is the biggest obstacle. Journal of Genetics and Genomics, vol. 41, pp. 87-95, Feb. 22, 2014. (Year: 2014).*
Rönspies et al. CRISPR-Cas-mediated chromosome engineering for crop improvement and synthetic biology. Nature Plants, DOI: 10.1038/s41477-021-00910-4, online ahead of print, May 6, 2021, printed as pp. 1/8-8/8; paragraph bridging pp. 3/8-4/8. (Year: 2021).*
Yelina et al. CRISPR targeting of Meiotic-Topoisomerase VIB-dCas9 to a recombination hotspot is insufficient to increase crossover frequency in *Arabidopsis*. Preprint at bioRxiv https://doi.org/10.1101/2021.02.01.429210, Feb. 2, 2021, printed as pp. 1/42-42/42. (Year: 2021).*
Dicarlo, J. E et al. "Genome engineering in *Saccharomyces cerevisiae* using CRISPR-Cas systems" *Nucleic Acids Research*, Mar. 4, 2013, pp. 4336-4343, vol. 41, No. 7.
Jinek, M. et al. "A Programmable Dual-RNA-Guided DNA Endonuclease in Adaptive Bacterial Immunity" *Science*, Jun. 28, 2012, pp. 1-37, Supplementary Materials Only.
Lam, I. et al. "Mechanism and regulation of meiotic recombination initiation" *Cold Spring Harbor Perspectives in Biology*, Nov. 7, 2015, pp. 1-34, vol. 7, No. 1.
Peciña, A. et al. "Targeted Stimulation of Meiotic Recombination" *Cell*, Oct. 18, 2002, pp. 173-184, vol. 111.
Written Opinion in International Application No. PCT/EP2016/052000, dated Mar. 17, 2016, pp. 1-6.
Morrill, G. A. et al. "Role of Calcium in Regulating Intracellular pH Following the Stepwise Release of the Metabolic Blocks at First-Meiotic Prophase and Second-Meiotic Metaphase in Amphibian Oocytes" *Biochimica et Biophysica Acta*, 1984, pp. 107-117, vol. 804.
MacGregor, I. A. et al. "Large-scale chromatin organisation in interphase, mitosis and meiosis" *Biochemical Journal*, 2019, pp. 2141-2156, vol. 476.
Kasama, T. et al. "Spo5/Mug12, a Putative Meiosis-Specific RNA-Binding Protein, Is Essential for Meiotic Progression and Forms Mei2 Dot-Like Nuclear Foci" *Eukaryotic Cell*, Aug. 2006, pp. 1301-1313 vol. 5, No. 8.
Valton, J. et al. "5'-Cytosine-Phosphoguanine (CpG) Methylation Impacts the Activity of Natural and Engineered Meganucleases" *The Journal of Biological Chemistry*, Aug. 31, 2012, pp. 30139-30150, vol. 287, No. 36.
Panizza, S. et al. "Spo11-Accessory Proteins Link Double-Strand Break Sites to the Chromosome Axis in Early Meiotic Recombination" *Cell*, Aug. 5, 2011, pp. 372-383, vol. 146.
Sarno, R. et al. "Programming sites of meiotic crossovers using Spo11 fusion proteins" *Nucleic Acids Research*, 2017, pp. 1-14, vol. 45, No. 19, e164.

* cited by examiner

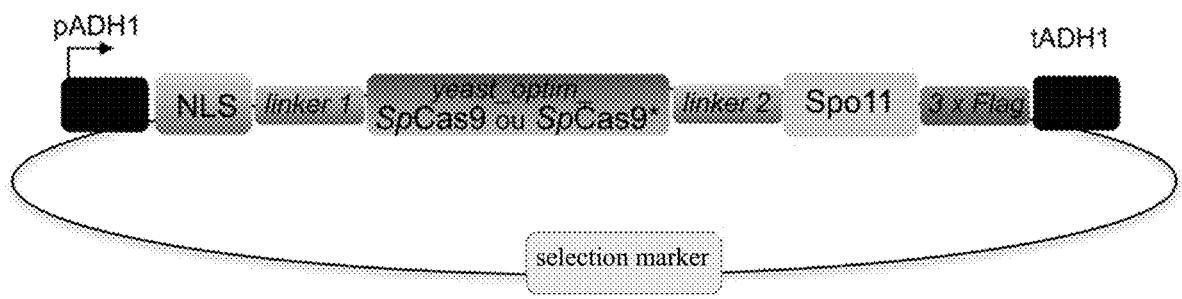
Figure 1
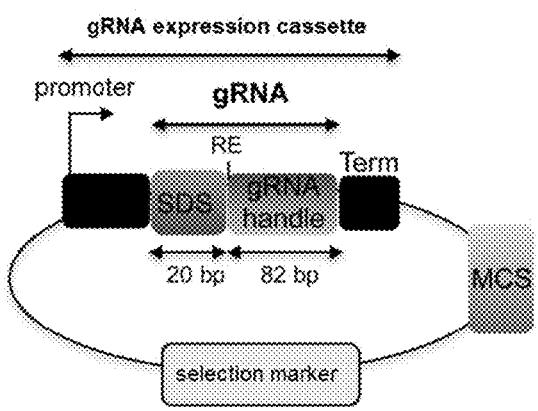
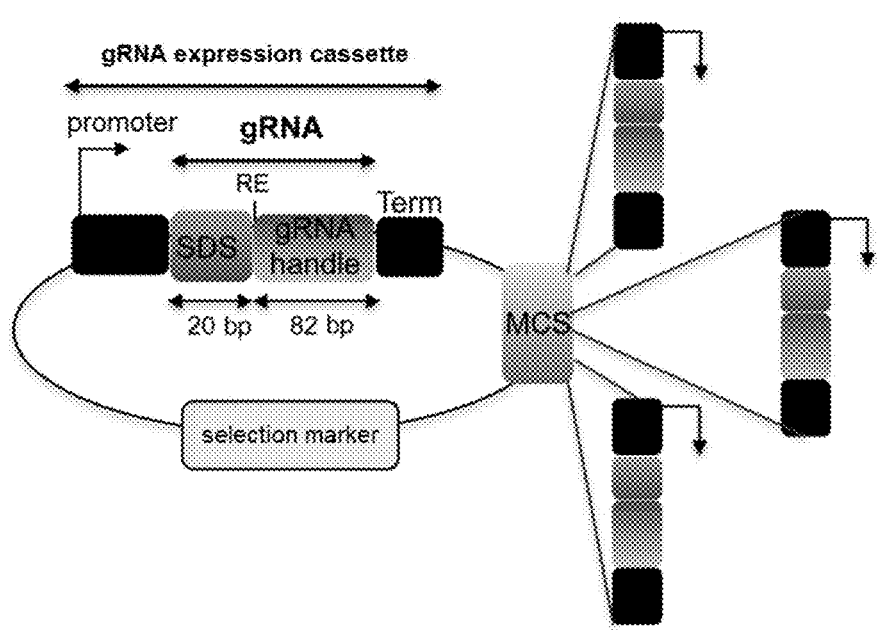
Figure 2

Guide RNA-UAS1 (*YCR048W* coding sequence)
5' CACACCTGAAGAGCAAGTCTgttttagagctagaaatagcaagttaaaataaggctagt
ccgttatcaacttgaaaaagtggcaccgagtcggtgctttttt 3' (SEQ ID NO: 10)

Guide RNA-UAS2 (*YCR048W* coding sequence)
5' TTCCACAACACGCCCACCTgttttagagctagaaatagcaagttaaaataaggctagt
ccgttatcaacttgaaaaagtggcaccgagtcggtgctttttt 3' (SEQ ID NO: 11)

Guide RNA-UAS D/E (*GAL2* promoter)
5' GATCACTCCGAACCGAGATTgttttagagctagaaatagcaagttaaaataaggctagt
ccgttatcaacttgaaaaagtggcaccgagtcggtgctttttt 3' (SEQ ID NO: 12)

sgRNA-SWC3 (*SWC3* coding sequence)
5' TGCGATTGTGTAATGAGTGGgttttagagctagaaatagcaagttaaaataaggctagt
ccgttatcaacttgaaaaagtggcaccgagtcggtgctttttt 3' (SEQ ID NO:13)

sgRNA-UAS-A (*GAL2* promoter)
5' CAATTCGGAAAGCTTCCTTCgttttagagctagaaatagcaagttaaaataaggctagt
ccgttatcaacttgaaaaagtggcaccgagtcggtgctttttt 3' (SEQ ID NO:14)

sgRNA-UAS-B (*GAL2* promoter)
5' TTGCCTCAGGAAGGCACCGGgttttagagctagaaatagcaagttaaaataaggctagt
ccgttatcaacttgaaaaagtggcaccgagtcggtgctttttt 3' (SEQ ID NO:15)

sgRNA-PUT4 (*PUT4* sequence)
5' GTTTTGAATTCCGATCACAAgttttagagctagaaatagcaagttaaaataaggctagt
ccgttatcaacttgaaaaagtggcaccgagtcggtgctttttt 3' (SEQ ID NO:17)

Figure 13

SEQUENCE LISTING

```
<160> NUMBER OF SEQ ID NOS: 18

<210> SEQ ID NO 1
<211> LENGTH: 12349
<212> TYPE: DNA
<213> ORGANISM: Artificial Sequence
<220> FEATURE:
<223> OTHER INFORMATION: Plasmid P1 comprising a nucleic acid encoding
      the wild-type Cas9-Spo11 fusion protein
<220> FEATURE:
<221> NAME/KEY: promoter
<222> LOCATION: (1)..(397)
<223> OTHER INFORMATION: ADH1 promoter
<220> FEATURE:
<221> NAME/KEY: gene
<222> LOCATION: (431)..(5974)
<223> OTHER INFORMATION: Gene encoding the Cas9-Spo11 fusion protein
<220> FEATURE:
<221> NAME/KEY: terminator
<222> LOCATION: (6010)..(6198)
<223> OTHER INFORMATION: ADH1 terminator
<220> FEATURE:
<221> NAME/KEY: rep_origin
<222> LOCATION: (6605)..(7287)
<223> OTHER INFORMATION: ColE1 bacterial origin of replication
<220> FEATURE:
<221> NAME/KEY: gene
<222> LOCATION: (7385)..(8045)
<223> OTHER INFORMATION: Ampicillin-resistance gene
<220> FEATURE:
<221> NAME/KEY: gene
<222> LOCATION: (8809)..(9631)
<223> OTHER INFORMATION: TRP1 gene
<220> FEATURE:
<221> NAME/KEY: rep_origin
<222> LOCATION: (9688)..(10126)
<223> OTHER INFORMATION: F1 origin of replication
<220> FEATURE:
<221> NAME/KEY: gene
<222> LOCATION: (10344)..(11363)
<223> OTHER INFORMATION: G418-resistance gene (KanMx)

<400> SEQUENCE: 1
caacttcttt tcttttttt tctttctct ctccccgtt gttgtctcac catatccgca      60
atgacaaaaa aatgatggaa gacactaaag gaaaaaatta acgacaaaga cagcaccaac    120
agatgtcgtt gttccagagc tgatgagggg tatctcgaag cacacgaaac ttttttcttc    180
```

-continued

| | |
|---|---|
| cttcattcac gcacactact ctctaatgag caacggtata cggccttcct tccagttact | 240 |
| tgaatttgaa ataaaaaaaa gtttgctgtc ttgctatcaa gtataaatag acctgcaatt | 300 |
| attaatcttt tgtttcctcg tcattgttct cgttcccttt cttccttgtt tcttttctg | 360 |
| cacaatattt caagctatac caagcataca atcaactcca agcttgaagc aagcctcctg | 420 |
| aaagactagt atgggaaaac ctattcctaa tcctctgctg ggcctggatt ctaccggagg | 480 |
| catgccccct aagaaaaagc ggaaggtgga cggcggaggt attcatggag ttcctgctgc | 540 |
| gatggacaag aagtattcta tcggactgga tatcgggact aatagcgtcg ggtgggccgt | 600 |
| gatcactgac gagtacaagg tgccctctaa gaagttcaag gtgctcggga acaccgaccg | 660 |
| gcattccatc aagaaaaatc tgatcggagc tctcctcttt gattcagggg agaccgctga | 720 |
| agcaacccgc ctcaagcgga ctgctagacg gcggtacacc aggaggaaga accggatttg | 780 |
| ttaccttcaa gagatattct ccaacgaaat ggcaaaggtc gacgacagct tcttccatag | 840 |
| gctggaagaa tcattcctcg tggaagagga taagaagcat gaacggcatc ccatcttcgg | 900 |
| taatatcgtc gacgaggtgg cctatcacga gaaatacccca accatctacc atcttcgcaa | 960 |
| aaagctggtg gactcaaccg acaaggcaga cctccggctt atctacctgg ccctggccca | 1020 |
| catgatcaag ttcagaggcc acttcctgat cgagggcgac ctcaatcctg acaatagcga | 1080 |
| tgtggataaa ctgttcatcc agctggtgca gacttacaac cagctctttg aagagaaccc | 1140 |
| catcaatgca agcggagtcg atgccaaggc cattctgtca gcccggctgt caaagagccg | 1200 |
| cagacttgag aatcttatcg ctcagctgcc gggtgaaaag aaaaatggac tgttcgggaa | 1260 |
| cctgattgct ctttcacttg gctgactcc caatttcaag tctaatttcg acctggcaga | 1320 |
| ggatgccaag ctgcaactgt ccaaggacac ctatgatgac gatctcgaca acctcctggc | 1380 |
| ccagatcggt gaccaatacg ccgacctttt ccttgctgct aagaatcttt ctgacgccat | 1440 |
| cctgctgtct gacattctcc gcgtgaacac tgaaatcacc aaggcccctc tttcagcttc | 1500 |
| aatgattaag cggtatgatg agcaccacca ggacctgacc ctgcttaagg cactcgtccg | 1560 |
| gcagcagctt ccggagaagt acaaggaaat cttctttgac cagtcaaaga atggatacgc | 1620 |
| cggctacatc gacggaggtg cctcccaaga ggaatttttat aagtttatca aacctatcct | 1680 |
| tgagaagatg gacggcaccg aagagctcct cgtgaaactg aatcgggagg atctgctgcg | 1740 |
| gaagcagcgc actttcgaca atgggagcat tccccaccag atccatcttg ggagcttca | 1800 |
| cgccatcctt cggcgccaag aggacttcta ccccttttctt aaggacaaca gggagaagat | 1860 |
| tgagaaaatt ctcactttcc gcatccccta ctacgtggga cccctcgcca gaggaaatag | 1920 |
| ccggtttgct tggatgacca gaaagtcaga agaaactatc actccctgga acttcgaaga | 1980 |
| ggtggtggac aagggagcca gcgctcagtc attcatcgaa cggatgacta acttcgataa | 2040 |
| gaacctcccc aatgagaagg tcctgccgaa acattccctg ctctacgagt actttaccgt | 2100 |
| gtacaacgag ctgaccaagg tgaaatatgt caccgaaggg atgaggaagc ccgcattcct | 2160 |
| gtcaggcgaa caaaagaagg caattgtgga ccttctgttc aagaccaata gaaaggtgac | 2220 |
| cgtgaagcag ctgaaggagg actatttcaa gaaaattgaa tgcttcgact ctgtggagat | 2280 |
| tagcggggtc gaagatcggt tcaacgcaag cctgggtacc taccatgatc tgcttaagat | 2340 |
| catcaaggac aaggatttc tggacaatga ggagaacgag gacatccttg aggacattgt | 2400 |
| cctgactctc actctgttcg aggacccgga aatgatcgag gagggctta agacctacgc | 2460 |
| ccatctgttc gacgataaag tgatgaagca acttaaacgg agaagatata ccggatgggg | 2520 |

```
acgccttagc cgcaaactca tcaacggaat ccgggacaaa cagagcggaa agaccattct   2580
tgatttcctt aagagcgacg gattcgctaa tcgcaacttc atgcaactta tccatgatga   2640
ttccctgacc tttaaggagg acatccagaa ggcccaagtg tctggacaag gtgactcact   2700
gcacgagcat atcgcaaatc tggctggttc acccgctatt aagaagggta ttctccagac   2760
cgtgaaagtc gtggacgagc tggtcaaggt gatgggtcgc cataaaccag agaacattgt   2820
catcgagatg gccagggaaa accagactac ccagaaggga cagaagaaca gcagggagcg   2880
gatgaaaaga attgaggaag ggattaagga gctcgggtca cagatcctta agagcaccc   2940
ggtgaaaaac acccagcttc agaatgagaa gctctatctg tactaccttc aaaatggacg   3000
cgatatgtat gtggaccaag agcttgatat caacaggctc tcagactacg acgtggacca   3060
tatcgtccct cagagcttcc tcaaagacga ctcaattgac aataaggtgc tgactcgctc   3120
agacaagaac cggggaaagt cagataacgt gcccctcagag gaagtcgtga aaaagatgaa   3180
gaactattgg cgccagcttc tgaacgcaaa gctgatcact cagcggaagt tcgacaatct   3240
cactaaggct gagaggggcg gactgagcga actggacaaa gcaggattca ttaaacggca   3300
acttgtggag actcggcaga ttactaaaca tgtcgcccaa atccttgact cacgcatgaa   3360
taccaagtac gacgaaaacg acaaaactta tccgcgaggtg aaggtgatta ccctgaagtc   3420
caagctggtc agcgatttca gaaaggactt tcaattctac aaagtgcggg agatcaataa   3480
ctatcatcat gctcatgacg catatctgaa tgccgtggtg ggaaccgccc tgatcaagaa   3540
gtacccaaag ctggaaagcg agttcgtgta cggagactac aaggtctacg acgtgcgcaa   3600
gatgattgcc aaatctgagc aggagatcgg aaaggccacc gcaaagtact tcttctacag   3660
caacatcatg aatttcttca gaccgaaat caccccttgca aacggtgaga tccggaagag   3720
gccgctcatc gagactaatg gggagactgg cgaaatcgtg tgggacaagg cagagattt   3780
cgctaccgtg cgcaaagtgc tttctatgcc tcaagtgaac atcgtgaaga aaaccgaggt   3840
gcaaaccgga ggcttttcta aggaatcaat cctccccaag cgcaactccg acaagctcat   3900
tgcaaggaag aaggattggg accctaagaa gtacggcgga ttcgattcac caactgtggc   3960
ttattctgtc ctggtcgtgg ctaaggtgga aaaaggaaag tctaagagc tcaagagcgt   4020
gaaggaactg ctgggtatca ccattatgga gcgcagctcc ttcgagaaga cccaattga   4080
ctttctcgaa gccaaaggtt acaaggaagt caagaaggac cttatcatca agctcccaaa   4140
gtatagcctg ttcgaactgg agaatgggcg gaagcggatg ctcgcctccg ctggcgaact   4200
tcagaagggt aatgagctgg ctctcccctc caagtacgtg aatttcctct accttgcaag   4260
ccattacgag aagctgaagg ggagccccga ggacaacgag caaaagcaac tgtttgtgga   4320
gcagcataag cattatctgg acgagatcat tgagcagatt tccgagtttt ctaaacgcgt   4380
cattctcgct gatgccaacc tcgataaagt ccttagcgca tacaataagc acagagacaa   4440
accaattcgg gagcaggctg agaatatcat ccacctgttc accctcacca atcttggtgc   4500
ccctgccgca ttcaagtact cgacaccac catcgaccgg aaacgctata cctccaccaa   4560
agaagtgctg gacgccaccc tcatccacca gagcatcacc ggactttacg aaactcggat   4620
tgacctctca cagctcggag gggatccgga atttatggcc atggaggccc ggggatccg   4680
tatggctttg gagggattgc ggaaaaaata taaacaagg caggaattgg tcaaagcact   4740
cactcctaaa agacggtcca ttcacttgaa ctccaatggt cactccaacg gaactccctg   4800
ttcaaacgca gatgttttgg ctcatattaa gcatttcctg tcattggcgg ctaattcatt   4860
agagcaacat caacagccta tttcaatcgt cttcaaaac aaaaaaaaaa aaggcgatac   4920
```

```
aagcagtcct gacattcaca caacattgga cttcccttg aatggcccgc atctatgcac    4980
tcatcagttc aagttgaaaa gatgcgcaat ccttttaaac ttattgaaag tcgttatgga    5040
aaaattaccg ctaggtaaaa acactacagt gagagatatc ttctactcca acgtggaatt    5100
gtttcaaaga caagcaaacg tagtccagtg gctggacgtt atacgcttta atttcaagct    5160
ctctccaaga aaatccttaa acattatacc agctcaaaag ggtttagttt attcgccttt    5220
ccccattgat atttatgaca atattctgac atgtgaaaat gaaccaaaga tgcaaaagca    5280
aacaattttc cctggtaagc cctgtctaat tccattttc caagatgatg cggtcatcaa    5340
gttagggaca acaagtatgt gtaatattgt aatagtggaa aaagaagctg tcttcaccaa    5400
attagtaaat aattatcaca agttgagtac aaataccatg ctcattacag gtaagggatt    5460
tccagatttc ttgacaaggt tattcctaaa aaaactagaa caatattgct ccaaattgat    5520
atcggactgt tctatattta ccgatgcgga cccctatggg attagcatag ccctaaatta    5580
tactcactcg aatgaacgca acgcttatat ttgcacgatg gcaaactata aaggaattcg    5640
tattacgcaa gttttggcac aaaataatga agtgcataac aaatccattc aattattgag    5700
tttgaatcag cgcgactact ccttagccaa gaatttgata gcatctctga ctgccaacag    5760
ctgggatatt gcaacttcac cattaaagaa cgtcatcata aatgtcagc gggaaatttt    5820
tttccaaaag aaagctgaaa tgaacgagat tgatgccaga attttgaat acaaatccca    5880
ccaccatcat catcacggag actacaagga tgacgatgac aaggactaca aggatgacga    5940
tgacaaggac tacaaggatg acgatgcaa gtaatgagtc gacaacccct gcagccaagc    6000
taattccggg cgaatttctt atgatttatg attttattta ttaaataagt tataaaaaaa    6060
ataagtgtat acaaatttta aagtgactct taggttttaa acgaaaaatt cttgttcttg    6120
agtaactctt tcctgtaggt caggttgctt tctcaggtat agcatgaggt cgctcttatt    6180
gaccacacct ctaccggcat gcaagcttgg cgtaatcatg gtcatagctg tttcctgtgt    6240
gaaattgtta tccgctcaca attccacaca acatacgagc cggaagcata aagtgtaaag    6300
cctggggtgc ctaatgagtg aggtaactca cattaattgc gttgcgctca ctgcccgctt    6360
tccagtcggg aaacctgtcg tgccagctgg attaatgaat cggccaacgc gcggggagag    6420
gcggtttgcg tattgggcgc tcttccgctt cctcgctcac tgactcgctg cgctcggtcg    6480
ttcggctgcg gcgagcggta tcagctcact caaaggcggt aatacggtta tccacagaat    6540
cagggggataa cgcaggaaag aacatgtgag caaaaggcca gcaaaaggcc aggaaccgta    6600
aaaaggccgc gttgctggcg ttttttccata ggctccgccc ccctgacgag catcacaaaa    6660
atcgacgctc aagtcagagg tggcgaaacc cgacaggact ataaagatac caggcgtttc    6720
ccctggaag ctccctcgtg cgctctcctg ttccgaccct gccgcttacc ggatacctgt    6780
ccgcctttct cccttcggga agcgtggcgc tttctcatag ctcacgctgt aggtatctca    6840
gttcggtgta ggtcgttcgc tccaagctgg gctgtgtgca cgaaccccc gttcagcccg    6900
accgctgcgc cttatccggt aactatcgtc ttgagtccaa cccggtaaga cacgacttat    6960
cgccactggc agcagccact ggtaacagga ttagcagagc gaggtatgta ggcggtgcta    7020
cagagttctt gaagtggtgg cctaactacg gctacactag aaggacagta tttggtatct    7080
gcgctctgct gaagccagtt accttcggaa aaagagttgg tagctcttga tccggcaaac    7140
aaaccaccgc tggtagcggt ggttttttg tttgcaagca gcagattacg cgcagaaaaa    7200
aaggatctca agaagatcct ttgatctttt ctacggggtc tgacgctcag tggaacgaaa    7260
```

```
actcacgttaa  agggattttg  gtcatgagat  tatcaaaaag  gatcttcacc  tagatccttt    7320
taaattaaaaa  atgaagtttt  aaatcaatct  aaagtatata  tgagtaaact  tggtctgaca    7380
gttaccaatg   cttaatcagt  gaggcaccta  tctcagcgat  ctgtctattt  cgttcatcca    7440
tagttgcctg   actccccgtc  gtgtagataa  ctacgatacg  ggagggctta  ccatctggcc    7500
ccagtgctgc   aatgatarccg  cgagacccac  gctcaccggc  ctccagattt  atcagcaata   7560
aaccagccag   ccggaagggc  cgagcgcaga  agtggtcctg  caactttatc  cgcctccatc    7620
cagtctatta   attgttgccg  ggaagctaga  gtaagtagtt  cgccagttaa  tagtttgcgc    7680
aacgttgttg   ccattgctac  aggcatcgtg  gtgtcacgct  cgtcgtttgg  tatggcttca    7740
ttcagctccg   gttcccaacg  atcaaggcga  gttacatgat  cccccatgtt  gtgcaaaaaa    7800
gcggttagct   ccttcggtcc  tccgatcgtt  gtcagaagta  agttggccgc  agtgttatca    7860
ctcatggtta   tggcagcact  gcataattct  cttactgtca  tgccatccgt  aagatgcttt    7920
tctgtgactg   gtgagtactc  aaccaagtca  ttctgagaat  agtgtatgcg  gcgaccgagt    7980
tgctcttgcc   cggcgtcaat  acgggataat  accgcgccac  atagcagaac  tttaaaagtg    8040
ctcatcattg   gaaaacgttc  ttcggggcga  aaactctcaa  ggatcttacc  gctgttgaga    8100
tccagttcga   tgtaacccac  tcgtgcaccc  aactgatctt  cagcatcttt  tactttcacc    8160
agcgtttctg   ggtgagcaaa  aacaggaagg  caaaatgccg  caaaaaaggg  aataagggcg    8220
acacggaaat   gttgaatact  catactcttc  ctttttcaat  attattgaag  catttatcag    8280
ggttattgtc   tcatgagcgg  atacatattt  gaatgtattt  agaaaaataa  acaaataggg    8340
gttccgcgca   catttccccg  aaaagtgcca  cctgacgtct  aagaaaccat  tattatcatg    8400
acattaacct   ataaaaatag  gcgtatcacg  aggccctttc  gtctcgcgcg  tttcggtgat    8460
gacggtgaaa   acctctgaca  catgcagctc  ccggagacgg  tcacagcttg  tctgtaagcg    8520
gatgccggga   gcagacaagc  ccgtcagggc  gcgtcagcgg  gtgttggcgg  gtgtcggggc    8580
tggcttaact   atgcggcatc  agagcagatt  gtactgagag  tgcaccataa  acgacattac    8640
tatatatata   atataggaag  catttaatag  acagcatcgt  aatatatgtg  tactttgcag    8700
ttatgacgcc   agatggcagt  agtggaagat  attctttatt  gaaaaatagc  ttgtcacctt    8760
acgtacaatc   ttgatccgga  gcttttcttt  ttttgccgat  taagaattaa  ttcggtcgaa    8820
aaaagaaaag   gagagggcca  agagggaggg  cattggtgac  tattgagcac  gtgagtatac    8880
gtgattaagc   acacaaaggc  agcttggagt  atgtctgtta  ttaatttcac  aggtagttct    8940
ggtccattgg   tgaaagtttg  cggcttgcag  agcacagagg  ccgcagaatg  tgctctagat    9000
tccgatgctg   acttgctggg  tattatatgt  gtgcccaata  gaaagagaac  aattgacccg    9060
gttattgcaa   ggaaaatttc  aagtcttgta  aaagcatata  aaaatagttc  aggcactccg    9120
aaatacttgg   ttggcgtgtt  tcgtaatcaa  cctaaggagg  atgttttggc  tctggtcaat    9180
gattacggca   ttgatatcgt  ccaactgcat  ggagatgagt  cgtggcaaga  ataccaagag    9240
ttcctcggtt   tgccagttat  taaaagactc  gtatttccaa  aagactgcaa  catactactc    9300
agtgcagctt   cacagaaacc  tcattcgttt  attcccttgt  ttgattcaga  agcaggtggg    9360
acaggtgaac   ttttggattg  gaactcgatt  tctgactggg  ttggaaggca  agagagcccc    9420
gaaagcttac   attttatgtt  agctggtgga  ctgacgccag  aaaatgttgg  tgatgcgctt    9480
agattaaatg   gcgttattgg  tgttgatgta  agcggaggtg  tggagacaaa  tggtgtaaaa    9540
gactctaaca   aaatagcaaa  tttcgtcaaa  aatgctaaga  aataggttat  tactgagtag    9600
tatttatttta  agtattgttt  gtgcacttgc  cgatctatgc  ggtgtgaaat  accgcacaga    9660
```

```
tgcgtaagga gaaaataccg catcaggaaa ttgtaaacgt taatattttg ttaaaattcg   9720
cgttaaattt ttgttaaatc agctcatttt ttaaccaata ggccgaaatc ggcaaaatcc   9780
cttataaatc aaaagaatag accgagatag ggttgagtgt tgttccagtt tggaacaaga   9840
gtccactatt aaagaacgtg gactccaacg tcaaagggcg aaaaaccgtc tatcagggcg   9900
atggcccact acgtgaacca tcaccctaat caagtttttt ggggtcgagg tgccgtaaag   9960
cactaaatcg gaaccctaaa gggagccccc gatttagagc ttgacgggga aagccggcga  10020
acgtggcgag aaaggaaggg aagaaagcga aaggagcggg cgctagggcg ctggcaagtg  10080
tagcggtcac gctgcgcgta accaccacac ccgccgcgct taatgcgccg ctacagggcg  10140
cgtcgcgcca ttcgccattc aggctgcgca actgttggga agggcgatcg gtgcgggcct  10200
cttcgctatt acgccagctg gcgaaagggg gatgtgctgc aaggcgatta agttgggtaa  10260
cgccagggtt ttcccagtca cgacgttgta aaacgacggc cagtcgtcca gctttcgat   10320 catcgatgaa ttcgagctcg ttttcgacag cagtatagcg accagcattc acatacgatt  10380
gacgcatgat attacttttct gcgcacttaa cttcgcatct gggcagatga tgtcgaggcg  10440
aaaaaaaata taaatcacgc taacatttga ttaaaataga acaactacaa tataaaaaaa  10500
ctatacaaat gacaagttct tgaaaacaag aatctttta ttgtcagtac tgattagaaa   10560
aactcatcga gcatcaaatg aaactgcaat ttattcatat caggattatc aataccatat  10620
ttttgaaaaa gccgtttctg taatgaagga gaaaactcac cgaggcagtt ccataggatg  10680
gcaagatcct ggtatcggtc tgcgattccg actcgtccaa catcaataca acctattaat  10740
ttcccctcgt caaaaataag gttatcaagt gagaaatcac catgagtgac gactgaatcc  10800
ggtgagaatg gcaaaagctt atgcatttct ttccagactt gttcaacagg ccagccatta  10860
cgctcgtcat caaaatcact cgcatcaacc aaaccgttat tcattcgtga ttgcgcctga  10920
gcgagacgaa atacgcgatc gctgttaaaa ggacaattac aaacaggaat cgaatgcaac  10980
cggcgcagga acactgccag cgcatcaaca atattttcac ctgaatcagg atattcttct  11040
aatacctgga atgctgtttt gccggggatc gcagtggtga gtaaccatgc atcatcagga  11100
gtacggataa aatgcttgat ggtcggaaga ggcataaatt ccgtcagcca gtttagtctg  11160
accatctcat ctgtaacatc attggcaacg ctacctttgc catgtttcag aaacaactct  11220
ggcgcatcgg gcttcccata caatcgatag attgtcgcac ctgattgccc gacattatcg  11280
cgagcccatt tatacccata taaatcagca tccatgttgg aatttaatcg cggcctcgaa  11340
acgtgagtct tttccttacc catggttgtt tatgttcgga tgtgatgtga gaactgtatc  11400
ctagcaagat tttaaaagga agtatatgaa agaagaacct cagtggcaaa tcctaacctt  11460
ttatatttct ctacagggc gcggcgtggg gacaattcaa cgcgtctgtg aggggagcgt   11520
ttccctgctc gcaggtctgc agcgaggagc cgtaattttt gcttcgcgcc gtgcggccat  11580
caaaatgtat ggatgcaaat gattatacat ggggatgtat gggctaaatg tacgggcgac  11640
agtcacatca tgcccctgag ctgcgcacgt caagactgtc aaggagggta ttctgggcct  11700
ccatgtcgct ggccgggtga cccggcgggg acgaggcaag ctaaacagat ctggcgcgcc  11760
ttaattaacc ccgagctcga gatcccgagc ttgcaaatta aagccttcga gcgtcccaaa  11820
accttctcaa gcaaggtttt cagtataatg ttacatgcgt acacgcgtct gtacagaaaa  11880
aaaagaaaaa tttgaaatat aaataacgtt cttaatacta acataactat aaaaaaataa  11940
atagggacct agacttcagg ttgtctaact ccttcctttt cggttagagc ggatgtgggg  12000
```

```
ggagggcgtg aatgtaagcg tgacataact aattacatga tatccttttg ttgtttccgg   12060
gtgtacaata tggacttcct cttttctggc aaccaaaccc atacatcggg attcctataa   12120
taccttcgtt ggtctcccta acatgtaggt ggcggagggg agatatacaa tagaacagat   12180
accagacaag acataatggg ctaaacaaaa ctacaccaat tacactgcct cattgatggt   12240
ggtacataac gaactaatac tgtagcccta gacttgatag ccatcatcat atcgaagttt   12300 cactacccctt tttccatttg ccatctattg aagtaataat aggcgcatg             12349
```

<210> SEQ ID NO 2
<211> LENGTH: 12349
<212> TYPE: DNA
<213> ORGANISM: Artificial Sequence
<220> FEATURE:
<223> OTHER INFORMATION: Plasmid P2 comprising a nucleic acid encoding
      the Cas9*-Spo11 fusion protein
<220> FEATURE:
<221> NAME/KEY: promoter
<222> LOCATION: (1)..(397)
<223> OTHER INFORMATION: ADH1 promoter
<220> FEATURE:
<221> NAME/KEY: gene
<222> LOCATION: (431)..(5974)
<223> OTHER INFORMATION: Gene encoding the Ca9*-Spo11 fusion protein
<220> FEATURE:
<221> NAME/KEY: terminator
<222> LOCATION: (6010)..(6198)
<223> OTHER INFORMATION: ADH1 terminator
<220> FEATURE:
<221> NAME/KEY: rep_origin
<222> LOCATION: (6605)..(7287)
<223> OTHER INFORMATION: ColE1 bacterial origin of replication
<220> FEATURE:
<221> NAME/KEY: gene
<222> LOCATION: (7385)..(8045)
<223> OTHER INFORMATION: Ampicillin-resistance gene
<220> FEATURE:
<221> NAME/KEY: gene
<222> LOCATION: (8809)..(9631)
<223> OTHER INFORMATION: TRP1 gene
<220> FEATURE:
<221> NAME/KEY: rep_origin
<222> LOCATION: (9688)..(10126)
<223> OTHER INFORMATION: F1 origin of replication
<220> FEATURE:
<221> NAME/KEY: gene
<222> LOCATION: (10344)..(11363)
<223> OTHER INFORMATION: G418-resistance gene (KanMX)

<400> SEQUENCE: 2

```
caacttctttt tctttttttt tcttttctct ctcccccgtt gttgtctcac catatccgca     60
atgacaaaaa aatgatggaa gacactaaag gaaaaaatta cgacaaaga cagcaccaac      120 agatgtcgtt gttccagagc tgatgagggg tatctcgaag cacacgaaac ttttttccttc    180 cttcattcac gcacactact ctctaatgag caacggtata cggccttcct tccagttact    240
tgaatttgaa ataaaaaaaa gtttgctgtc ttgctatcaa gtataaatag acctgcaatt    300
attaatcttt tgtttcctcg tcattgttct cgttcccttt cttccttgtt tctttttctg    360
cacaatattt caagctatac caagcataca atcaactcca agcttgaagc aagcctcctg   420
aaagactagt atgggaaaac ctattcctaa tcctctgctg ggcctggatt ctaccggagg   480
catggcccct aagaaaaagc ggaaggtgga cggcggaggt attcatgag ttcctgctgc     540 gatggacaag aagtattcta tcggactggc catcgggact aatagcgtcg ggtgggccgt   600
gatcactgac gagtacaagg tgccctctaa gaagttcaag gtgctcggga acaccgaccg   660
gcattccatc aagaaaaatc tgatcggagc tctcctcttt gattcagggg agaccgctga   720
```

```
agcaacccgc ctcaagcgga ctgctagacg gcggtacacc aggaggaaga accggatttg    780
ttaccttcaa gagatattct ccaacgaaat ggcaaaggtc gacgacagct tcttccatag    840
gctggaagaa tcattcctcg tggaagagga taagaagcat gaacggcatc ccatcttcgg    900
taatatcgtc gacgaggtgg cctatcacga gaaataccca accatctacc atcttcgcaa    960
aaagctggtg gactcaaccg acaaggcaga cctccggctt atctacctgg ccctggccca   1020
catgatcaag ttcagaggcc acttcctgat cgagggcgac ctcaatcctg acaatagcga   1080
tgtggataaa ctgttcatcc agctggtgca gacttacaac cagctctttg aagagaaccc   1140
catcaatgca agcggagtcg atgccaaggc cattctgtca gcccggctgt caaagagccg   1200
cagacttgag aatcttatcg ctcagctgcc gggtgaaaag aaaaatggac tgttcgggaa   1260
cctgattgct ctttcacttg gcctgactcc caatttcaag tctaatttcg acctggcaga   1320
ggatgccaag ctgcaactgt ccaaggacac ctatgatgac gatctcgaca acctcctggc   1380
ccagatcggt gaccaatacg ccgacctttt ccttgctgct aagaatcttt ctgacgccat   1440
cctgctgtct gacattctcc gcgtgaacac tgaaatcacc aaggcccctc tttcagcttc   1500
aatgattaag cggtatgatg agcaccacca ggacctgacc ctgcttaagg cactcgtccg   1560
gcagcagctt ccggagaagt acaaggaaat cttctttgac cagtcaaaga atggatacgc   1620
cggctacatc gacggaggtg cctcccaaga ggaatttat aagtttatca aacctatcct   1680
tgagaagatg gacggcaccg aagagctcct cgtgaaactg aatcgggagg atctgctgcg   1740
gaagcagcgc actttcgaca atgggagcat tccccaccag atccatcttg gggagcttca   1800
cgccatcctt cggcgccaag aggacttcta cccctttctt aaggacaaca gggagaagat   1860
tgagaaaatt ctcactttcc gcatccccta ctacgtggga cccctcgcca gagggaaatag   1920 ccggtttgct tggatgacca gaaagtcaga agaaactatc actccctgga acttcgaaga   1980
ggtggtggac aagggagcca gcgctcagtc attcatcgaa cggatgacta acttcgataa   2040
gaacctcccc aatgagaagg tcctgccgaa acattccctg ctctacgagt actttaccgt   2100
gtacaacgag ctgaccaagg tgaaatatgt caccgaaggg atgaggaagc ccgcattcct   2160
gtcaggcgaa caaaagaagg caattgtgga ccttctgttc aagaccaata aaaaggtgac   2220
cgtgaagcag ctgaaggagg actatttcaa gaaaattgaa tgcttcgact ctgtggagat   2280
tagcggggtc gaagatcggt tcaacgcaag cctgggtacc taccatgatc tgcttaagat   2340
catcaaggac aaggattttc tggacaatga ggagaacgag gacatccttg aggacattgt   2400
cctgactctc actctgttcg aggacccgga aatgatcgag gagaggctta agacctacgc   2460
ccatctgttc gacgataaag tgatgaagca acttaaacgg agaagatata ccggatgggg   2520 acgcctttagc cgcaaactca tcaacggaat ccgggacaaa cagagcggaa agaccattct   2580
tgatttcctt aagagcgacg gattcgctaa tcgcaacttc atgcaactta ccatgatga   2640 ttccctgacc tttaaggagg acatccgaaa ggcccaagtg tctggacaag gtgactcact   2700
gcacgagcat atcgcaaatc tggctggttc acccgctatt aagaagggta ttctccagac   2760
cgtgaaagtc gtggacgagc tggtcaaggt gatgggtcgc ataaaccaga gaacattgt   2820 catcgagatg gccagggaaa accagactac ccagaaggga cagaagaaca gcagggagcg   2880
gatgaaaaga attgaggaag ggattaagga gctcgggtca cagatcctta agagcaccc   2940 ggtggaaaac acccagcttc agaatgagaa gctctatctg tactaccttc aaaatggacg   3000
cgatatgtat gtggaccaag agcttgatat caacaggctc tcagactacg acgtggacgc   3060
tatcgtccct cagagcttcc tcaaagacga ctcaattgac aataaggtgc tgactcgctc   3120
```

```
agacaagaac cggggaaagt cagataacgt gccctcagag gaagtcgtga aaaagatgaa    3180
gaactattgg cgccagcttc tgaacgcaaa gctgatcact cagcggaagt tcgacaatct    3240
cactaaggct gagaggggcg gactgagcga actggacaaa gcaggattca ttaaacggca    3300
acttgtggag actcggcaga ttactaaaca tgtcgcccaa atccttgact cacgcatgaa    3360
taccaagtac gacgaaaacg acaaacttat ccgcgaggtg aaggtgatta ccctgaagtc    3420
caagctggtc agcgatttca gaaaggactt tcaattctac aaagtgcggg agatcaataa    3480
ctatcatcat gctcatgacg catatctgaa tgccgtggtg ggaaccgccc tgatcaagaa    3540
gtacccaaag ctggaaagcg agttcgtgta cggagactac aaggtctacg acgtgcgcaa    3600
gatgattgcc aaatctgagc aggagatcgg aaaggccacc gcaaagtact tcttctacag    3660
caacatcatg aatttcttca gaccgaaaat caccccttgca acggtgaga tccggaagag    3720 gccgctcatc gagactaatg gggagactgg cgaaatcgtg tgggacaagg cagagattt    3780 cgctaccgtg cgcaaagtgc tttctatgcc tcaagtgaac atcgtgaaga aaaccgaggt    3840
gcaaaccgga ggcttttcta aggaatcaat cctccccaag cgcaactccg acaagctcat    3900
tgcaaggaag aaggattggg accctaagaa gtacggcgga ttcgattcac caactgtggc    3960
ttattctgtc ctggtcgtgg ctaaggtgga aaaaggaaag tctaagaagc tcaagagcgt    4020
gaaggaactg ctgggtatca ccattatgga gcgcagctcc ttcgagaaga acccaattga    4080
ctttctcgaa gccaaaggtt acaaggaagt caagaaggac cttatcatca agctcccaaa    4140
gtatagcctg ttcgaactgg agaatgggcg gaagcggatg ctcgcctccg ctggcgaact    4200
tcagaagggt aatgagctgg ctctcccctc caagtacgtg aatttcctct accttgcaag    4260
ccattacgag aagctgaagg ggagccccga ggacaacgag caaaagcaac tgtttgtgga    4320
gcagcataag cattatctgg acgagatcat tgagcagatt ccgagttttt ctaaacgcgt    4380
cattctcgct gatgccaacc tcgataaagt ccttagcgca tacaataagc acagagacaa    4440
accaattcgg gagcaggctg agaatatcat ccacctgttc accctcacca atcttggtgc    4500
ccctgccgca ttcaagtact tcgacaccac catcgaccgg aaacgctata cctccaccaa    4560
agaagtgctg gacgccaccc tcatccacca gagcatcacc ggactttacg aaactcggat    4620
tgacctctca cagctcggag gggatccgga atttatggcc atggaggccc cggggatccg    4680
tatggctttg gagggattgc ggaaaaaata taaaacaagg caggaattgg tcaaagcact    4740
cactcctaaa agacggtcca ttcacttgaa ctccaatggt cactccaacg gaactccctg    4800
ttcaaacgca gatgttttgg ctcatattaa gcatttcctg tcattggcgg ctaattcatt    4860
agagcaacat caacagccta tttcaatcgt cttcaaaac aaaaaaaaa aaggcgatac    4920 aagcagtcct gacattcaca caacattgga cttccctttg aatggcccgc atctatgcac    4980
tcatcagttc aagttgaaaa gatgcgcaat ccttttaaac ttattgaaag tcgttatgga    5040
aaaattaccg ctaggtaaaa acactacagt gagagatatc ttctactcca acgtggaatt    5100
gtttcaaaga caagcaaacg tagtccagtg gctggacgtt atacgcttta atttcaagct    5160
ctctccaaga aaatccttaa acattatacc agctcaaaag ggtttagttt attcgccttt    5220
ccccattgat atttatgaca atattctgac atgtgaaaat gaaccaaaga tgcaaaagca    5280
aacaattttc cctggtaagc cctgtctaat tccattttc caagatgatg cggtcatcaa    5340
gttagggaca acaagtatgt gtaatattgt aatagtggaa aaagaagctg tcttcaccaa    5400
attagtaaat aattatcaca agttgagtac aaataccatg ctcattacag gtaagggatt    5460
```

```
tccagatttc ttgacaaggt tattcctaaa aaaactagaa caatattgct ccaaattgat      5520
atcggactgt tctatattta ccgatgcgga cccctatggg attagcatag ccctaaatta      5580
tactcactcg aatgaacgca acgcttatat ttgcacgatg gcaaactata aaggaattcg      5640
tattacgcaa gttttggcac aaaataatga agtgcataac aaatccattc aattattgag      5700
tttgaatcag cgcgactact ccttagccaa gaatttgata gcatctctga ctgccaacag      5760
ctgggatatt gcaacttcac cattaaagaa cgtcatcata aatgtcagc gggaaatttt       5820 tttccaaaag aaagctgaaa tgaacgagat tgatgccaga attttttgaat acaaatccca     5880 ccaccatcat catcacggag actacaagga tgacgatgac aaggactaca aggatgacga      5940
tgacaaggac tacaaggatg acgatgacaa gtaatgagtc gacaacccct gcagccaagc      6000
taattccggg cgaatttctt atgatttatg attttatta ttaaataagt tataaaaaaa        6060
ataagtgtat acaaatttta aagtgactct taggttttaa aacgaaaatt cttgttcttg      6120
agtaactctt tcctgtaggt caggttgctt tctcaggtat agcatgaggt cgctcttatt      6180
gaccacacct ctaccggcat gcaagcttgg cgtaatcatg gtcatagctg tttcctgtgt      6240
gaaattgtta tccgctcaca attccacaca acatacgagc cggaagcata aagtgtaaag      6300
cctggggtgc ctaatgagtg aggtaactca cattaattgc gttgcgctca ctgcccgctt      6360
tccagtcggg aaacctgtcg tgccagctgg attaatgaat cggccaacgc gcggggagag      6420
gcggtttgcg tattgggcgc tcttccgctt cctcgctcac tgactcgctg cgctcggtcg      6480
ttcggctgcg gcgagcggta tcagctcact caaaggcggt aatacggtta tccacagaat      6540
caggggataa cgcaggaaag aacatgtgag caaaaggcca gcaaaaggcc aggaaccgta      6600
aaaaggccgc gttgctggcg ttttccata ggctccgccc cctgacgag catcacaaaa         6660 atcgacgctc aagtcagagg tggcgaaacc cgacaggact ataaagatac caggcgtttc      6720
cccctggaag ctccctcgtg cgctctcctg ttccgaccct gccgcttacc ggatacctgt      6780
ccgcctttct cccttcggga agcgtggcgc tttctcatag ctcacgctgt aggtatctca      6840
gttcggtgta ggtcgttcgc tccaagctgg gctgtgtgca cgaaccccc gttcagcccg       6900 accgctgcgc cttatccggt aactatcgtc ttgagtccaa cccggtaaga cacgacttat      6960
cgccactggc agcagccact ggtaacagga ttagcagagc gaggtatgta ggcggtgcta      7020
cagagttctt gaagtggtgg cctaactacg gctacactag aaggacagta tttggtatct      7080
gcgctctgct gaagccagtt accttcggaa aaagagttgg tagctcttga tccggcaaac      7140
aaaccaccgc tggtagcggt ggtttttttg tttgcaagca gcagattacg cgcagaaaaa      7200
aaggatctca agaagatcct ttgatctttt ctacgggtc tgacgctcag tggaacgaaa        7260
actcacgtta agggattttg gtcatgagat tatcaaaaag gatcttcacc tagatccttt      7320
taaattaaaa atgaagtttt aaatcaatct aaagtatata tgagtaaact tggtctgaca      7380
gttaccaatg cttaatcagt gaggcaccta tctcagcgat ctgtctattt cgttcatcca      7440
tagttgcctg actccccgtc gtgtagataa ctacgatacg ggagggctta ccatctggcc      7500
ccagtgctgc aatgataccg cgagacccac gctcaccggc tccagattt atcagcaata       7560 aaccagccag ccggaaggc cgagcgcaga agtggtcctg caactttatc cgcctccatc       7620
cagtctatta attgttgccg ggaagctaga gtaagtagtt cgccagttaa tagtttgcgc      7680
aacgttgttg ccattgctac aggcatcgtg gtgtcacgct cgtcgtttgg tatggcttca     7740
ttcagctccg gttcccaacg atcaaggcga gttacatgat cccccatgtt gtgcaaaaaa     7800
gcggttagct ccttcggtcc tccgatcgtt gtcagaagta agttggccgc agtgttatca     7860
```

```
ctcatggtta tggcagcact gcataattct cttactgtca tgccatccgt aagatgcttt    7920
tctgtgactg gtgagtactc aaccaagtca ttctgagaat agtgtatgcg gcgaccgagt    7980
tgctcttgcc cggcgtcaat acgggataat accgcgccac atagcagaac tttaaaagtg    8040
ctcatcattg gaaaacgttc ttcggggcga aaactctcaa ggatcttacc gctgttgaga    8100
tccagttcga tgtaacccac tcgtgcaccc aactgatctt cagcatcttt tactttcacc    8160
agcgtttctg ggtgagcaaa aacaggaagg caaaatgccg caaaaagggg ataagggcg     8220 acacggaaat gttgaatact catactcttc cttttttcaat attattgaag catttatcag   8280
ggttattgtc tcatgagcgg atacatattt gaatgtattt agaaaaataa acaaataggg    8340
gttccgcgca catttccccg aaaagtgcca cctgacgtct aagaaaccat tattatcatg    8400
acattaacct ataaaaatag gcgtatcacg aggccctttc gtctcgcgcg tttcggtgat    8460
gacggtgaaa acctctgaca catgcagctc ccggagacgg tcacagcttg tctgtaagcg    8520
gatgccggga gcagacaagc ccgtcagggc gcgtcagcgg gtgttggcgg gtgtcggggc    8580
tggcttaact atgcggcatc agagcagatt gtactgagag tgcaccataa acgacattac    8640
tatatatata atataggaag catttaatag acagcatcgt aatatatgtg tactttgcag    8700
ttatgacgcc agatggcagt agtggaagat attctttatt gaaaaatagc ttgtcacctt    8760
acgtacaatc ttgatccgga gcttttcttt ttttgccgat taagaattaa ttcggtcgaa    8820
aaaagaaaag gagagggcca agagggaggg cattggtgac tattgagcac gtgagtatac    8880
gtgattaagc acacaaaggc agcttggagt atgtctgtta ttaatttcac aggtagttct    8940
ggtccattgg tgaaagtttg cggcttgcag agcacagagg ccgcagaatg tgctctagat    9000
tccgatgctg acttgctggg tattatatgt gtgcccaata gaaagagaac aattgacccg    9060
gttattgcaa ggaaaatttc aagtcttgta aaagcatata aaaatagttc aggcactccg    9120
aaatacttgg ttggcgtgtt tcgtaatcaa cctaaggagg atgttttggc tctggtcaat    9180
gattacggca ttgatatcgt ccaactgcat ggagatgagt cgtggcaaga ataccaagag    9240
ttcctcggtt tgccagttat taaaagactc gtatttccaa aagactgcaa catactactc    9300
agtgcagctt cacagaaacc tcattcgttt attcccttgt ttgattcaga agcaggtggg    9360
acaggtgaac ttttggattg gaactcgatt tctgactggg ttggaaggca agagagcccc    9420
gaaagcttac attttatgtt agctggtgga ctgacgccag aaaatgttgg tgatgcgctt    9480
agattaaatg gcgttattgg tgttgatgta agcggaggtg tggagacaaa tggtgtaaaa    9540
gactctaaca aaatagcaaa tttcgtcaaa aatgctaaga aataggttat tactgagtag    9600
tatttattta agtattgttt gtgcacttgc cgatctatgc ggtgtgaaat accgcacaga    9660
tgcgtaagga gaaaataccg catcaggaaa ttgtaaacgt taatattttg ttaaaattcg    9720
cgttaaattt ttgttaaatc agctcatttt ttaaccaata ggccgaaatc ggcaaaatcc    9780
cttataaatc aaaagaatag accgagatag ggttgagtgt tgttccagtt tggaacaaga    9840
gtccactatt aaagaacgtg gactccaacg tcaaagggcg aaaaaccgtc tatcagggcg    9900
atggcccact acgtgaacca tcaccctaat caagttttt gggtcgagg tgccgtaaag     9960 cactaaatcg gaaccctaaa gggagccccc gatttagagc ttgacgggga agccggcga    10020 acgtggcgag aaaggaaggg aagaaagcga aggagcggg cgctagggcg ctggcaagtg    10080
tagcggtcac gctgcgcgta accaccacac ccgccgcgct taatgcgccg ctacagggcg    10140
cgtcgcgcca ttcgccattc aggctgcgca actgttggga agggcgatcg gtgcgggcct    10200
```

```
cttcgctatt acgccagctg gcgaaagggg gatgtgctgc aaggcgatta agttgggtaa    10260
cgccagggtt ttcccagtca cgacgttgta aaacgacggc cagtcgtcca agctttcgat    10320
catcgatgaa ttcgagctcg ttttcgacag cagtatagcg accagcattc acatacgatt    10380
gacgcatgat attactttct gcgcacttaa cttcgcatct gggcagatga tgtcgaggcg    10440
aaaaaaaata taaatcacgc taacatttga ttaaaataga caactacaa tataaaaaaa     10500 ctatacaaat gacaagttct tgaaaacaag aatctttta ttgtcagtac tgattagaaa     10560
aactcatcga gcatcaaatg aaactgcaat ttattcatat caggattatc aataccatat    10620
ttttgaaaaa gccgtttctg taatgaagga gaaaactcac cgaggcagtt ccataggatg    10680
gcaagatcct ggtatcggtc tgcgattccg actcgtccaa catcaataca acctattaat    10740
ttcccctcgt caaaataag gttatcaagt gagaaatcac catgagtgac gactgaatcc     10800
ggtgagaatg gcaaaagctt atgcatttct ttccagactt gttcaacagg ccagccatta    10860
cgctcgtcat caaatcact cgcatcaacc aaaccgttat tcattcgtga ttgcgcctga     10920
gcgagacgaa atacgcgatc gctgttaaaa ggacaattac aaacaggaat cgaatgcaac    10980
cggcgcagga acactgccag cgcatcaaca atattttcac ctgaatcagg atattcttct    11040
aatacctgga atgctgtttt gccggggatc gcagtggtga gtaaccatgc atcatcagga    11100
gtacggataa aatgcttgat ggtcggaaga ggcataaatt ccgtcagcca gtttagtctg    11160
accatctcat ctgtaacatc attggcaacg ctacctttgc catgtttcag aaacaactct    11220
ggcgcatcgg gcttcccata caatcgatag attgtcgcac ctgattgccc gacattatcg    11280
cgagcccatt tatacccata taaatcagca tccatgttgg aatttaatcg cggcctcgaa    11340
acgtgagtct tttccttacc catggttgtt tatgttcgga tgtgatgtga aactgtatc     11400 ctagcaagat tttaaaagga agtatatgaa agaagaacct cagtggcaaa tcctaaccttt   11460 ttatatttct ctacaggggc gcggcgtggg gacaattcaa cgcgtctgtg agggagcgt     11520 ttccctgctc gcaggtctgc agcgaggagc cgtaattttt gcttcgcgcc gtgcggccat    11580
caaaatgtat ggatgcaaat gattatacat ggggatgtat gggctaaatg tacgggcgac    11640
agtcacatca tgccctgag ctgcgcacgt caagactgtc aaggaggta ttctgggcct      11700 ccatgtcgct ggccgggtga cccggcgggg acgaggcaag ctaaacagat ctggcgcgcc    11760
ttaattaacc ccgagctcga gatcccgagc ttgcaaatta aagccttcga gcgtcccaaa    11820
accttctcaa gcaaggtttt cagtataatg ttacatgcgt acacgcgtct gtacagaaaa    11880
aaaagaaaaa tttgaaatat aaataacgtt cttaatacta acataactat aaaaaaataa    11940
atagggacct agacttcagg ttgtctaact ccttcctttt cggttagagc ggatgtgggg    12000
ggagggcgtg aatgtaagcg tgacataact aattacatga tatccttttg ttgtttccgg    12060
gtgtacaata tggacttcct cttttctggc aaccaaaccc atacatcggg attcctataa    12120
taccttcgtt ggtctcccta acatgtaggg ggcggagggg agatatacaa tagaacagat    12180
accagacaag acataatggg ctaaacaaaa ctacaccaat tacactgcct cattgatggt    12240
ggtacataac gaactaatac tgtagcccta gacttgatag ccatcatcat atcgaagttt    12300
cactacccct tttccattt ccatctattg aagtaataat aggcgcatg               12349
```

<210> SEQ ID NO 3  
<211> LENGTH: 7  
<212> TYPE: PRT  
<213> ORGANISM: Artificial Sequence  
<220> FEATURE:  
<223> OTHER INFORMATION: Nuclear localization signal sequence -continued

```
<400> SEQUENCE: 3

Pro Lys Lys Arg Lys Val
1               5

<210> SEQ ID NO 4
<211> LENGTH: 20
<212> TYPE: PRT
<213> ORGANISM: HIV-I

<400> SEQUENCE: 4

Gly Arg Lys Lys Arg Arg Gln Arg Arg Pro Pro Gln Pro Lys Lys
1               5                   10                  15

Lys Arg Lys Val
            20

<210> SEQ ID NO 5
<211> LENGTH: 19
<212> TYPE: PRT
<213> ORGANISM: Human hepatitus B virus

<400> SEQUENCE: 5

Pro Leu Ser Ser Ile Phe Ser Arg Ile Gly Asp Pro Pro Lys Lys
1               5                   10                  15

Arg Lys Val

<210> SEQ ID NO 6
<211> LENGTH: 1839
<212> TYPE: PRT
<213> ORGANISM: Artificial Sequence
<220> FEATURE:
<223> OTHER INFORMATION: Fusion protein comprising the wild-type
      Cas9-Spo11 construction

<400> SEQUENCE: 6

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Gly Ile His
                20                  25                  30

Gly Val Pro Ala Ala Met Asp Lys Lys Tyr Ser Ile Gly Leu Asp Ile
            35                  40                  45

Gly Thr Asn Ser Val Gly Trp Ala Val Ile Thr Asp Glu Tyr Lys Val
        50                  55                  60

Pro Ser Lys Lys Phe Lys Val Leu Gly Asn Thr Asp Arg His Ser Ile
65                  70                  75                  80

Lys Lys Asn Leu Ile Gly Ala Leu Leu Phe Asp Ser Gly Glu Thr Ala
                85                  90                  95

Glu Ala Thr Arg Leu Lys Arg Thr Ala Arg Arg Arg Tyr Thr Arg Arg
                100                 105                 110

Lys Asn Arg Ile Cys Tyr Leu Gln Glu Ile Phe Ser Asn Glu Met Ala
            115                 120                 125

Lys Val Asp Asp Ser Phe Phe His Arg Leu Glu Glu Ser Phe Leu Val
        130                 135                 140

Glu Glu Asp Lys Lys His Glu Arg His Pro Ile Phe Gly Asn Ile Val
145                 150                 155                 160

Asp Glu Val Ala Tyr His Glu Lys Tyr Pro Thr Ile Tyr His Leu Arg
                165                 170                 175

Lys Lys Leu Val Asp Ser Thr Asp Lys Ala Asp Leu Arg Leu Ile Tyr
                180                 185                 190
```

```
Leu Ala Leu Ala His Met Ile Lys Phe Arg Gly His Phe Leu Ile Glu
            195                 200                 205

Gly Asp Leu Asn Pro Asp Asn Ser Asp Val Asp Lys Leu Phe Ile Gln
    210                 215                 220

Leu Val Gln Thr Tyr Asn Gln Leu Phe Glu Glu Asn Pro Ile Asn Ala
225                 230                 235                 240

Ser Gly Val Asp Ala Lys Ala Ile Leu Ser Ala Arg Leu Ser Lys Ser
            245                 250                 255

Arg Arg Leu Glu Asn Leu Ile Ala Gln Leu Pro Gly Glu Lys Lys Asn
        260                 265                 270

Gly Leu Phe Gly Asn Leu Ile Ala Leu Ser Leu Gly Leu Thr Pro Asn
            275                 280                 285

Phe Lys Ser Asn Phe Asp Leu Ala Glu Asp Ala Lys Leu Gln Leu Ser
        290                 295                 300

Lys Asp Thr Tyr Asp Asp Asp Leu Asp Asn Leu Leu Ala Gln Ile Gly
305                 310                 315                 320

Asp Gln Tyr Ala Asp Leu Phe Leu Ala Ala Lys Asn Leu Ser Asp Ala
            325                 330                 335

Ile Leu Leu Ser Asp Ile Leu Arg Val Asn Thr Glu Ile Thr Lys Ala
        340                 345                 350

Pro Leu Ser Ala Ser Met Ile Lys Arg Tyr Asp Glu His His Gln Asp
            355                 360                 365

Leu Thr Leu Leu Lys Ala Leu Val Arg Gln Gln Leu Pro Glu Lys Tyr
    370                 375                 380

Lys Glu Ile Phe Phe Asp Gln Ser Lys Asn Gly Tyr Ala Gly Tyr Ile
385                 390                 395                 400

Asp Gly Gly Ala Ser Gln Glu Glu Phe Tyr Lys Phe Ile Lys Pro Ile
            405                 410                 415

Leu Glu Lys Met Asp Gly Thr Glu Glu Leu Leu Val Lys Leu Asn Arg
        420                 425                 430

Glu Asp Leu Leu Arg Lys Gln Arg Thr Phe Asp Asn Gly Ser Ile Pro
    435                 440                 445

His Gln Ile His Leu Gly Glu Leu His Ala Ile Leu Arg Arg Gln Glu
    450                 455                 460

Asp Phe Tyr Pro Phe Leu Lys Asp Asn Arg Glu Lys Ile Glu Lys Ile
465                 470                 475                 480

Leu Thr Phe Arg Ile Pro Tyr Tyr Val Gly Pro Leu Ala Arg Gly Asn
            485                 490                 495

Ser Arg Phe Ala Trp Met Thr Arg Lys Ser Glu Glu Thr Ile Thr Pro
        500                 505                 510

Trp Asn Phe Glu Glu Val Val Asp Lys Gly Ala Ser Ala Gln Ser Phe
    515                 520                 525

Ile Glu Arg Met Thr Asn Phe Asp Lys Asn Leu Pro Asn Glu Lys Val
    530                 535                 540

Leu Pro Lys His Ser Leu Leu Tyr Glu Tyr Phe Thr Val Tyr Asn Glu
545                 550                 555                 560

Leu Thr Lys Val Lys Tyr Val Thr Glu Gly Met Arg Lys Pro Ala Phe
            565                 570                 575

Leu Ser Gly Glu Gln Lys Lys Ala Ile Val Asp Leu Leu Phe Lys Thr
        580                 585                 590

Asn Arg Lys Val Thr Val Lys Gln Leu Lys Glu Asp Tyr Phe Lys Lys
        595                 600                 605
```

```
Ile Glu Cys Phe Asp Ser Val Glu Ile Ser Gly Val Glu Asp Arg Phe
610                 615                 620

Asn Ala Ser Leu Gly Thr Tyr His Asp Leu Leu Lys Ile Ile Lys Asp
625                 630                 635                 640

Lys Asp Phe Leu Asp Asn Glu Glu Asn Glu Asp Ile Leu Glu Asp Ile
                645                 650                 655

Val Leu Thr Leu Thr Leu Phe Glu Asp Arg Glu Met Ile Glu Glu Arg
                660                 665                 670

Leu Lys Thr Tyr Ala His Leu Phe Asp Asp Lys Val Met Lys Gln Leu
                675                 680                 685

Lys Arg Arg Arg Tyr Thr Gly Trp Gly Arg Leu Ser Arg Lys Leu Ile
690                 695                 700

Asn Gly Ile Arg Asp Lys Gln Ser Gly Lys Thr Ile Leu Asp Phe Leu
705                 710                 715                 720

Lys Ser Asp Gly Phe Ala Asn Arg Asn Phe Met Gln Leu Ile His Asp
                725                 730                 735

Asp Ser Leu Thr Phe Lys Glu Asp Ile Gln Lys Ala Gln Val Ser Gly
                740                 745                 750

Gln Gly Asp Ser Leu His Glu His Ile Ala Asn Leu Ala Gly Ser Pro
                755                 760                 765

Ala Ile Lys Lys Gly Ile Leu Gln Thr Val Lys Val Val Asp Glu Leu
770                 775                 780

Val Lys Val Met Gly Arg His Lys Pro Glu Asn Ile Val Ile Glu Met
785                 790                 795                 800

Ala Arg Glu Asn Gln Thr Thr Gln Lys Gly Gln Lys Asn Ser Arg Glu
                805                 810                 815

Arg Met Lys Arg Ile Glu Glu Gly Ile Lys Glu Leu Gly Ser Gln Ile
                820                 825                 830

Leu Lys Glu His Pro Val Glu Asn Thr Gln Leu Gln Asn Glu Lys Leu
                835                 840                 845

Tyr Leu Tyr Tyr Leu Gln Asn Gly Arg Asp Met Tyr Val Asp Gln Glu
850                 855                 860

Leu Asp Ile Asn Arg Leu Ser Asp Tyr Asp Val Asp His Ile Val Pro
865                 870                 875                 880

Gln Ser Phe Leu Lys Asp Asp Ser Ile Asp Asn Lys Val Leu Thr Arg
                885                 890                 895

Ser Asp Lys Asn Arg Gly Lys Ser Asp Asn Val Pro Ser Glu Glu Val
                900                 905                 910

Val Lys Lys Met Lys Asn Tyr Trp Arg Gln Leu Leu Asn Ala Lys Leu
                915                 920                 925

Ile Thr Gln Arg Lys Phe Asp Asn Leu Thr Lys Ala Glu Arg Gly Gly
930                 935                 940

Leu Ser Glu Leu Asp Lys Ala Gly Phe Ile Lys Arg Gln Leu Val Glu
945                 950                 955                 960

Thr Arg Gln Ile Thr Lys His Val Ala Gln Ile Leu Asp Ser Arg Met
                965                 970                 975

Asn Thr Lys Tyr Asp Glu Asn Asp Lys Leu Ile Arg Glu Val Lys Val
                980                 985                 990

Ile Thr Leu Lys Ser Lys Leu Val  Ser Asp Phe Arg Lys  Asp Phe Gln
                995                 1000                1005

Phe Tyr  Lys Val Arg Glu Ile  Asn Asn Tyr His His  Ala His Asp
     1010                1015                1020

Ala Tyr  Leu Asn Ala Val Val  Gly Thr Ala Leu Ile  Lys Lys Tyr
```

```
            1025                1030                1035

Pro Lys Leu Glu Ser Glu Phe Val Tyr Gly Asp Tyr Lys Val Tyr
            1040                1045                1050

Asp Val Arg Lys Met Ile Ala Lys Ser Glu Gln Glu Ile Gly Lys
            1055                1060                1065

Ala Thr Ala Lys Tyr Phe Phe Tyr Ser Asn Ile Met Asn Phe Phe
            1070                1075                1080

Lys Thr Glu Ile Thr Leu Ala Asn Gly Glu Ile Arg Lys Arg Pro
            1085                1090                1095

Leu Ile Glu Thr Asn Gly Glu Thr Gly Glu Ile Val Trp Asp Lys
            1100                1105                1110

Gly Arg Asp Phe Ala Thr Val Arg Lys Val Leu Ser Met Pro Gln
            1115                1120                1125

Val Asn Ile Val Lys Lys Thr Glu Val Gln Thr Gly Gly Phe Ser
            1130                1135                1140

Lys Glu Ser Ile Leu Pro Lys Arg Asn Ser Asp Lys Leu Ile Ala
            1145                1150                1155

Arg Lys Lys Asp Trp Asp Pro Lys Lys Tyr Gly Gly Phe Asp Ser
            1160                1165                1170

Pro Thr Val Ala Tyr Ser Val Leu Val Val Ala Lys Val Glu Lys
            1175                1180                1185

Gly Lys Ser Lys Lys Leu Lys Ser Val Lys Glu Leu Leu Gly Ile
            1190                1195                1200

Thr Ile Met Glu Arg Ser Ser Phe Glu Lys Asn Pro Ile Asp Phe
            1205                1210                1215

Leu Glu Ala Lys Gly Tyr Lys Glu Val Lys Lys Asp Leu Ile Ile
            1220                1225                1230

Lys Leu Pro Lys Tyr Ser Leu Phe Glu Leu Glu Asn Gly Arg Lys
            1235                1240                1245

Arg Met Leu Ala Ser Ala Gly Glu Leu Gln Lys Gly Asn Glu Leu
            1250                1255                1260

Ala Leu Pro Ser Lys Tyr Val Asn Phe Leu Tyr Leu Ala Ser His
            1265                1270                1275

Tyr Glu Lys Leu Lys Gly Ser Pro Glu Asp Asn Glu Gln Lys Gln
            1280                1285                1290

Leu Phe Val Glu Gln His Lys His Tyr Leu Asp Glu Ile Ile Glu
            1295                1300                1305

Gln Ile Ser Glu Phe Ser Lys Arg Val Ile Leu Ala Asp Ala Asn
            1310                1315                1320

Leu Asp Lys Val Leu Ser Ala Tyr Asn Lys His Arg Asp Lys Pro
            1325                1330                1335

Ile Arg Glu Gln Ala Glu Asn Ile Ile His Leu Phe Thr Leu Thr
            1340                1345                1350

Asn Leu Gly Ala Pro Ala Ala Phe Lys Tyr Phe Asp Thr Thr Ile
            1355                1360                1365

Asp Arg Lys Arg Tyr Thr Ser Thr Lys Glu Val Leu Asp Ala Thr
            1370                1375                1380

Leu Ile His Gln Ser Ile Thr Gly Leu Tyr Glu Thr Arg Ile Asp
            1385                1390                1395

Leu Ser Gln Leu Gly Gly Asp Pro Glu Phe Met Ala Met Glu Ala
            1400                1405                1410

Pro Gly Ile Arg Met Ala Leu Glu Gly Leu Arg Lys Lys Tyr Lys
            1415                1420                1425
```

```
Thr Arg Gln Glu Leu Val Lys Ala Leu Thr Pro Lys Arg Arg Ser
    1430            1435            1440

Ile His Leu Asn Ser Asn Gly His Ser Asn Gly Thr Pro Cys Ser
    1445            1450            1455

Asn Ala Asp Val Leu Ala His Ile Lys His Phe Leu Ser Leu Ala
    1460            1465            1470

Ala Asn Ser Leu Glu Gln His Gln Gln Pro Ile Ser Ile Val Phe
    1475            1480            1485

Gln Asn Lys Lys Lys Gly Asp Thr Ser Ser Pro Asp Ile His
    1490            1495            1500

Thr Thr Leu Asp Phe Pro Leu Asn Gly Pro His Leu Cys Thr His
    1505            1510            1515

Gln Phe Lys Leu Lys Arg Cys Ala Ile Leu Leu Asn Leu Leu Lys
    1520            1525            1530

Val Val Met Glu Lys Leu Pro Leu Gly Lys Asn Thr Thr Val Arg
    1535            1540            1545

Asp Ile Phe Tyr Ser Asn Val Glu Leu Phe Gln Arg Gln Ala Asn
    1550            1555            1560

Val Val Gln Trp Leu Asp Val Ile Arg Phe Asn Phe Lys Leu Ser
    1565            1570            1575

Pro Arg Lys Ser Leu Asn Ile Ile Pro Ala Gln Lys Gly Leu Val
    1580            1585            1590

Tyr Ser Pro Phe Pro Ile Asp Ile Tyr Asp Asn Ile Leu Thr Cys
    1595            1600            1605

Glu Asn Glu Pro Lys Met Gln Lys Gln Thr Ile Phe Pro Gly Lys
    1610            1615            1620

Pro Cys Leu Ile Pro Phe Phe Gln Asp Asp Ala Val Ile Lys Leu
    1625            1630            1635

Gly Thr Thr Ser Met Cys Asn Ile Val Ile Val Glu Lys Glu Ala
    1640            1645            1650

Val Phe Thr Lys Leu Val Asn Asn Tyr His Lys Leu Ser Thr Asn
    1655            1660            1665

Thr Met Leu Ile Thr Gly Lys Gly Phe Pro Asp Phe Leu Thr Arg
    1670            1675            1680

Leu Phe Leu Lys Lys Leu Glu Gln Tyr Cys Ser Lys Leu Ile Ser
    1685            1690            1695

Asp Cys Ser Ile Phe Thr Asp Ala Asp Pro Tyr Gly Ile Ser Ile
    1700            1705            1710

Ala Leu Asn Tyr Thr His Ser Asn Glu Arg Asn Ala Tyr Ile Cys
    1715            1720            1725

Thr Met Ala Asn Tyr Lys Gly Ile Arg Ile Thr Gln Val Leu Ala
    1730            1735            1740

Gln Asn Asn Glu Val His Asn Lys Ser Ile Gln Leu Leu Ser Leu
    1745            1750            1755

Asn Gln Arg Asp Tyr Ser Leu Ala Lys Asn Leu Ile Ala Ser Leu
    1760            1765            1770

Thr Ala Asn Ser Trp Asp Ile Ala Thr Ser Pro Leu Lys Asn Val
    1775            1780            1785

Ile Ile Glu Cys Gln Arg Glu Ile Phe Phe Gln Lys Lys Ala Glu
    1790            1795            1800

Met Asn Glu Ile Asp Ala Arg Ile Phe Glu Tyr Lys Asp Tyr Lys
    1805            1810            1815
```

-continued

```
Asp Asp  Asp Asp Lys Asp Tyr  Lys Asp Asp Asp  Lys Asp Tyr
   1820              1825              1830

Lys Asp  Asp Asp Asp Lys
   1835

<210> SEQ ID NO 7
<211> LENGTH: 1839
<212> TYPE: PRT
<213> ORGANISM: Artificial Sequence
<220> FEATURE:
<223> OTHER INFORMATION: Fusion protein comprising the Cas9*-Spo11
      construction

<400> SEQUENCE: 7

Met Gly Lys Pro Ile Pro Asn Pro Leu Leu Gly Leu Asp Ser Thr Gly
1               5                   10                  15

Gly Met Ala Pro Lys Lys Arg Lys Val Asp Gly Gly Ile His
            20                  25                  30

Gly Val Pro Ala Ala Met Asp Lys Lys Tyr Ser Ile Gly Leu Ala Ile
            35                  40                  45

Gly Thr Asn Ser Val Gly Trp Ala Val Ile Thr Asp Glu Tyr Lys Val
        50                  55                  60

Pro Ser Lys Lys Phe Lys Val Leu Gly Asn Thr Asp Arg His Ser Ile
65                  70                  75                  80

Lys Lys Asn Leu Ile Gly Ala Leu Leu Phe Asp Ser Gly Glu Thr Ala
                85                  90                  95

Glu Ala Thr Arg Leu Lys Arg Thr Ala Arg Arg Arg Tyr Thr Arg Arg
            100                 105                 110

Lys Asn Arg Ile Cys Tyr Leu Gln Glu Ile Phe Ser Asn Glu Met Ala
        115                 120                 125

Lys Val Asp Asp Ser Phe Phe His Arg Leu Glu Glu Ser Phe Leu Val
    130                 135                 140

Glu Glu Asp Lys Lys His Glu Arg His Pro Ile Phe Gly Asn Ile Val
145                 150                 155                 160

Asp Glu Val Ala Tyr His Glu Lys Tyr Pro Thr Ile Tyr His Leu Arg
                165                 170                 175

Lys Lys Leu Val Asp Ser Thr Asp Lys Ala Asp Leu Arg Leu Ile Tyr
            180                 185                 190

Leu Ala Leu Ala His Met Ile Lys Phe Arg Gly His Phe Leu Ile Glu
        195                 200                 205

Gly Asp Leu Asn Pro Asp Asn Ser Asp Val Asp Lys Leu Phe Ile Gln
    210                 215                 220

Leu Val Gln Thr Tyr Asn Gln Leu Phe Glu Glu Asn Pro Ile Asn Ala
225                 230                 235                 240

Ser Gly Val Asp Ala Lys Ala Ile Leu Ser Ala Arg Leu Ser Lys Ser
                245                 250                 255

Arg Arg Leu Glu Asn Leu Ile Ala Gln Leu Pro Gly Glu Lys Lys Asn
            260                 265                 270

Gly Leu Phe Gly Asn Leu Ile Ala Leu Ser Leu Gly Leu Thr Pro Asn
        275                 280                 285

Phe Lys Ser Asn Phe Asp Leu Ala Glu Asp Ala Lys Leu Gln Leu Ser
    290                 295                 300

Lys Asp Thr Tyr Asp Asp Asp Leu Asp Asn Leu Leu Ala Gln Ile Gly
305                 310                 315                 320

Asp Gln Tyr Ala Asp Leu Phe Leu Ala Ala Lys Asn Leu Ser Asp Ala
                325                 330                 335
```

```
Ile Leu Leu Ser Asp Ile Leu Arg Val Asn Thr Glu Ile Thr Lys Ala
            340                 345                 350

Pro Leu Ser Ala Ser Met Ile Lys Arg Tyr Asp Glu His His Gln Asp
            355                 360                 365

Leu Thr Leu Leu Lys Ala Leu Val Arg Gln Gln Leu Pro Glu Lys Tyr
    370                 375                 380

Lys Glu Ile Phe Phe Asp Gln Ser Lys Asn Gly Tyr Ala Gly Tyr Ile
385                 390                 395                 400

Asp Gly Gly Ala Ser Gln Glu Glu Phe Tyr Lys Phe Ile Lys Pro Ile
                405                 410                 415

Leu Glu Lys Met Asp Gly Thr Glu Glu Leu Leu Val Lys Leu Asn Arg
            420                 425                 430

Glu Asp Leu Leu Arg Lys Gln Arg Thr Phe Asp Asn Gly Ser Ile Pro
        435                 440                 445

His Gln Ile His Leu Gly Glu Leu His Ala Ile Leu Arg Arg Gln Glu
    450                 455                 460

Asp Phe Tyr Pro Phe Leu Lys Asp Asn Arg Glu Lys Ile Glu Lys Ile
465                 470                 475                 480

Leu Thr Phe Arg Ile Pro Tyr Tyr Val Gly Pro Leu Ala Arg Gly Asn
                485                 490                 495

Ser Arg Phe Ala Trp Met Thr Arg Lys Ser Glu Glu Thr Ile Thr Pro
            500                 505                 510

Trp Asn Phe Glu Glu Val Val Asp Lys Gly Ala Ser Ala Gln Ser Phe
        515                 520                 525

Ile Glu Arg Met Thr Asn Phe Asp Lys Asn Leu Pro Asn Glu Lys Val
    530                 535                 540

Leu Pro Lys His Ser Leu Leu Tyr Glu Tyr Phe Thr Val Tyr Asn Glu
545                 550                 555                 560

Leu Thr Lys Val Lys Tyr Val Thr Glu Gly Met Arg Lys Pro Ala Phe
                565                 570                 575

Leu Ser Gly Glu Gln Lys Lys Ala Ile Val Asp Leu Leu Phe Lys Thr
            580                 585                 590

Asn Arg Lys Val Thr Val Lys Gln Leu Lys Glu Asp Tyr Phe Lys Lys
        595                 600                 605

Ile Glu Cys Phe Asp Ser Val Glu Ile Ser Gly Val Glu Asp Arg Phe
    610                 615                 620

Asn Ala Ser Leu Gly Thr Tyr His Asp Leu Leu Lys Ile Ile Lys Asp
625                 630                 635                 640

Lys Asp Phe Leu Asp Asn Glu Glu Asn Glu Asp Ile Leu Glu Asp Ile
                645                 650                 655

Val Leu Thr Leu Thr Leu Phe Glu Asp Arg Glu Met Ile Glu Glu Arg
            660                 665                 670

Leu Lys Thr Tyr Ala His Leu Phe Asp Asp Lys Val Met Lys Gln Leu
        675                 680                 685

Lys Arg Arg Arg Tyr Thr Gly Trp Gly Arg Leu Ser Arg Lys Leu Ile
    690                 695                 700

Asn Gly Ile Arg Asp Lys Gln Ser Gly Lys Thr Ile Leu Asp Phe Leu
705                 710                 715                 720

Lys Ser Asp Gly Phe Ala Asn Arg Asn Phe Met Gln Leu Ile His Asp
                725                 730                 735

Asp Ser Leu Thr Phe Lys Glu Asp Ile Gln Lys Ala Gln Val Ser Gly
            740                 745                 750
```

-continued

Gln Gly Asp Ser Leu His Glu His Ile Ala Asn Leu Ala Gly Ser Pro
            755                 760                 765

Ala Ile Lys Lys Gly Ile Leu Gln Thr Val Lys Val Val Asp Glu Leu
770                 775                 780

Val Lys Val Met Gly Arg His Lys Pro Glu Asn Ile Val Ile Glu Met
785                 790                 795                 800

Ala Arg Glu Asn Gln Thr Thr Gln Lys Gly Gln Lys Asn Ser Arg Glu
            805                 810                 815

Arg Met Lys Arg Ile Glu Glu Gly Ile Lys Glu Leu Gly Ser Gln Ile
            820                 825                 830

Leu Lys Glu His Pro Val Glu Asn Thr Gln Leu Gln Asn Glu Lys Leu
            835                 840                 845

Tyr Leu Tyr Tyr Leu Gln Asn Gly Arg Asp Met Tyr Val Asp Gln Glu
850                 855                 860

Leu Asp Ile Asn Arg Leu Ser Asp Tyr Asp Val Asp Ala Ile Val Pro
865                 870                 875                 880

Gln Ser Phe Leu Lys Asp Asp Ser Ile Asp Asn Lys Val Leu Thr Arg
            885                 890                 895

Ser Asp Lys Asn Arg Gly Lys Ser Asp Asn Val Pro Ser Glu Glu Val
            900                 905                 910

Val Lys Lys Met Lys Asn Tyr Trp Arg Gln Leu Leu Asn Ala Lys Leu
            915                 920                 925

Ile Thr Gln Arg Lys Phe Asp Asn Leu Thr Lys Ala Glu Arg Gly Gly
            930                 935                 940

Leu Ser Glu Leu Asp Lys Ala Gly Phe Ile Lys Arg Gln Leu Val Glu
945                 950                 955                 960

Thr Arg Gln Ile Thr Lys His Val Ala Gln Ile Leu Asp Ser Arg Met
            965                 970                 975

Asn Thr Lys Tyr Asp Glu Asn Asp Lys Leu Ile Arg Glu Val Lys Val
            980                 985                 990

Ile Thr Leu Lys Ser Lys Leu Val Ser Asp Phe Arg Lys Asp Phe Gln
            995                 1000                1005

Phe Tyr Lys Val Arg Glu Ile Asn Asn Tyr His His Ala His Asp
        1010                1015                1020

Ala Tyr Leu Asn Ala Val Val Gly Thr Ala Leu Ile Lys Lys Tyr
        1025                1030                1035

Pro Lys Leu Glu Ser Glu Phe Val Tyr Gly Asp Tyr Lys Val Tyr
        1040                1045                1050

Asp Val Arg Lys Met Ile Ala Lys Ser Glu Gln Glu Ile Gly Lys
        1055                1060                1065

Ala Thr Ala Lys Tyr Phe Phe Tyr Ser Asn Ile Met Asn Phe Phe
        1070                1075                1080

Lys Thr Glu Ile Thr Leu Ala Asn Gly Glu Ile Arg Lys Arg Pro
        1085                1090                1095

Leu Ile Glu Thr Asn Gly Glu Thr Gly Glu Ile Val Trp Asp Lys
        1100                1105                1110

Gly Arg Asp Phe Ala Thr Val Arg Lys Val Leu Ser Met Pro Gln
        1115                1120                1125

Val Asn Ile Val Lys Lys Thr Glu Val Gln Thr Gly Gly Phe Ser
        1130                1135                1140

Lys Glu Ser Ile Leu Pro Lys Arg Asn Ser Asp Lys Leu Ile Ala
        1145                1150                1155

Arg Lys Lys Asp Trp Asp Pro Lys Lys Tyr Gly Gly Phe Asp Ser

-continued

```
            1160                1165                1170
Pro Thr Val Ala Tyr Ser Val Leu Val Val Ala Lys Val Glu Lys
        1175                1180                1185
Gly Lys Ser Lys Lys Leu Lys Ser Val Lys Glu Leu Leu Gly Ile
        1190                1195                1200
Thr Ile Met Glu Arg Ser Ser Phe Glu Lys Asn Pro Ile Asp Phe
        1205                1210                1215
Leu Glu Ala Lys Gly Tyr Lys Glu Val Lys Lys Asp Leu Ile Ile
        1220                1225                1230
Lys Leu Pro Lys Tyr Ser Leu Phe Glu Leu Glu Asn Gly Arg Lys
        1235                1240                1245
Arg Met Leu Ala Ser Ala Gly Glu Leu Gln Lys Gly Asn Glu Leu
        1250                1255                1260
Ala Leu Pro Ser Lys Tyr Val Asn Phe Leu Tyr Leu Ala Ser His
        1265                1270                1275
Tyr Glu Lys Leu Lys Gly Ser Pro Glu Asp Asn Glu Gln Lys Gln
        1280                1285                1290
Leu Phe Val Glu Gln His Lys His Tyr Leu Asp Glu Ile Ile Glu
        1295                1300                1305
Gln Ile Ser Glu Phe Ser Lys Arg Val Ile Leu Ala Asp Ala Asn
        1310                1315                1320
Leu Asp Lys Val Leu Ser Ala Tyr Asn Lys His Arg Asp Lys Pro
        1325                1330                1335
Ile Arg Glu Gln Ala Glu Asn Ile Ile His Leu Phe Thr Leu Thr
        1340                1345                1350
Asn Leu Gly Ala Pro Ala Ala Phe Lys Tyr Phe Asp Thr Thr Ile
        1355                1360                1365
Asp Arg Lys Arg Tyr Thr Ser Thr Lys Glu Val Leu Asp Ala Thr
        1370                1375                1380
Leu Ile His Gln Ser Ile Thr Gly Leu Tyr Glu Thr Arg Ile Asp
        1385                1390                1395
Leu Ser Gln Leu Gly Gly Asp Pro Glu Phe Met Ala Met Glu Ala
        1400                1405                1410
Pro Gly Ile Arg Met Ala Leu Glu Gly Leu Arg Lys Lys Tyr Lys
        1415                1420                1425
Thr Arg Gln Glu Leu Val Lys Ala Leu Thr Pro Lys Arg Arg Ser
        1430                1435                1440
Ile His Leu Asn Ser Asn Gly His Ser Asn Gly Thr Pro Cys Ser
        1445                1450                1455
Asn Ala Asp Val Leu Ala His Ile Lys His Phe Leu Ser Leu Ala
        1460                1465                1470
Ala Asn Ser Leu Glu Gln His Gln Gln Pro Ile Ser Ile Val Phe
        1475                1480                1485
Gln Asn Lys Lys Lys Gly Asp Thr Ser Ser Pro Asp Ile His
        1490                1495                1500
Thr Thr Leu Asp Phe Pro Leu Asn Gly Pro His Leu Cys Thr His
        1505                1510                1515
Gln Phe Lys Leu Lys Arg Cys Ala Ile Leu Leu Asn Leu Leu Lys
        1520                1525                1530
Val Val Met Glu Lys Leu Pro Leu Gly Lys Asn Thr Thr Val Arg
        1535                1540                1545
Asp Ile Phe Tyr Ser Asn Val Glu Leu Phe Gln Arg Gln Ala Asn
        1550                1555                1560
```

Val Val Gln Trp Leu Asp Val Ile Arg Phe Asn Phe Lys Leu Ser
1565                1570                1575

Pro Arg Lys Ser Leu Asn Ile Ile Pro Ala Gln Lys Gly Leu Val
1580                1585                1590

Tyr Ser Pro Phe Pro Ile Asp Ile Tyr Asp Asn Ile Leu Thr Cys
1595                1600                1605

Glu Asn Glu Pro Lys Met Gln Lys Gln Thr Ile Phe Pro Gly Lys
1610                1615                1620

Pro Cys Leu Ile Pro Phe Phe Gln Asp Asp Ala Val Ile Lys Leu
1625                1630                1635

Gly Thr Thr Ser Met Cys Asn Ile Val Ile Val Glu Lys Glu Ala
1640                1645                1650

Val Phe Thr Lys Leu Val Asn Asn Tyr His Lys Leu Ser Thr Asn
1655                1660                1665

Thr Met Leu Ile Thr Gly Lys Gly Phe Pro Asp Phe Leu Thr Arg
1670                1675                1680

Leu Phe Leu Lys Lys Leu Glu Gln Tyr Cys Ser Lys Leu Ile Ser
1685                1690                1695

Asp Cys Ser Ile Phe Thr Asp Ala Asp Pro Tyr Gly Ile Ser Ile
1700                1705                1710

Ala Leu Asn Tyr Thr His Ser Asn Glu Arg Asn Ala Tyr Ile Cys
1715                1720                1725

Thr Met Ala Asn Tyr Lys Gly Ile Arg Ile Thr Gln Val Leu Ala
1730                1735                1740

Gln Asn Asn Glu Val His Asn Lys Ser Ile Gln Leu Leu Ser Leu
1745                1750                1755

Asn Gln Arg Asp Tyr Ser Leu Ala Lys Asn Leu Ile Ala Ser Leu
1760                1765                1770

Thr Ala Asn Ser Trp Asp Ile Ala Thr Ser Pro Leu Lys Asn Val
1775                1780                1785

Ile Ile Glu Cys Gln Arg Glu Ile Phe Phe Gln Lys Lys Ala Glu
1790                1795                1800

Met Asn Glu Ile Asp Ala Arg Ile Phe Glu Tyr Lys Asp Tyr Lys
1805                1810                1815

Asp Asp Asp Asp Lys Asp Tyr Lys Asp Asp Asp Lys Asp Tyr
1820                1825                1830

Lys Asp Asp Asp Asp Lys
1835

<210> SEQ ID NO 8
<211> LENGTH: 1368
<212> TYPE: PRT
<213> ORGANISM: Streptococcus pyogenes

<400> SEQUENCE: 8

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys

```
               65                  70                  75                  80
          Tyr Leu Gln Glu Ile Phe Ser Asn Glu Met Ala Lys Val Asp Asp Ser
                              85                  90                  95
          Phe Phe His Arg Leu Glu Glu Ser Phe Leu Val Glu Glu Asp Lys Lys
                             100                 105                 110
          His Glu Arg His Pro Ile Phe Gly Asn Ile Val Asp Glu Val Ala Tyr
                             115                 120                 125
          His Glu Lys Tyr Pro Thr Ile Tyr His Leu Arg Lys Lys Leu Val Asp
                             130                 135                 140
          Ser Thr Asp Lys Ala Asp Leu Arg Leu Ile Tyr Leu Ala Leu Ala His
          145                 150                 155                 160
          Met Ile Lys Phe Arg Gly His Phe Leu Ile Glu Gly Asp Leu Asn Pro
                             165                 170                 175
          Asp Asn Ser Asp Val Asp Lys Leu Phe Ile Gln Leu Val Gln Thr Tyr
                             180                 185                 190
          Asn Gln Leu Phe Glu Glu Asn Pro Ile Asn Ala Ser Gly Val Asp Ala
                             195                 200                 205
          Lys Ala Ile Leu Ser Ala Arg Leu Ser Lys Ser Arg Arg Leu Glu Asn
                             210                 215                 220
          Leu Ile Ala Gln Leu Pro Gly Glu Lys Lys Asn Gly Leu Phe Gly Asn
          225                 230                 235                 240
          Leu Ile Ala Leu Ser Leu Gly Leu Thr Pro Asn Phe Lys Ser Asn Phe
                             245                 250                 255
          Asp Leu Ala Glu Asp Ala Lys Leu Gln Leu Ser Lys Asp Thr Tyr Asp
                             260                 265                 270
          Asp Asp Leu Asp Asn Leu Leu Ala Gln Ile Gly Asp Gln Tyr Ala Asp
                             275                 280                 285
          Leu Phe Leu Ala Ala Lys Asn Leu Ser Asp Ala Ile Leu Leu Ser Asp
                             290                 295                 300
          Ile Leu Arg Val Asn Thr Glu Ile Thr Lys Ala Pro Leu Ser Ala Ser
          305                 310                 315                 320
          Met Ile Lys Arg Tyr Asp Glu His His Gln Asp Leu Thr Leu Leu Lys
                             325                 330                 335
          Ala Leu Val Arg Gln Gln Leu Pro Glu Lys Tyr Lys Glu Ile Phe Phe
                             340                 345                 350
          Asp Gln Ser Lys Asn Gly Tyr Ala Gly Tyr Ile Asp Gly Gly Ala Ser
                             355                 360                 365
          Gln Glu Glu Phe Tyr Lys Phe Ile Lys Pro Ile Leu Glu Lys Met Asp
                             370                 375                 380
          Gly Thr Glu Glu Leu Leu Val Lys Leu Asn Arg Glu Asp Leu Leu Arg
          385                 390                 395                 400
          Lys Gln Arg Thr Phe Asp Asn Gly Ser Ile Pro His Gln Ile His Leu
                             405                 410                 415
          Gly Glu Leu His Ala Ile Leu Arg Arg Gln Glu Asp Phe Tyr Pro Phe
                             420                 425                 430
          Leu Lys Asp Asn Arg Glu Lys Ile Glu Lys Ile Leu Thr Phe Arg Ile
                             435                 440                 445
          Pro Tyr Tyr Val Gly Pro Leu Ala Arg Gly Asn Ser Arg Phe Ala Trp
                             450                 455                 460
          Met Thr Arg Lys Ser Glu Glu Thr Ile Thr Pro Trp Asn Phe Glu Glu
          465                 470                 475                 480
          Val Val Asp Lys Gly Ala Ser Ala Gln Ser Phe Ile Glu Arg Met Thr
                             485                 490                 495
```

```
Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910
```

-continued

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
        980                 985                 990

Val Gly Thr Ala Leu Ile Lys Lys Tyr Pro Lys Leu Glu Ser Glu Phe
    995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala

```
                    1310               1315              1320

Phe Lys Tyr Phe Asp Thr Thr  Ile Asp Arg Lys Arg  Tyr Thr Ser
    1325              1330              1335

Thr Lys Glu Val Leu Asp Ala  Thr Leu Ile His Gln  Ser Ile Thr
    1340              1345              1350

Gly Leu Tyr Glu Thr Arg Ile  Asp Leu Ser Gln Leu  Gly Gly Asp
    1355              1360              1365

<210> SEQ ID NO 9
<211> LENGTH: 398
<212> TYPE: PRT
<213> ORGANISM: Saccharomyces cerevisiae

<400> SEQUENCE: 9

Met Ala Leu Glu Gly Leu Arg Lys Lys Tyr Lys Thr Arg Gln Glu Leu
1               5                   10                  15

Val Lys Ala Leu Thr Pro Lys Arg Arg Ser Ile His Leu Asn Ser Asn
                20                  25                  30

Gly His Ser Asn Gly Thr Pro Cys Ser Asn Ala Asp Val Leu Ala His
            35                  40                  45

Ile Lys His Phe Leu Ser Leu Ala Ala Asn Ser Leu Glu Gln His Gln
50                  55                  60

Gln Pro Ile Ser Ile Val Phe Gln Asn Lys Lys Lys Gly Asp Thr
65                  70                  75                  80

Ser Ser Pro Asp Ile His Thr Thr Leu Asp Phe Pro Leu Asn Gly Pro
                85                  90                  95

His Leu Cys Thr His Gln Phe Lys Leu Lys Arg Cys Ala Ile Leu Leu
            100                 105                 110

Asn Leu Leu Lys Val Val Met Glu Lys Leu Pro Leu Gly Lys Asn Thr
        115                 120                 125

Thr Val Arg Asp Ile Phe Tyr Ser Asn Val Glu Leu Phe Gln Arg Gln
    130                 135                 140

Ala Asn Val Val Gln Trp Leu Asp Val Ile Arg Phe Asn Phe Lys Leu
145                 150                 155                 160

Ser Pro Arg Lys Ser Leu Asn Ile Ile Pro Ala Gln Lys Gly Leu Val
                165                 170                 175

Tyr Ser Pro Phe Pro Ile Asp Ile Tyr Asp Asn Ile Leu Thr Cys Glu
            180                 185                 190

Asn Glu Pro Lys Met Gln Lys Gln Thr Ile Phe Pro Gly Lys Pro Cys
        195                 200                 205

Leu Ile Pro Phe Phe Gln Asp Ala Val Ile Lys Leu Gly Thr Thr
    210                 215                 220

Ser Met Cys Asn Ile Val Ile Val Glu Lys Glu Ala Val Phe Thr Lys
225                 230                 235                 240

Leu Val Asn Asn Tyr His Lys Leu Ser Thr Asn Thr Met Leu Ile Thr
                245                 250                 255

Gly Lys Gly Phe Pro Asp Phe Leu Thr Arg Leu Phe Leu Lys Lys Leu
            260                 265                 270

Glu Gln Tyr Cys Ser Lys Leu Ile Ser Asp Cys Ser Ile Phe Thr Asp
        275                 280                 285

Ala Asp Pro Tyr Gly Ile Ser Ile Ala Leu Asn Tyr Thr His Ser Asn
    290                 295                 300

Glu Arg Asn Ala Tyr Ile Cys Thr Met Ala Asn Tyr Lys Gly Ile Arg
305                 310                 315                 320
```

| | | | | | | | | | | | |
|---|---|---|---|---|---|---|---|---|---|---|---|
| Ile | Thr | Gln | Val | Leu | Ala | Gln | Asn | Asn | Glu | Val | His | Asn | Lys | Ser | Ile |
| | | | | 325 | | | | 330 | | | | 335 | | | |
| Gln | Leu | Leu | Ser | Leu | Asn | Gln | Arg | Asp | Tyr | Ser | Leu | Ala | Lys | Asn | Leu |
| | | | 340 | | | | | 345 | | | | | 350 | | |
| Ile | Ala | Ser | Leu | Thr | Ala | Asn | Ser | Trp | Asp | Ile | Ala | Thr | Ser | Pro | Leu |
| | | 355 | | | | | 360 | | | | | 365 | | | |
| Lys | Asn | Val | Ile | Ile | Glu | Cys | Gln | Arg | Glu | Ile | Phe | Phe | Gln | Lys | Lys |
| 370 | | | | | 375 | | | | 380 | | | | | | |
| Ala | Glu | Met | Asn | Glu | Ile | Asp | Ala | Arg | Ile | Phe | Glu | Tyr | Lys | | |
| 385 | | | | 390 | | | | | 395 | | | | | | |

```
<210> SEQ ID NO 10
<211> LENGTH: 102
<212> TYPE: DNA
<213> ORGANISM: Artificial Sequence
<220> FEATURE:
<223> OTHER INFORMATION: UAS1 guide RNA targeting the 5' coding region
      of the YCR048W gene

<400> SEQUENCE: 10
cacacctgaa gagcaagtct gttttagagc tagaaatagc aagttaaaat aaggctagtc      60
cgttatcaac ttgaaaaagt ggcaccgagt cggtgctttt tt                        102

<210> SEQ ID NO 11
<211> LENGTH: 102
<212> TYPE: DNA
<213> ORGANISM: Artificial Sequence
<220> FEATURE:
<223> OTHER INFORMATION: UAS2 guide RNA targeting the 3' coding region
      of the YCR048W gene

<400> SEQUENCE: 11
ttccacaaca cgcccacctt gttttagagc tagaaatagc aagttaaaat aaggctagtc      60
cgttatcaac ttgaaaaagt ggcaccgagt cggtgctttt tt                        102

<210> SEQ ID NO 12
<211> LENGTH: 102
<212> TYPE: DNA
<213> ORGANISM: Artificial Sequence
<220> FEATURE:
<223> OTHER INFORMATION: UAS D/E guide RNA targeting the GAL2 gene
      promoter site

<400> SEQUENCE: 12
gatcactccg aaccgagatt gttttagagc tagaaatagc aagttaaaat aaggctagtc      60
cgttatcaac ttgaaaaagt ggcaccgagt cggtgctttt tt                        102

<210> SEQ ID NO 13
<211> LENGTH: 102
<212> TYPE: DNA
<213> ORGANISM: Artificial Sequence
<220> FEATURE:
<223> OTHER INFORMATION: SWC3 guide RNA targeting the SWC3 gene coding
      region

<400> SEQUENCE: 13
tgcgattgtg taatgagtgg gttttagagc tagaaatagc aagttaaaat aaggctagtc      60
cgttatcaac ttgaaaaagt ggcaccgagt cggtgctttt tt                        102

<210> SEQ ID NO 14
<211> LENGTH: 102
<212> TYPE: DNA
```

<213> ORGANISM: Artificial Sequence
<220> FEATURE:
<223> OTHER INFORMATION: UAS A guide RNA targeting the GAL2 promoter
      site

<400> SEQUENCE: 14
caattcggaa agcttccttc gttttagagc tagaaatagc aagttaaaat aaggctagtc      60
cgttatcaac ttgaaaaagt ggcaccgagt cggtgctttt tt                        102

<210> SEQ ID NO 15
<211> LENGTH: 102
<212> TYPE: DNA
<213> ORGANISM: Artificial Sequence
<220> FEATURE:
<223> OTHER INFORMATION: UAS B guide RNA targeting the GAL2 gene
      promoter site

<400> SEQUENCE: 15
ttgcctcagg aaggcaccgg gttttagagc tagaaatagc aagttaaaat aaggctagtc      60
cgttatcaac ttgaaaaagt ggcaccgagt cggtgctttt tt                        102

<210> SEQ ID NO 16
<211> LENGTH: 102
<212> TYPE: DNA
<213> ORGANISM: Artificial Sequence
<220> FEATURE:
<223> OTHER INFORMATION: PUT4 guide RNA targeting the PUT4 gene coding
      region

<400> SEQUENCE: 16
gttttgaatt ccgatcacaa gttttagagc tagaaatagc aagttaaaat aaggctagtc      60
cgttatcaac ttgaaaaagt ggcaccgagt cggtgctttt tt                        102

<210> SEQ ID NO 17
<211> LENGTH: 36
<212> TYPE: DNA
<213> ORGANISM: Artificial Sequence
<220> FEATURE:
<223> OTHER INFORMATION: linker of the dCas9-SPO11 construction for
      transforming rice cells

<400> SEQUENCE: 17
ccggaattta tggccatgga ggccccgggg atccgt                               36

<210> SEQ ID NO 18
<211> LENGTH: 24
<212> TYPE: DNA
<213> ORGANISM: Artificial Sequence
<220> FEATURE:
<223> OTHER INFORMATION: Linker of the dCas9-SPO11 construction for
      transforming rice cells

<400> SEQUENCE: 18
ggtattcatg gagttcctgc tgcg                                            24

METHOD FOR INDUCING TARGETED MEIOTIC RECOMBINATIONS

CROSS-REFERENCE TO RELATED APPLICATION

This application is the U.S. national stage application of International Patent Application No. PCT/EP2016/052000, filed Jan. 29, 2016.

The Sequence Listing for this application is labeled "Seq-List.txt" which was created on Jul. 3, 2017 and is 84 KB. The entire content of the sequence listing is incorporated herein by reference in its entirety.

The present invention falls within the field of the eukaryotes, more particularly within the field of microbiology. It concerns notably a method for improving or modifying a yeast strain by inducing targeted meiotic recombinations.

TECHNOLOGICAL BACKGROUND OF THE INVENTION

Yeasts are used in a wide variety of industries. Due to the harmlessness of a large number of species, yeasts are especially used in the food industry as a fermentation agent in baking, brewing, winemaking or distilling, or as extracts for nutritional elements or flavorings. They may also be used in the industrial production of bioethanol or of molecules of interest such as vitamins, antibiotics, vaccines, enzymes or steroid hormones, or in cellulosic material degradation processes.

The diversity of the industrial applications of yeasts means that there is a constant demand for yeast strains having improved characteristics, or at least that are suitable for a new usage or new culture conditions.

To obtain a strain having a specific characteristic, a person skilled in the art may use sexual reproduction by crossing two parental strains having characteristics of interest and by selecting a hybrid strain providing the desired combination of parental characteristics. This method is however random and the selection step may be costly in terms of time.

Alternatively, the strain may also be genetically modified by a recombinant DNA technique. This modification may nevertheless act to curb its use, whether for legal, health or environmental reasons.

A third alternative consists in causing a reassortment of paternal and maternal alleles in the genome, during meiotic recombination. Meiotic recombination is an exchange of DNA between homologous chromosomes during meiosis. It is initiated by the formation of double-strand breaks in one or the other homologous chromatid, followed by repair of these breaks, using as matrix a chromatid of the homologous chromosome. However, meiotic recombinations have the disadvantage of being random and nonuniform. Indeed, the double-strand break sites at the origin of these recombinations are not distributed homogeneously in the genome. So-called 'hotspot' regions of the chromosome, where the recombination frequency is high, can thus be distinguished from so-called 'cold' regions of the chromosome, where the recombination frequency may be up to 100 times lower.

Spo11 is the protein that catalyzes double-strand breaks during meiosis. It acts as a dimer in cooperation with numerous partners. At present, the factors determining the choice of double strand break sites by Spo11 and its partners remain poorly understood.

Controlling the formation of double-strand breaks and, in fact, meiotic recombinations, is crucial to the development of genetic engineering techniques. It was recently shown that it is possible to modify double-strand break formation sites by fusing Spo11 with the DNA binding domain of the transcriptional activator Gal4 (Peciña et al., 2002 Cell, 111, 173-184). The Gal4 Spo11 fusion protein makes it possible to introduce double-strand breaks in so-called 'cold' chromosomal regions, at the Gal4 DNA binding sites.

However, in this last approach, the introduction of double-strand breaks is conditioned by the presence of Gal4 binding sites, and thus it remains impossible to induce targeted meiotic recombination phenomena independently of specific binding sites.

SUMMARY OF THE INVENTION

The objective of the present invention is to propose a method for inducing targeted meiotic recombinations in eukaryotic cells, preferably in yeast or plant cells, in any region of the genome, independently of any known binding site, and notably in so-called 'cold' chromosomal regions.

Thus, according to a first aspect, the present invention relates to a method for inducing targeted meiotic recombinations in a eukaryotic cell comprising:

introducing into said cell:

a) a fusion protein comprising a Cas9 domain and a Spo11 domain, or a nucleic acid encoding said fusion protein; and b) one or more guide RNAs or one or more nucleic acids encoding said guide RNAs, said guide RNAs comprising an RNA structure for binding to the Cas9 domain of the fusion protein and a sequence complementary to the targeted chromosomal region; and inducing said cell to enter meiotic prophase I.

The fusion protein may further comprise a nuclear localization signal sequence.

Preferably, the Cas9 domain of the fusion protein is a nuclease-deficient Cas9 protein.

The nucleic acid encoding said fusion protein may be placed under the control of a constitutive, inducible or meiosis-specific promoter.

One or more additional guide RNAs targeting one or more other chromosomal regions, or nucleic acids encoding said additional guide RNAs, may be introduced into the eukaryotic cell.

Preferably, the eukaryotic cell is a yeast. The yeast can then be induced to enter prophase I by transferring it to sporulation medium.

Alternatively, the eukaryotic cell is a plant cell.

Preferably, the introduction of the fusion protein, or the nucleic acid encoding same, and the gRNA(s), or the nucleic acid(s) encoding same, into said cell is simultaneous.

Alternatively, the introduction of the fusion protein, or the nucleic acid encoding same, and the gRNA(s), or the nucleic acid(s) encoding same, into said cell is sequential.

The introduction of the nucleic acid encoding the fusion protein and the nucleic acid(s) encoding the gRNA(s) into said cell may also be achieved by crossing two cells into which have been respectively introduced the nucleic acid encoding the fusion protein and the nucleic acid(s) encoding the gRNA(s).

The present invention further concerns, according to a second aspect, a fusion protein as defined in the method above.

According to a third aspect, the present invention further concerns a nucleic acid encoding the above-defined fusion protein.

The present invention also concerns, according to a fourth aspect, an expression cassette or a vector comprising a nucleic acid as defined above.

Preferably, the vector is a plasmid comprising a bacterial origin of replication, an expression cassette comprising a nucleic acid as defined above, one or more selection markers, and/or one or more sequences allowing targeted insertion of the vector, the expression cassette or the nucleic acid into the host-cell genome. In particular, the plasmid comprises a bacterial origin of replication, preferably the ColE1 origin, an expression cassette comprising a nucleic acid as defined above under the control of a promoter, preferably the ADH1 promoter, a terminator, preferably the ADH1 terminator, one or more selection markers, preferably resistance markers such as the gene for resistance to kanamycin or to ampicillin, one or more sequences allowing targeted insertion of the vector, the expression cassette or the nucleic acid into the host-cell genome, preferably at the TRP1 locus of the genome of a yeast. Preferably, the plasmid comprises, or consists of, a nucleotide sequence selected from SEQ ID NO: 1 and SEQ ID NO: 2.

According to a fifth aspect, the present invention also concerns a host cell comprising a fusion protein, a nucleic acid, a cassette or a vector as defined above.

Preferably, the host cell is a eukaryotic cell, more preferably a yeast, plant, fungal or animal cell, and particularly preferably, the host cell is a plant cell or a yeast cell.

Preferably, the host cell is a yeast cell, more preferably a yeast selected from the group consisting of *Saccharomyces cerevisiae, Saccharomyces bayanus, Saccharomyces castelli, Saccharomyces eubayanus, Saccharomyces kluyveri, Saccharomyces kudriavzevii, Saccharomyces mikatae, Saccharomyces uvarum, Saccharomyces paradoxus, Saccharomyces pastorianus* (also called *Saccharomyces carlsbergensis*), and the hybrids obtained from at least one strain belonging to one of these species, and particularly preferably the host cell is *Saccharomyces cerevisiae*.

Alternatively, the host cell is a plant cell, more preferably a plant cell selected from the group consisting of rice, wheat, soy, maize, tomato, *Arabidopsis thaliana*, barley, rapeseed, cotton, sugarcane and beet, and particularly preferably said host cell is a rice cell.

The present invention further concerns, in a sixth aspect, a method for generating variants of a eukaryotic organism, with the exception of humans, comprising:
introducing into a cell of said organism:
a) a fusion protein comprising a Cas9 domain and a Spo11 domain, or a nucleic acid encoding said fusion protein; and
b) one or more guide RNAs, or one or more nucleic acids encoding said guide RNAs, said guide RNAs comprising an RNA structure for binding to the Cas9 domain and a sequence complementary to a targeted chromosomal region; and
inducing said cell to enter meiotic prophase I;
obtaining a cell or cells having the desired recombination(s) at the targeted chromosomal region(s); and
generating a variant of the organism from said recombinant cell.

Preferably, the eukaryotic organism is a yeast or a plant, more preferably a yeast, notably a yeast strain of industrial interest.

In a seventh aspect, the present invention also concerns a method for identifying or locating the genetic information encoding a characteristic of interest in a eukaryotic cell genome comprising:
introducing into the eukaryotic cell:
a) a fusion protein comprising a Cas9 domain and a Spo11 domain, or a nucleic acid encoding said fusion protein; and
b) one or more guide RNAs, or one or more nucleic acids encoding said guide RNAs, said guide RNAs comprising an RNA structure for binding to the Cas9 domain and a sequence complementary to a targeted chromosomal region; and
inducing said cell to enter meiotic prophase I;
obtaining a cell or cells having the desired recombination(s) at the targeted chromosomal region(s); and
analyzing the genotypes and phenotypes of the recombinant cells in order to identify or to locate the genetic information encoding the characteristic of interest.

Preferably, the eukaryotic cell is a yeast or a plant, more preferably a yeast, notably a yeast strain of industrial interest.

Preferably, the characteristic of interest is a quantitative trait of interest (QTL).

The present invention further concerns, in an eighth aspect, a kit comprising a fusion protein, a nucleic acid, a cassette, a vector or a host cell as defined above.

Finally, in a ninth aspect, the present invention concerns the use of a kit as defined above to implement a method as defined above, in particular to (i) induce targeted meiotic recombinations in a eukaryotic cell, (ii) generate variants of a eukaryotic organism, and/or (iii) identify or locate the genetic information encoding a characteristic of interest in a eukaryotic cell genome.

BRIEF DESCRIPTION OF THE DRAWINGS

FIG. 1: Diagram representing the plasmids P1 (SEQ ID NO: 1) and P2 (SEQ ID NO: 2) of the SpCas9-Spo11 or SpCas9*-Spo11 fusion. P1 and P2 respectively encode NLS-SpCas9-Spo11 and NLS-SpCas9*-Spo11 expression in yeast. The black blocks represent the constitutive ADH1 promoter (pADH1) and the ADH1 terminator (tADH1). The arrow indicates the direction of transcription under the control of the ADH1 promoter.

FIG. 2: Diagram representing the gRNA expression plasmids in yeast cells. (A) Diagram of the plasmid containing a single gRNA expression cassette for targeting a single region of the yeast genome. RE indicates the restriction site where the specificity-determining sequence (SDS) of the gRNA is inserted by the Gibson method. The promoter and the terminator (Term) are RNA polymerase III-dependent. The arrow on the promoter indicates the direction of transcription of the sequence. A gRNA expression cassette contains a gRNA flanked by a promoter and a terminator. (B) Diagram of the plasmid containing several gRNA expression cassettes for targeting multiple regions of the yeast genome (multiplexed targeting). The various gRNA cassettes are distinguished by their specificity-determining sequence (SDS). They were introduced successively into the multiple cloning site (MCS) by conventional cloning/ligation techniques.

FIG. 13: Sequences of the gRNAs used. In uppercase and lowercase characters are respectively indicated the specificity-determining sequence of the gRNA (20 nucleotides in length) and the sequence constituting the structure of the gRNA ("handle", 82 nucleotides in length).

DETAILED DESCRIPTION OF THE INVENTION

Figure 3:
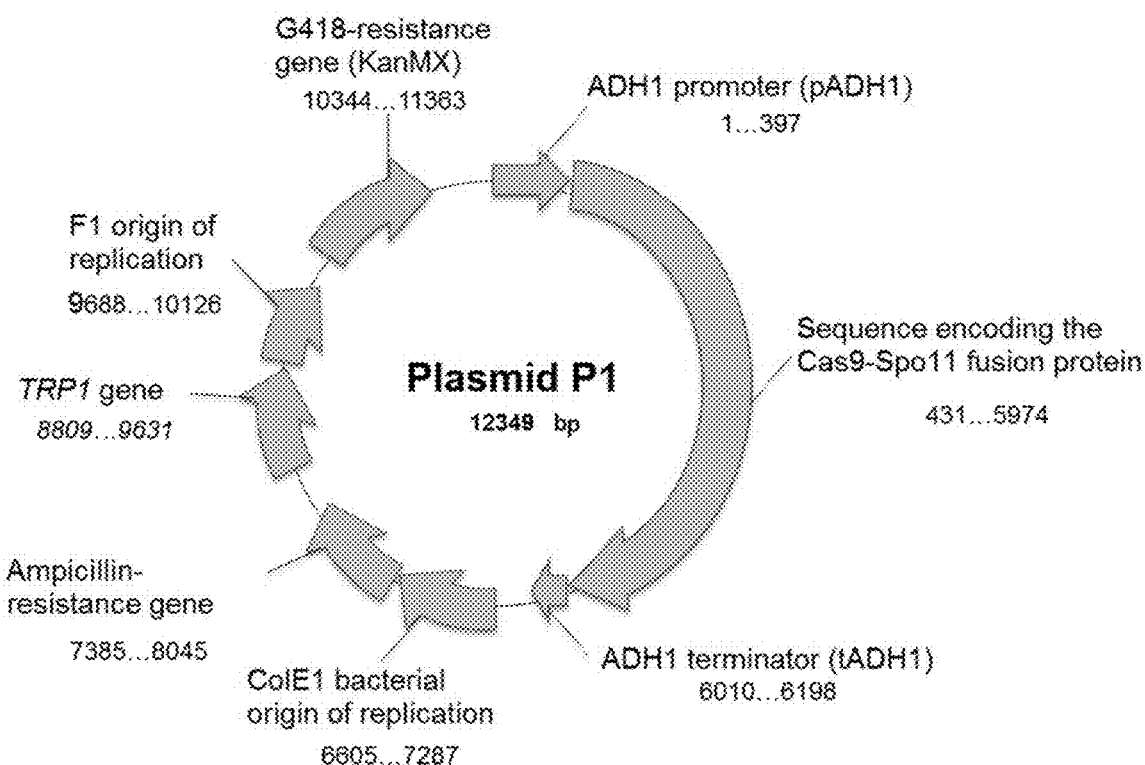
FIG. 3: Diagram representing the plasmid P1 (SEQ ID NO: 1).
Figure 4:
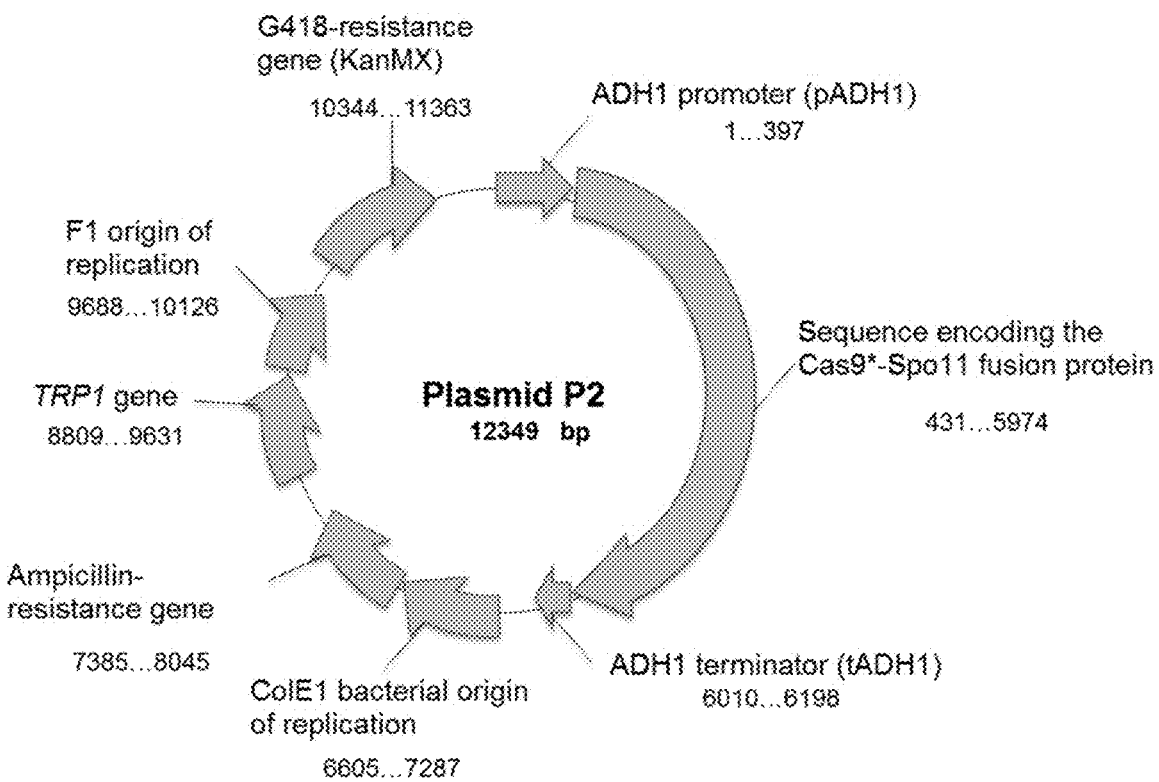
FIG. 4: Diagram representing the plasmid P2 (SEQ ID NO: 2).

The Clustered Regularly Interspaced Shorts Palindromic Repeats (CRISPR)-Cas9 system is a bacterial defense system against foreign DNA. This system rests essentially on the association of a Cas9 protein and a "guide" RNA (gRNA or sgRNA) responsible for the specificity of the cleavage site. It can be used to create DNA double-strand breaks (DSBs) at the sites targeted by the CRISPR/Cas9 system. This system has already been used for targeted engineering of the genome in eukaryotic cells (see for example the patent application EP2764103), notably human cells (Cong L et al., 2013, Science 339(6121):819-823; Mali P et al., 2013, Science, 339(6121):823-826; Cho S W et al., 2013, Nature Biotechnology 31(3):230-232), rat cells (Li D, et al., 2013, Nature Biotechnology, 31(8):681-683; WO 2014/089290), mouse cells (Wang H et al., 2013, Cell, 153(4):910-918), rabbit cells (Yang D et al., 2014, Journal of Molecular Cell Biology, 6(1):97-99), frog cells (Nakayama T et al., 2013, Genesis, 51(12):835-843), fish cells (Hwang W Y et al., 2013, Nature Biotechnology, 31(3):227-229), plant cells (Shan Q et al., 2013, Nature Biotechnology, 31(8):686-688; Jiang W et al., 2013, Nucleic Acids Research, 41(20):e188), *drosophila* cells (Yu Z et al., 2013, Genetics, 195(1):289-291), nematode cells (Friedland A E et al., 2013, Nature Methods, 10(8):741-743), yeast cells (DiCarlo J, et al., 2013, Genome engineering in *Saccharomyces cerevisiae* using CRISPR-Cas systems. Nucleic Acids Research 41(7):4336-4343), but also bacterial cells (Jiang W et al., 2013, Nature Biotechnology, 31(3):233-239). On the other hand, this system has never been used to target meiotic recombination sites in any organism.

The inventors have shown that it is possible to modify the CRISPR-Cas9 system in order to induce targeted meiotic recombinations in a eukaryotic cell, and in particular in a yeast. They have in fact shown that the combined expression of a Spo11-Cas9 fusion protein and one or more guide RNAs made it possible to target the action of the transesterase Spo11 which is responsible for double-strand breaks during meiosis. Repair of these breaks by using as matrix a chromatid of the homologous chromosome induces the desired recombination phenomena.

Thus, the present invention relates to a method for inducing targeted meiotic recombinations in a eukaryotic cell comprising:

introducing into said cell:

a) a fusion protein comprising a Cas9 domain and a Spo11 domain, or a nucleic acid encoding said fusion protein; and b) one or more guide RNAs or one or more nucleic acids encoding said guide RNAs, said guide RNAs comprising an RNA structure for binding to the Cas9 domain of the fusion protein and a sequence complementary to the targeted chromosomal region; and inducing said cell to enter meiotic prophase I.

As used herein, the term "eukaryotic cell" refers to a yeast, plant, fungal or animal cell, in particular a mammalian cell such as a mouse cell or a rat cell, or an insect cell. The eukaryotic cell is preferably nonhuman and/or nonembryonic.

According to a particular embodiment, the eukaryotic cell is a yeast cell, in particular a yeast of industrial interest. Exemplary yeasts of interest include, but are not limited to, yeasts of the genus *Saccharomyces sensu stricto, Schizosaccharomyces, Yarrowia, Hansenula, Kluyveromyces, Pichia* or *Candida*, as well as the hybrids obtained from a strain belonging to one of these genera.

Preferably, the yeast of interest belongs to the genus *Saccharomyces*. It may notably belong to a species selected from the group consisting of *Saccharomyces cerevisiae, Saccharomyces bayanus, Saccharomyces castelli, Saccharomyces eubayanus, Saccharomyces kluyveri, Saccharomyces kudriavzevii, Saccharomyces mikatae, Saccharomyces uvarum, Saccharomyces paradoxus* and *Saccharomyces pastorianus* (also called *Saccharomyces carlsbergensis*), or is a hybrid obtained from a strain belonging to one of these species such as for example an *S. cerevisiae/S. paradoxus* hybrid or an *S. cerevisiae/S. uvarum* hybrid.

According to another particular embodiment, the eukaryotic cell is a fungal cell, in particular a fungal cell of industrial interest. Exemplary fungi include, but are not limited to, filamentous fungal cells. Filamentous fungi include fungi belonging to the subdivisions Eumycota and Oomycota. Filamentous fungal cells may be selected from the group consisting of *Trichoderma, Acremonium, Aspergillus, Aureobasidium, Bjerkandera, Ceriporiopsis, Chrysosporium, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium* or *Trametes* cells.

According to still another particular embodiment, the eukaryotic cell is a plant cell, in particular a plant cell of agronomic interest. Exemplary plants include, but are not limited to, rice, wheat, soy, maize, tomato, *Arabidopsis thaliana*, barley, rapeseed, cotton, sugarcane and beet. According to a preferred embodiment, the eukaryotic cell is a rice cell.

Preferably, the eukaryotic cell is heterozygous for the gene(s) targeted by the guide RNA(s).

As used herein, the term "fusion protein" refers to a chimeric protein comprising at least two domains derived from the combination of different proteins or protein fragments. The nucleic acid encoding this protein is obtained by recombination of the regions encoding the proteins or protein fragments so that they are in phase and transcribed on the same mRNA. The various domains of the fusion protein may be directly adjacent or may be separated by binding sequences (linkers) which introduce a certain structural flexibility into the construction.

The fusion protein used in the present invention comprises a Cas9 domain and a Spo11 domain.

The Cas9 domain is the domain of the fusion protein that is able to interact with the guide RNAs and to target the nuclease activity of the Spo11 domain toward a given chromosomal region. The Cas9 domain can consist of a Cas9 protein (also called Csn1 or Csx12), wild-type or modified, or a fragment of this protein capable of interacting with the guide RNAs. The Cas9 protein can notably be modified in order to modulate its enzymatic activity. Thus, the nuclease activity of the Cas9 protein can be modified or inactivated. The Cas9 protein can also be truncated to remove the protein domains not essential to the functions of the fusion protein, in particular the Cas9 protein domains that are not necessary to interaction with the guide RNAs.

The Cas9 protein or fragment thereof as used in the present invention can be obtained from any known Cas9 protein (Makarova et al., 2008, Nat. Rev. Microbiol., 9, pp. 466-477). Exemplary Cas9 proteins that can be used in the present invention include, but are not limited to, the Cas9 proteins from *Streptococcus pyogenes, Streptococcus thermophilus, Streptococcus* sp., *Nocardiopsis dassonvillei, Streptomyces pristinaespiralis, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicellulosiruptor bescii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsonii, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or *Acaryochloris marina*. Other Cas9 proteins that can be used in the present invention are also described in the article by Makarova et al. (Makarova et al., 2008, Nat. Rev. Microbiol., 9, pp. 466-477). Preferably, the Cas9 domain comprises, or consists of, the Cas9 protein from *Streptococcus pyogenes* (NCBI entry number: WP_010922251.1, SEQ ID NO: 8) or a fragment thereof capable of interacting with the guide RNAs.

According to a particular embodiment, the Cas9 domain consists of a whole Cas9 protein, preferably the Cas9 protein from *Streptococcus pyogenes*.

Generally, Cas9 proteins comprise two nuclease domains: a domain related to a RuvC domain and a domain related to an HNH domain. These two domains cooperate to create DNA double-strand breaks (Jinek et al., Science, 337: 816-821). Each of these nuclease domains can be inactivated by deletion, insertion or substitution according to techniques well-known to a person skilled in the art such as directed mutagenesis, PCR mutagenesis or total gene synthesis.

Thus, the RuvC domain can be inactivated for example by the substitution D10A and the HNH domain can be inactivated for example by the substitution H840A (Jinek et al., Science, 337: 816-821), the indicated positions being those of SEQ ID NO: 8.

In the peptide sequences described in this document, the amino acids are represented by their one-letter code according to the following nomenclature: C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan and Y: tyrosine.

According to an embodiment, the Cas9 domain is deficient in at least one nuclease activity. This domain can be obtained by inactivating at least one nuclease domain of the Cas9 protein as described above.

According to a particular embodiment, the Cas9 domain comprises, or consists of, a Cas9 protein or a Cas9 protein fragment, lacking nuclease activity (also called Cas9* or dCas9). This catalytically-inactive form can be obtained by inactivating the two nuclease domains of the Cas9 protein as mentioned above, for example by introducing the two point mutations substituting the aspartate at position 10 and the histidine at position 840 by alanines.

According to a preferred embodiment, the Cas9 domain comprises, or consists of, a Cas9 protein, preferably the Cas9 protein from *Streptococcus pyogenes* (spCas9), lacking nuclease activity (spCas9*).

According to a particular embodiment, the Cas9 domain comprises, or consists of, the sequence presented in SEQ ID NO: 8 wherein the aspartate at position 10 and the histidine at position 840 have been substituted by alanines.

Spo11 is a protein related to the catalytic A subunit of a type II topoisomerase present in archaebacteria (Bergerat et al., Nature, vol. 386, pp 414-7). It catalyzes the DNA double-strand breaks initiating meiotic recombinations. It is a highly conserved protein for which homologs exist in all eukaryotes. Spo11 is active as a dimer formed of two subunits, each of which cleaves a DNA strand. Although essential, Spo11 does not act alone to generate double-strand breaks during meiosis. In the yeast *S. cerevisiae*, for example, it cooperates with Rec102, Rec103/Sk18, Rec104, Rec114, Mer1, Mer2/Rec107, Mei4, Mre2/Nam8, Mre11, Rad50, Xrs2/Nbs1, Hop1, Red1, Mek1, Set1 and Spp1 proteins and with other partners described in the articles by Keeney et al. (2001 Curr. Top. Dev. Biol, 52, pp. 1-53), Smith et al. (Curr. Opin. Genet. Dev, 1998, 8, pp. 200-211) and Acquaviva et al. (2013 Science, 339, pp. 215-8). It was recently shown, however, that targeting Spo11 to a given site is sufficient to initiate the meiotic recombination process (Peciña et al., 2002 Cell, 111, 173-184). It should be noted that several Spo11 protein homologs can coexist in the same cell, notably in plants. Preferably, the Spo11 protein is one of the Spo11 proteins of the eukaryotic cell of interest.

The Spo11 domain of the Cas9-Spo11 fusion protein is generally the domain responsible for double-strand breaks. This domain may consist of a Spo11 protein or fragment thereof capable of inducing DNA double-strand breaks.

The Spo11 protein or fragment thereof as used in the present invention can be obtained from any known Spo11 protein such as the Spo11 protein from *Saccharomyces cerevisiae* (Gene ID: 856364, NCBI entry number: NP_011841 (SEQ ID NO: 9) Esposito and Esposito, Genetics, 1969, 61, pp. 79-89), the AtSpo11-1 and AtSpo11-2 proteins from *Arabidopsis thaliana* (Grelon M. et al., 2001, Embo J., 20, pp. 589-600), the mSpo11 murine protein (Baudat F et al., Molecular Cell, 2000, 6, pp. 989-998), the Spo11 protein from *C. elegans* or the Spo11 protein from *drosophila* meiW68 (McKim et al., 1998, Genes Dev, 12(18), pp. 2932-42). Of course, these examples are non-limiting and any known Spo11 protein can be used in the method according to the invention.

According to a preferred embodiment, the Spo11 domain comprises, or consists of, a Spo11 protein, preferably a Spo11 protein from *Saccharomyces cerevisiae*, such as for example the protein having the sequence SEQ ID NO: 9.

According to a particular embodiment, the Spo11 domain is nuclease-deficient. In particular, the Spo11 domain may comprise, or consist of, the Spo11-Y135F mutant protein, a mutant protein incapable of inducing DNA double-strand breaks (Neale M J, 2002, Molecular Cell, 9, 835-846). The position indicated is that of SEQ ID NO: 9.

The ability of the fusion protein according to the invention to induce DNA double-strand breaks may come from the Cas9 domain or from the Spo11 domain. Thus, the fusion protein comprises at least one domain, Cas9 or Spo11, having nuclease activity, preferably the Spo11 domain.

According to a particular embodiment, several fusion proteins according to the invention comprising various Spo11 domains can be introduced into the same cell. In particular, when several Spo11 homologs exist in the eukaryotic cell of interest, the various fusion proteins may each comprise a different Spo11 homolog. By way of example, two fusion proteins according to the invention comprising respectively the Spo11-1 and Spo11-2 domains of *Arabidopsis thaliana* may be introduced into the same cell, preferably into the same *Arabidopsis thaliana* cell. Still by way of example, one or more fusion proteins according to the invention comprising the Spo11-1, Spo11-2, Spo11-3 and/or Spo11-4 domains of rice may be introduced into the same cell, preferably into the same rice cell. Numerous Spo11 homologs have been identified in various species, in particular in plant species (Sprink T and Hartung F, Frontiers in Plant Science, 2014, Vol. 5, article 214, doi: 10.3389/fpls.2014.00214; Shingu Y et al., BMC Mol Biol, 2012, doi: 10.1186/1471-2199-13-1). A person skilled in the art can readily identify the Spo11 homologs in a given species, notably by means of well-known bioinformatics techniques.

The fusion protein according to the invention comprises a Spo11 domain and a Cas9 domain as defined above.

According to an embodiment, the Spo11 domain is on the N-terminal side and the Cas9 domain is on the C-terminal side of the fusion protein. According to another embodiment, the Spo11 domain is on the C-terminal side and the Cas9 domain is on the N-terminal side of the fusion protein.

The fusion protein may also comprise a nuclear localization signal (NLS) sequence. NLS sequences are well-known to a person skilled in the art and in general comprise a short sequence of basic amino acids. By way of example, the NLS sequence may comprise the sequence PKKKRKV (SEQ ID NO: 3). The NLS sequence may be present at the N-terminal end, at the C-terminal end, or in an internal region of the fusion protein, preferably at the N-terminal end of the fusion protein.

The fusion protein may also comprise an additional cell-penetrating domain, i.e., a domain facilitating the entry of the fusion protein into the cell. This type of domain is well-known to a person skilled in the art and may comprise for example a penetrating peptide sequence derived from the HIV-1 TAT protein such as GRKKRRQRRRPPQPKKKRKV (SEQ ID NO: 4), derived from the TLM sequence of the human hepatitis B virus such as PLSSIFSRIGDPPKKKRKV (SEQ ID NO: 5), or a polyarginine peptide sequence. This cell penetrating domain may be present at the N-terminal end or at the C-terminal end or may be inside the fusion protein, preferably at the N-terminal end.

The fusion protein may further comprise one or more binding sequences (linkers) between the Cas9 and Spo11 domains, and optionally between these domains and the other domains of the protein such as the nuclear localization signal sequence or the cell-penetrating domain. The length of these linkers is readily adjustable by a person skilled in the art. In general, these sequences comprise between 10 and 20 amino acids, preferably about 15 amino acids and more preferably 12 amino acids. The linkers between the various domains may be of identical or different lengths.

According to a particular embodiment, the fusion protein comprises, or consists of, successively, from the N-terminal end to the C-terminal end: a nuclear localization signal, a first linker (linker1), a Cas9 domain, a second linker (linker2) and a Spo11 domain.

According to another particular embodiment, the fusion protein comprises, or consists of, successively, from the N-terminal end to the C-terminal end: a nuclear localization signal, a first linker (linker1), a Spo11 domain, a second linker (linker2) and a Cas9 domain.

The fusion protein may further comprise a tag that is a defined amino acid sequence. This tag may notably be used to detect the expression of the fusion protein, to identify the proteins interacting with the fusion protein or to characterize the binding sites of the fusion protein in the genome. The detection of the tag attached to the fusion protein may be carried out with an antibody specific for said tag or by means of any other technique well-known to a person skilled in the art. The identification of the proteins interacting with the fusion protein may be carried out, for example, by co-immunoprecipitation techniques. The characterization of the binding sites of the fusion protein in the genome may be carried out, for example, by immunoprecipitation, chromatin immunoprecipitation coupled with realtime quantitative PCR (ChIP-qPCR), chromatin immunoprecipitation coupled with sequencing techniques (ChIP-Seq), cartography using oligonucleotide (oligo) mapping or any other technique well-known to a person skilled in the art.

This tag may be present at the N-terminal end of the fusion protein, at the C-terminal end of the fusion protein, or at a non-terminal position in the fusion protein. Preferably, the tag is present at the C-terminal end of the fusion protein. The fusion protein may comprise one or more tags, which may be identical or different.

The tags, as used in the present invention, may be selected from the many tags well-known to a person skilled in the art. In particular, the tags used in the present invention may be peptide tags and/or protein tags. Preferably, the tags used in the present invention are peptide tags. Exemplary peptide tags that can be used in the present invention include, but are not limited to, tags consisting of repeats of at least six histidines (His), in particular tags consisting of six or eight histidines, as well as Flag, polyglutamate, hemagglutinin (HA), calmodulin, Strep, Etag, myc, V5, Xpress, VSV, Stag, Avi, SBP, Softag 1, Softag 2, Softag 3, isopetag, SpyTag and tetracysteine tags and combinations thereof. Exemplary protein tags that can be used in the present invention include, but are not limited to, glutathione S-transferase (GST), *Staphylococcus aureus* protein A, Nus A, chitin-binding protein (CBP), thioredoxin, maltose binding protein (MBP), biotin carboxyl carrier protein (BCCP), and immunoglobulin constant fragment (Fc) tags, tags comprising a fluorescent protein such as green fluorescent protein (GFP), red fluorescent protein (RFP), cyan fluorescent protein (CFP) or yellow fluorescent protein (YFP), and combinations thereof.

According to a preferred embodiment, the fusion protein comprises a tag consisting of six histidines and/or one or more Flag motifs, preferably three Flag motifs. According to a particular embodiment, the fusion protein comprises a tag consisting of six histidines and three Flag motifs.

Alternatively, the Spo11 domain of the Cas9-Spo11 fusion protein may be replaced by one of the Spo11 partners capable of recruiting Spo11, i.e., a protein that forms a complex with Spo11 and thus induces the formation of double-strand breaks. This partner may be selected from the proteins cited in the articles by Keeney et al. (2001 Curr. Top. Dev. Biol, 52, pp. 1-53), Smith et al. (Curr. Opin. Genet. Dev, 1998, 8, pp. 200-211) and Acquaviva et al. (2013 Science, 339, pp. 215-8), and more particularly from the group consisting of Rec102, Rec103/Sk18, Rec104, Rec114, Mer1, Mer2/Rec107, Mei4, Mre2/Nam8, Mre11, Rad50, Xrs2/Nbs1, Hop1, Red1, Mek1, Set1 and Spp1. Preferably, the partner replacing the Spo11 domain is Mei4 or Spp1.

All the embodiments described for the Cas9-Spo11 fusion protein also apply to fusion proteins wherein the Spo11 domain is replaced by one of its partners.

The fusion protein as described above may be introduced into the cell in protein form, notably in mature form or in precursor form, preferably in mature form, or in the form of a nucleic acid encoding said protein.

When the fusion protein is introduced into the cell in protein form, protecting groups may be added at the C and/or N-terminal ends in order to improve the fusion protein's resistance to peptidases. For example, the protecting group at the N-terminal end may be an acylation or an acetylation and the protecting group at the C-terminal end may be an amidation or an esterification. The action of the proteases may also be thwarted by the use of amino acids having the D-configuration, the cyclization of the protein by formation of disulfide bridges, lactam rings or bonds between the N- and C-terminal ends. The fusion protein of the invention may also comprise pseudopeptide bonds replacing the "conventional" peptide bonds (CONH) and conferring increased resistance to peptidases, such as $CHOH-CH_2$, $NHCO$, $CH_2-O$, $CH_2CH_2$, $CO-CH_2$, $N-N$, $CH=CH$, $CH_2NH$, and $CH_2-S$. The fusion protein may also comprise one or more amino acids that are rare amino acids, notably hydroxyproline, hydroxylysine, allo-hydroxylysine, 6N-methyllysine, N-ethylglycine, N-methylglycine, N-ethylasparagine, alloisoleucine, N-methylisoleucine, N-methylvaline, pyroglutamine, aminobutyric acid; or synthetic amino acids notably ornithine, norleucine, norvaline and cyclohexylalanine.

The fusion protein according to the invention can be obtained by conventional chemical synthesis (solid-phase or homogeneous liquid-phase) or by enzymatic synthesis (Kullmann W, Enzymatic peptide synthesis, 1987, CRC Press, Florida). It may also be obtained by a method consisting in growing a host cell expressing a nucleic acid encoding the fusion protein and recovering said protein from these cells or from the culture medium.

As used in the present application, the term "guide RNA" or "gRNA" refers to an RNA molecule capable of interacting with the Cas9 domain of the fusion protein in order to guide it toward a target chromosomal region.

Each gRNA comprises two regions:
 a first region (commonly called the "SDS" region), at the 5' end of the gRNA, which is complementary to the target chromosomal region and which imitates the crRNA of the endogenous CRISPR system, and
 a second region (commonly called the "handle" region), at the 3' end of the gRNA, which mimics the basepair interactions between the transactivating crRNA (tracrRNA) and the crRNA of the endogenous CRISPR system and has a stemloop double-stranded structure ending in the 3' direction with an essentially single-stranded sequence. This second region is essential to binding of the gRNA to the Cas9 domain of the fusion protein.

The first region of the gRNA varies according to the targeted chromosomal sequence. On the other hand, the handle regions of the various gRNAs used may be identical or different. According to a particular embodiment, the handle region comprises, or consists of, the 3' 82 nucleotide sequence of the sequences SEQ ID NO: 10 to 16 (sequence in lowercase in FIG. 13).

The SDS region of the gRNA, which is complementary to the target chromosomal region, generally comprises between 10 and 25 nucleotides. Preferably, this region has a length of 19, 20 or 21 nucleotides, and particularly preferably 20 nucleotides.

The second region of the gRNA has a stemloop (or hairpin) structure. The lengths of the stem and the loop may vary. Preferably, the loop has a length of 3 to 10 nucleotides and the stem a length of 6 to 20 nucleotides. The stem may optionally have mismatched regions (forming "bulges") of 1 to 10 nucleotides. Preferably, the total length of this handle region is 50 to 100 nucleotides, and more particularly preferably 82 nucleotides.

The total length of a gRNA is generally 50 to 140 nucleotides, preferably 80 to 125 nucleotides, and more particularly preferably 90 to 110 nucleotides. According to a particular embodiment, a gRNA as used in the present invention has a length of 102 nucleotides.

The gRNA is preferably formed of a single RNA molecule comprising the two domains. Alternatively, the gRNA may be formed of two distinct RNA molecules, the first molecule comprising the SDS region and half of the stem of the second region, and the second molecule comprising the second half of the stem of the gRNA. Thus, the pairing of the two RNA molecules by their complementary sequences at the stem, forms a functional gRNA.

A person skilled in the art can, by using well-known techniques, readily define the sequence and the structure of the gRNAs according to the chromosomal region to be targeted (see for example the article by Di Carlo et al., Nucleic Acids Research 2013, 1-8).

In the method according to the invention, one or more gRNAs can be used simultaneously. These different gRNAs may target identical or different chromosomal regions, preferably different.

The gRNAs can be introduced into the eukaryotic cell as mature gRNA molecules, as precursors, or as one or more nucleic acids encoding said gRNAs.

When the gRNA(s) are introduced into the cell directly as RNA molecules (mature or precursors), these gRNAs may contain modified nucleotides or chemical modifications allowing them, for example, to increase their resistance to nucleases and thus to increase their lifespan in the cell. They may notably include at least one modified or non-natural nucleotide such as, for example, a nucleotide comprising a modified base, such as inosine, methyl-5-deoxycytidine, dimethylamino-5-deoxyuridine, deoxyuridine, diamino-2,6-purine, bromo-5-deoxyuridine or any other modified base allowing hybridization. The gRNAs used according to the invention may also be modified at the internucleotide bond such as for example phosphorothioates, H phosphonates or alkylphosphonates, or at the backbone such as for example alpha oligonucleotides, 2'-O-alkylriboses or peptide nucleic acid (PNA) (Egholm et al., 1992 J. Am. Chem. Soc., 114, 1895-1897).

The gRNAs may be natural RNA, synthetic RNA, or RNA produced by recombination techniques. These gRNAs may be prepared by any methods known to a person skilled in the art such as, for example, chemical synthesis, in vivo transcription or amplification techniques.

According to an embodiment, the method comprises introducing into the eukaryotic cell the fusion protein and one or more gRNAs capable of targeting the action of the fusion protein toward a given chromosomal region. The protein and the gRNAs may be introduced into the cytoplasm or the nucleus of the eukaryotic cell by any method known to a person skilled in the art, for example by microinjection. The fusion protein may notably be introduced into the cell as an element of a protein-RNA complex comprising at least one gRNA.

According to another embodiment, the method comprises introducing into the eukaryotic cell the fusion protein and one or more nucleic acids encoding one or more gRNAs.

According to still another embodiment, the method comprises introducing into the eukaryotic cell a nucleic acid encoding the fusion protein and one or more gRNAs.

According to still another embodiment, the method comprises introducing into the eukaryotic cell a nucleic acid encoding the fusion protein and one or more nucleic acids encoding one or more gRNAs.

The fusion protein, or the nucleic acid encoding said fusion protein, and the gRNA(s), or the nucleic acid(s) encoding said gRNA(s), may be introduced into the cell simultaneously or sequentially.

Alternatively, and more particularly concerning plant cells, the nucleic acid encoding the fusion protein and the nucleic acid(s) encoding the gRNA(s) may be introduced into a cell by crossing two cells into which have been respectively introduced the nucleic acid encoding the fusion protein and the nucleic acid(s) encoding the gRNA(s).

Alternatively, and more particularly concerning plant cells, the nucleic acid encoding the fusion protein and the nucleic acid(s) encoding the gRNA(s) may be introduced into a cell by mitosis of a cell into which the nucleic acid encoding the fusion protein and the nucleic acid(s) encoding the gRNA(s) have been previously introduced.

In the embodiments where the fusion protein and/or the gRNA(s) are introduced into the eukaryotic cell as a nucleic acid encoding said protein and/or said gRNA(s), the expression of said nucleic acids makes it possible to produce the fusion protein and/or the gRNA(s) in the cell.

In the context of the invention, by "nucleic acid" is meant any molecule based on DNA or RNA. These molecules may be synthetic or semisynthetic, recombinant, optionally amplified or cloned into vectors, chemically modified, comprising non-natural bases or modified nucleotides comprising for example a modified bond, a modified purine or pyrimidine base, or a modified sugar. Preferably, the use of codons is optimized according to the nature of the eukaryotic cell.

The nucleic acids encoding the fusion protein and those encoding the gRNAs may be placed under the control of identical or different promoters, which may be constitutive or inducible, in particular meiosis-specific promoters. According to a preferred embodiment, the nucleic acids are placed under the control of constitutive promoters such as the ADH1 promoter or the RNA polymerase III-dependent pRPR1 and SNR52 promoters, more preferably the pRPR1 promoter.

The nature of the promoter may also depend on the nature of the eukaryotic cell. According to a particular embodiment, the eukaryotic cell is a plant cell, preferably a rice cell, and the nucleic acids are placed under the control of a promoter selected from the maize ubiquitin promoters (pZmUbi) and the polymerase III U3 and U6 promoters. According to a preferred embodiment, the nucleic acid encoding the fusion protein is placed under the control of the promoter pZmUbi and the nucleic acids encoding the gRNAs are placed under the control of the U3 or U6 promoter, preferably the U3 promoter.

The nucleic acids encoding the fusion protein and the gRNA(s) may be disposed on the same construction, in particular on the same expression vector, or on distinct constructions. Alternatively, the nucleic acids may be inserted into the genome of the eukaryotic cell in identical or distinct regions. According to a preferred embodiment, the nucleic acids encoding the fusion protein and the gRNA(s) are disposed on the same expression vector.

The nucleic acids as described above may be introduced into the eukaryotic cell by any method known to a person skilled in the art, in particular by microinjection, transfection, electroporation and biolistics.

Optionally, the expression or the activity of the endogenous Spo11 protein of the eukaryotic cell may be suppressed in order to better control meiotic recombination phenomena. This inactivation may be carried out by techniques well-known to a person skilled in the art, notably by inactivating the gene encoding the endogenous Spo11 protein or by inhibiting its expression by means of interfering RNA.

After introducing into the eukaryotic cell the fusion protein and one or more gRNAs, or nucleic acids encoding same, the method according to the invention comprises inducing said cell to enter meiotic prophase I.

This induction may be done according to various methods, well-known to a person skilled in the art.

By way of example, when the eukaryotic cell is a mouse cell, the cells may be induced to enter meiotic prophase I by adding retinoic acid (Bowles J et al., 2006, Science, 312 (5773), pp. 596-600).

When the eukaryotic cell is a plant cell, the induction of meiosis is carried out according to a natural process. According to a particular embodiment, after transforming a callus comprising one or more plant cells, a plant is regenerated and placed in conditions promoting the induction of a reproductive phase and thus of the meiotic process. These conditions are well-known to a person skilled in the art.

When the eukaryotic cell is a yeast, this induction may be carried out by transferring the yeast to sporulation medium, in particular from rich medium to sporulation medium, said sporulation medium preferably lacking a fermentable carbon source or a nitrogen source, and incubating the yeasts in the sporulation medium for a sufficient period of time to induce Spo11 dependent double-strand breaks. The initiation of the meiotic cycle depends on several signals: the presence of the two mating type alleles MATa and MATα, the absence of a nitrogen source and a fermentable carbon source.

As used in this document, the term "rich medium" refers to a culture medium comprising a fermentable carbon source and a nitrogen source as well as all the nutritive elements necessary for yeasts to multiply by mitotic division. This medium can be readily selected by a person skilled in the art and may, for example, be selected from the group consisting of YPD medium (1% yeast extract, 2% bactopeptone and 2% glucose), YPG medium (1% yeast extract, 2% bactopeptone and 3% glycerol) and synthetic complete (SC) medium (Treco and Lundblad, 2001, Curr. Protocol. Mol. Biol., Chapter 13, Unit 13.1).

As used in this document, the term "sporulation medium" refers to any medium that induces yeast cells to enter meiotic prophase without vegetative growth, in particular a culture medium not comprising a fermentable carbon source or a nitrogen source but comprising a carbon source that can be metabolized by respiration, such as acetate. This medium can be readily selected by a person skilled in the art and may, for example, be selected from the group consisting of 1% KAc medium (Wu and Lichten, 1994, Science, 263, pp. 515-518), SPM medium (Kassir and Simchen, 1991, Meth. Enzymol., 194, 94-110) and the sporulation media described in the article by Sherman (Sherman, Meth. Enzymol., 1991, 194, 3-21).

According to a preferred embodiment, before being incubated in the sporulation medium, the cells are grown for a few rounds of division in a pre-sporulation medium so as to obtain effective and synchronous sporulation. The pre-sporulation medium can be readily selected by a person skilled in the art. For example, this medium may be SPS medium (Wu and Lichten, 1994, Science, 263, pp. 515-518).

The choice of media (rich medium, pre-sporulation medium, sporulation medium) depends on the physiological and genetic characteristics of the yeast strain, notably if this strain is auxotrophic for one or more compounds.

Once the cell is engaged in meiotic prophase I, the meiotic process may continue until four daughter cells having the required recombinations are produced.

Alternatively, when the eukaryotic cell is a yeast, and in particular a yeast of the genus *Saccharomyces*, the cells can be returned to growth conditions in order to resume a mitotic process. This phenomenon, called "return-to-growth" or "RTG", was previously described in the patent application WO 2014/083142 and occurs when cells that have entered meiosis in response to a nutritional deficiency are placed in the presence of a carbon and nitrogen source after the formation of Spo11-dependent double-strand breaks but before the first meiotic division (Honigberg and Esposito, Proc. Nat. Acad. Sci USA, 1994, 91, 6559-6563). Under these conditions, they stop progressing through the stages of meiotic differentiation to resume a mitotic growth mode while inducing the desired recombinations during repair of the double strand breaks caused by Spo11 (Sherman and Roman, Genetics, 1963, 48, 255-261; Esposito and Esposito, Proc. Nat. Acad. Sci, 1974, 71, pp. 3172-3176; Zenvirth et al., Genes to Cells, 1997, 2, pp. 487-498).

The method may further comprise obtaining a cell or cells having the desired recombination(s).

The method according to the invention can be used in all applications where it is desirable to improve and control meiotic recombination phenomena. In particular, the invention makes it possible to associate, preferentially, genetic traits of interest. This preferential association makes it possible, on the one hand, to reduce the time necessary to select them and, on the other hand, to generate possible but improbable natural combinations. Lastly, according to the embodiment selected, the organisms obtained by this method may be regarded as non-genetically modified organisms (non-GMO).

According to another aspect, the present invention relates to a method for generating variants of a eukaryotic organism, with the exception of humans, preferably a yeast or a plant, more preferably a yeast, notably a yeast strain of industrial interest, comprising:

introducing into a cell of said organism:
a) a fusion protein comprising a Cas9 domain and a Spo11 domain, or a nucleic acid encoding said fusion protein; and
b) one or more guide RNAs, or one or more nucleic acids encoding said guide RNAs, said guide RNAs comprising an RNA structure for binding to the Cas9 domain and a sequence complementary to a targeted chromosomal region; and
    inducing said cell to enter meiotic prophase I;
    obtaining a cell or cells having the desired recombination(s) at the targeted chromosomal region(s); and
    generating a variant of the organism from said recombinant cell.

In this method, the term "variant" should be understood broadly to refer to an organism having at least one genotypic or phenotypic difference from the parent organisms.

The recombinant cells can be obtained by allowing meiosis to continue until spores are obtained, or, in the case of yeasts, by returning the cells to growth conditions after the induction of double-strand breaks in order to resume a mitotic process.

When the eukaryotic cell is a plant cell, a variant of the plant can be generated by fusion of plant gametes, at least one of the gametes being a recombinant cell by the method according to the invention.

The present invention also concerns a method for identifying or locating the genetic information encoding a characteristic of interest in the genome of a eukaryotic cell, preferably a yeast, comprising:

introducing into the eukaryotic cell:
a) a fusion protein comprising a Cas9 domain and a Spo11 domain, or a nucleic acid encoding said fusion protein; and
b) one or more guide RNAs, or one or more nucleic acids encoding said guide RNAs, said guide RNAs comprising an RNA structure for binding to the Cas9 domain and a sequence complementary to a targeted chromosomal region; and inducing said cell to enter meiotic prophase I;

obtaining a cell or cells having the desired recombination(s) at the targeted chromosomal region(s); and analyzing the genotypes and phenotypes of the recombinant cells so as to identify or locate the genetic information encoding the characteristic of interest.

Preferably, the characteristic of interest is a quantitative trait of interest (QTL).

According to another aspect, the present invention relates to a fusion protein comprising a Cas9 domain and a Spo11 domain as described above.

The present invention also concerns a nucleic acid encoding said fusion protein according to the invention.

The nucleic acid according to the invention can be in the form of single-stranded or double-stranded DNA and/or RNA. According to a preferred embodiment, the nucleic acid is an isolated DNA molecule, synthesized by recombinant techniques well-known to a person skilled in the art. The nucleic acid according to the invention can be deduced from the sequence of the fusion protein according to the invention and the use of codons may be appropriate according to the host cell in which the nucleic acid must be transcribed.

The present invention further concerns an expression cassette comprising a nucleic acid according to the invention operably linked to the sequences necessary to its expression. Notably, the nucleic acid can be under the control of a promoter allowing its expression in a host cell. Generally, an expression cassette comprises, or consists of, a promoter for initiating transcription, a nucleic acid according to the invention, and a transcription terminator.

The term "expression cassette" refers to a nucleic acid construction comprising a coding region and a regulatory region, operably linked. The expression "operably linked" indicates that the elements are combined so that the expression of the coding sequence is under the control of the transcriptional promoter. Typically, the promoter sequence is placed upstream of the gene of interest, at a distance therefrom compatible with control of its expression. Spacer sequences may be present, between the regulatory elements and the gene, since they do not prevent the expression. The expression cassette may also comprise at least one activating sequence ("enhancer") operably linked to the promoter.

A wide variety of promoters that can be used for the expression of genes of interest in host cells or organisms are at the disposal of a person skilled in the art. They include constitutive promoters as well as inducible promoters which are activated or suppressed by exogenous physical or chemical stimuli.

Preferably, the nucleic acid according to the invention is placed under the control of a constitutive promoter or a meiosis-specific promoter.

Exemplary meiosis-specific promoters that can be used in the context of the present invention include, but are not limited to, endogenous Spo11 promoters, promoters of the Spo11 partners for forming double-strand breaks, the Rec8 promoter (Murakami & Nicolas, 2009, Mol. Cell. Biol, 29, 3500-16), or the Spo13 promoter (Malkova et al., 1996, Genetics, 143, 741-754).

Other inducible promoters may also be used such as the estradiol promoter (Carlile & Amon, 2008 Cell, 133, 280-91), the methionine promoter (Care et al., 1999, Molecular Microb 34, 792-798), promoters induced by heat-shock, metals, steroids, antibiotics and alcohol.

The constitutive promoters that can be used in the context of the present invention are, by way of nonlimiting examples: the cytomegalovirus (CMV) immediate-early gene promoter, the simian virus (SV40) promoter, the adenovirus major late promoter, the Rous sarcoma virus (RSV) promoter, the mouse mammary tumor virus (MMTV) promoter, the phosphoglycerate kinase (PGK) promoter, the elongation factor ED1-alpha promoter, ubiquitin promoters, actin promoters, tubulin promoters, immunoglobulin promoters, alcohol dehydrogenase 1 (ADH1) promoter, RNA polymerase III-dependent promoters such as the U6, U3, H1, 7SL, pRPR1 ("Ribonuclease P RNA 1"), SNR52 ("small nuclear RNA 52") promoters, or the promoter pZmUbi.

The transcription terminator can be readily selected by a person skilled in the art. Preferably, this terminator is RPR1t, the 3' flanking sequence of the *Saccharomyces cerevisiae* SUP4 gene or the nopaline synthase terminator (tNOS).

The present invention further concerns an expression vector comprising a nucleic acid or an expression cassette according to the invention. This expression vector can be used to transform a host cell and to express the nucleic acid according to the invention in said cell. The vectors can be constructed by conventional molecular biology techniques, well-known to a person skilled in the art.

Advantageously, the expression vector comprises regulatory elements for expressing the nucleic acid according to the invention. These elements may comprise for example transcription promoters, transcription activators, terminator sequences, initiation codons and termination codons. The methods for selecting these elements as a function of the host cell in which the expression is desired are well-known to a person skilled in the art.

In a particular embodiment, the expression vector comprises a nucleic acid encoding the fusion protein according to the invention, placed under the control of a constitutive promoter, preferably the ADH1 promoter (pADH1). It may also comprise a terminator sequence such as the ADH1 terminator (tADH1).

The expression vector may comprise one or more bacterial or eukaryotic origins of replication. The expression vector may in particular include a bacterial origin of replication functional in *E. coli* such as the ColE1 origin of replication. Alternatively, the vector may comprise a eukaryotic origin of replication, preferably functional in *S. cerevisiae*.

The vector may further comprise elements allowing its selection in a bacterial or eukaryotic host cell such as, for example, an antibiotic-resistance gene or a selection gene ensuring the complementation of the respective gene deleted in the host-cell genome. Such elements are well-known to a person skilled in the art and are extensively described in the literature.

In a particular embodiment, the expression vector comprises one or more antibiotic resistance genes, preferably a gene for resistance to ampicillin, kanamycin, hygromycin, geneticin and/or nourseothricin.

The expression vector may also comprise one or more sequences allowing targeted insertion of the vector, the expression cassette or the nucleic acid in the genome of a host cell. Preferably, the insertion is carried out at a gene whose inactivation allows the selection of the host cells having integrated the vector, the cassette or the nucleic acid, such as the TRP1 locus.

The vector may be circular or linear, single or double-stranded. It is advantageously selected from plasmids, phages, phagemids, viruses, cosmids and artificial chromosomes. Preferably, the vector is a plasmid.

The present invention concerns in particular a vector, preferably a plasmid, comprising a bacterial origin of replication, preferably the ColE1 origin, a nucleic acid as defined above under the control of a promoter, preferably a constitutive promoter such as the ADH1 promoter, a terminator, preferably the ADH1 terminator, one or more selection markers, preferably resistance markers such as the gene for resistance to kanamycin or to ampicillin, and one or more sequences allowing targeted insertion of the vector, the expression cassette or the nucleic acid into the host-cell genome, preferably at the TRP1 locus of the genome of a yeast.

In a particular embodiment, the nucleic acid according to the invention carried by the vector encodes a fusion protein comprising one or more tags, preferably comprising a tag consisting of six histidines and/or one or more Flag motifs, preferably three Flag motifs. Preferably the tag or tags are C-terminal.

According to a particular embodiment the expression vector is the plasmid P1 having the nucleotide sequence SEQ ID NO: 1 or the plasmid P2 having the nucleotide sequence SEQ ID NO: 2.

The present invention also concerns the use of a nucleic acid, an expression cassette or an expression vector according to the invention to transform or transfect a cell. The host cell may be transformed/transfected in a transient or stable manner and the nucleic acid, the cassette or the vector may be contained in the cell as an episome or integrated into the host-cell genome.

The present invention concerns a host cell comprising a fusion protein, a nucleic acid, an expression cassette or an expression vector according to the invention.

Preferably, the cell is a eukaryotic cell, in particular a yeast, plant, fungal or animal cell. Particularly preferably, the host cell is a yeast cell. In a particular embodiment, the host cell is nonhuman and/or nonembryonic.

According to a particular embodiment, the eukaryotic cell is a yeast cell, in particular a yeast of industrial interest. Exemplary yeasts of interest include, but are not limited to, yeasts of the genus *Saccharomyces sensu stricto, Schizosaccharomyces, Yarrowia, Hansenula, Kluyveromyces, Pichia* or *Candida*, as well as the hybrids obtained from a strain belonging to one of these genera.

Preferably, the yeast of interest belongs to the genus *Saccharomyces*, preferably a yeast selected from the group consisting of *Saccharomyces cerevisiae, Saccharomyces bayanus, Saccharomyces castelli, Saccharomyces eubayanus, Saccharomyces kluyveri, Saccharomyces kudriavzevii, Saccharomyces mikatae, Saccharomyces uvarum, Saccharomyces paradoxus, Saccharomyces pastorianus* (also called *Saccharomyces carlsbergensis*), and the hybrids obtained from at least one strain belonging to one of these species, more preferably said eukaryotic host cell is *Saccharomyces cerevisiae*.

According to another particular embodiment, the eukaryotic cell is a fungal cell, in particular a fungal cell of industrial interest. Exemplary fungi include, but are not limited to, filamentous fungal cells. Filamentous fungi include fungi belonging to the subdivisions Eumycota and Oomycota. The filamentous fungal cells may be selected from the group consisting of *Trichoderma, Acremonium, Aspergillus, Aureobasidium, Bjerkandera, Ceriporiopsis, Chrysosporium, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium* or *Trametes* cells.

In another preferred embodiment, the cell is a plant cell, preferably a plant cell selected from the group consisting of rice, wheat, soy, maize, tomato, *Arabidopsis thaliana*, barley, rapeseed, cotton, sugarcane and beet, more preferably said eukaryotic host cell is a rice cell.

The present invention also concerns the use of the fusion protein, the nucleic acid, the expression cassette or the expression vector according to the invention to (i) induce targeted meiotic recombinations in a eukaryotic cell, (ii) generate variants of a eukaryotic organism, and/or (iii) identify or locate the genetic information encoding a characteristic of interest in a eukaryotic cell genome.

The present invention further concerns a kit comprising a fusion protein, a nucleic acid, an expression cassette or an expression vector according to the invention, or a host cell transformed or transfected with a nucleic acid, an expression cassette or an expression vector according to the invention. It also concerns the use of said kit to implement a method according to the invention, in particular to (i) induce targeted meiotic recombinations in a eukaryotic cell, (ii) generate variants of a eukaryotic organism, and/or (iii) identify or locate the genetic information encoding a characteristic of interest in a eukaryotic cell genome.

The methods according to the invention may be in vitro, in vivo or ex vivo methods.

The following examples are presented for illustrative and nonlimiting purposes.

EXAMPLES

1. Design, Synthesis and Cloning of a Nucleotide Sequence Encoding the SpCas9 Protein and its Nuclease-Deficient Form SpCas9*.

The SpCas9 gene encoding the Cas9 protein comes from the bacterial strain *Streptococcus pyogenes*. The catalytically inactive form of SpCas9 (SpCas9*) is distinguished from that of SpCas9 by two point mutations: the aspartate at position 10 and the histidine at position 840 have both been substituted by alanines ($Asp^{10} \rightarrow Ala^{10}$ and $His^{840} \rightarrow Ala^{840}$.

Because of variations in the frequency of use of genetic codons between *Streptococcus pyogenes* and *Saccharomyces cerevisiae*, the SpCas9 and SpCas9* gene sequences were adapted in order to optimize their expression in yeast (yeast_optim_SpCas9 and yeast_optim_SpCas9*). The amino acid sequences of the two proteins were not modified.

2. Engineering of the Sequences Yeast_Optim_SpCas9 and Yeast_Optim_SpCas9* in Order to Fuse the SpCas9 and SpCas9* Proteins with the Meiotic Transesterase Spo11.

Engineering of the yeast_optim_SpCas9 and yeast_optim_SpCas9* sequences made it possible to fuse the SpCas9 and SpCas9* proteins with a nuclear localization signal (NLS) associated with an N-terminal inker (linker 1) and with a second C-terminus linker (linker 2) (which will separate the SpCas9 and SpCas9* proteins from the Spo11 protein in the final construction). The nucleotide sequences thus obtained and encoding the protein sequences NLS linker1-SpCas9-linker2 and NLS-linker1-SpCas9*-linker2 were then cloned into an integrative plasmid, containing the complete form of the Spo11 protein from *Saccharomyces cerevisiae* tagged with a sequence encoding the C-terminal double 6×His-3×Flag motif and whose expression is controlled by the constitutive promoter pADH1. The resulting plasmid constructions, P1 and P2, thus contained in-phase fusion of the N-terminus of NLS-linker 1 SpCas9-linker2 and NLS-linker1-SpCas9*-linker2 to the Spo11 protein. Consequently, P1 and P2 respectively allowed the constitutive expression in yeast of the NLS-SpCas9-Spo11-6×His- 3×Flag (SEQ ID NO: 6) and NLS-SpCas9*-Spo11-6×His-3×Flag (SEQ ID NO: 7) fusion proteins (FIG. 1).

3. Engineering of Single and Multiple Guide RNA Expression Vectors.

Starting with a 2 micron (4) plasmid (Farzadfard F et al., 2013, ACS Synth. Biol., 2, pp. 604-613; DiCarlo J E et al., 2013, Nucleic Acids Res., 41(7), pp. 4336-4343) containing the handle region (82 nucleotides) of a guide RNA (gRNA), placed under the control of a constitutive RNA polymerase III-dependent promoter such as pRPR1 or SNR52, the expression vector for a single 102-nucleotide gRNA was constructed by cloning the 20-nucleotide specificity-determining sequence (SDS region) of the gRNA at a restriction site located immediately 5' of the sequence encoding the handle region of the linearized vector, by the Gibson assembly method (FIG. 2A).

This expression vector contained a sequence comprising numerous unique restriction sites (multiple cloning site (MCS)) downstream of the terminator (RPR1t or 3' flanking sequence of SUP4). Also, in order to obtain a system allowing multiplexed targeting of meiotic recombination sites, several gRNA expression cassettes were inserted into the expression vector at its MCS. The gRNA expression cassettes consist of a constitutive RNA polymerase III-dependent promoter (pRPR1 or SNR52), the specific gRNA and a terminator (RPR1t or the 3' flanking sequence of SUP4). These gRNA expression cassettes were first cloned into unique gRNA expression vectors (see above), then were amplified by PCR before being cloned successively into the multiple cloning site (MCS) of the expression vector for a single gRNA by conventional insertion/ligation techniques (FIG. 2B). This strategy ends up in concatenating several gRNA cassettes into a single expression vector.

4. Co-Expression of SpCas9-Spo11 and SpCas9*-Spo11 Fusion Proteins with gRNAs in Yeast.

In order to introduce the NLS-SpCas9-Spo11 or NLS-SpCas9*-Spo11 fusions into the chromosomal TRP1 locus, strains of the yeast *Saccharomyces cerevisiae* were transformed by heat shock with the linearized vectors P1 or P2. These fusion proteins, carrying the C-terminal 3×Flag tag, were placed under the control of the constitutive ADH1 promoter. After transformation, the cells were plated on Petri dishes containing selective medium (adapted to the selection markers carried by the plasmids P1 and P2) in order to select the transformants having integrated the fusion into their genome.

The expression vector for the gRNA(s) was then introduced into diploid yeast strains expressing the NLS-SpCas9-Spo11 or NLS-SpCas9*-Spo11 fusion proteins by heat-shock transformation. The cells were then plated on medium selective for the selection markers for the gRNA expression plasmids. The gRNA expression plasmids comprised a 2 micron (2µ) origin of replication which enabled them to be maintained with a high copy number in each yeast cell (50-100 copies/cell).

The formation of meiotic double-strand breaks generated in a single or multiplexed manner by the SpCas9-Spo11 or SpCas9*-Spo11 fusion proteins at the genomic sites targeted by single or multiple gRNAs is then detected by Southern Blot analysis of genomic DNA extracted from diploid cells grown in sporulation medium.

5. Complementation of Spores Derived from Sporulation of SPO11 Gene-Inactivated Strains by the Expression of the SpCas9*-Spo11 Fusion Protein The inventors analyzed the viability of spores derived from meiosis of the following diploid strains of *Saccharomyces cerevisiae*:

a SPO11/SPO11 strain (ORD7339) comprising two copies of the wild-type allele of the SPO11 gene, a spo11/spo11 strain (AND2822) comprising two copies of the mutated allele of the SPO11 gene. This mutated allele corresponds to the wild-type allele in which a genetic marker totally inactivating the gene was inserted, a spo11/spo11 dCAS9-SPO11/0 strain (AND2820) comprising two copies of the mutated allele of the SPO11 gene and one copy of the gene encoding the SpCas9*-Spo11 fusion protein integrated into one of the two copies of chromosome IV into the TRP1 locus, and a spo11/spo11 dCAS9-SPO11/dCAS-9-SPO11 strain (AND2823) comprising two copies of the mutated allele of the SPO11 gene and two copies of the gene encoding the SpCas9*-Spo11 fusion protein integrated into both copies of chromosome IV into the TRP1 locus.

Figure 5:
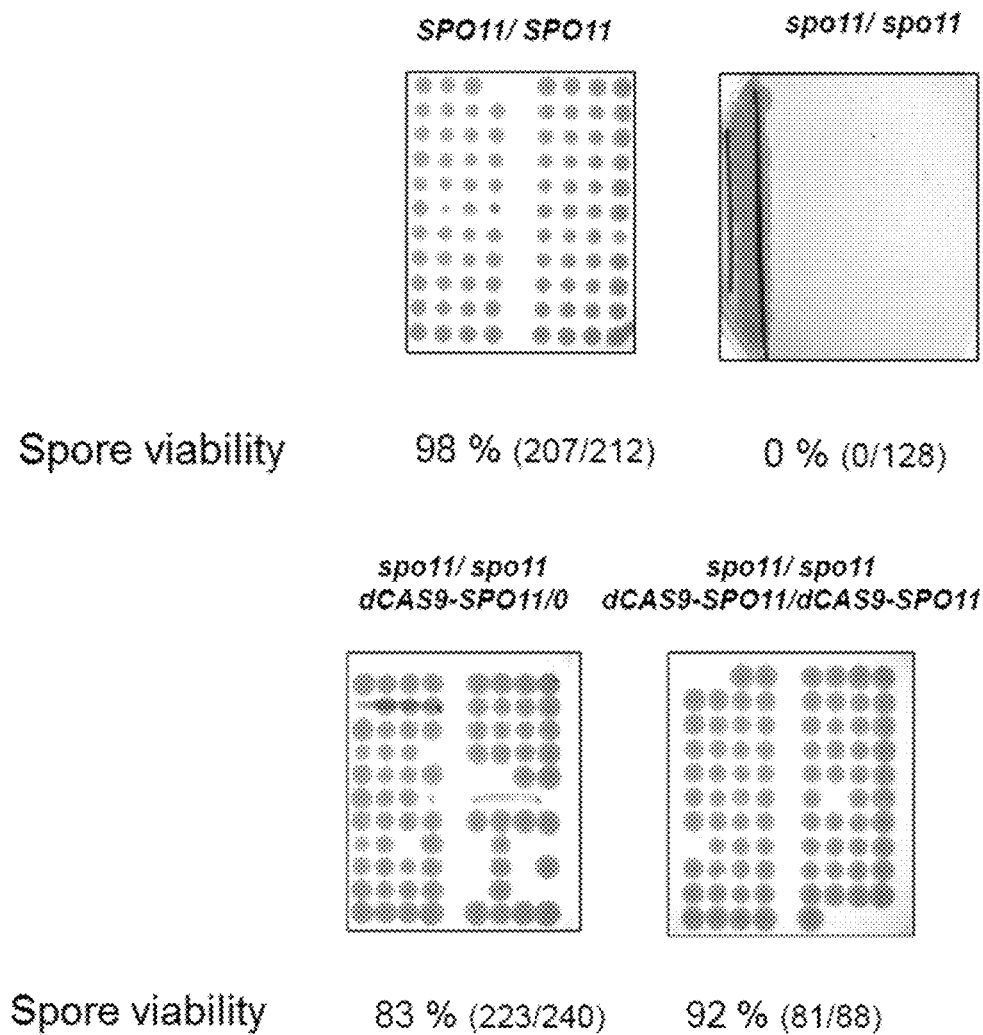
FIG. 5: Viability of spores derived from sporulation of strains expressing or not expressing the SpCas9*-Spo11 fusion protein. Growth of spores derived from meiosis of the diploid strains SPO11/SPO11 (ORD7339), spo11/spo11 (AND2822), spo11/spo11 dCAS9-SPO11/0 (AND2820) and spo11/spo11 dCAS9-SPO11/dCAS-9-SPO11 (AND2823).

The results presented in FIG. 5 show that the expression of the SpCas9*-Spo11 fusion protein complements the inviability of spores derived from sporulation of SPO11 gene-inactivated strains.

6. Targeting of Meiotic Double-Strand Breaks by the SpCas9*-Spo11 Fusion Protein and a Guide RNA Specific for the YCR048W Region The SpCas9*-Spo11 expression cassette (dCAS9-SPO11) was integrated into the chromosomal TRP1 locus (chromosome IV). The UAS1-YCR048W guide RNA (sgRNA) (SEQ ID NO: 10) was expressed by the multicopy replicative (non-integrative) plasmid as described in FIG. 2A. The fusion gene carrying the dCAS9-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the dCAS9-SPO11 construction was confirmed by Southern blot.

The following strains were used:
SPO11/SPO11 (ORD7304),
SPO11/SPO11 expressing the UAS1-YCR48W guide RNA (sgRNA) (ANT2524),
spo11/spo11 dCAS9-SPO11/0 expressing the guide RNA handle, i.e., a guide RNA without the SDS region which is specific for the chromosomal target (ANT2527),
spo11/spo11 dCAS9-SPO11/0 expressing the UAS1-YCR48W guide RNA (sgRNA) (ANT2528), and
spo11/spo11 dCAS9-SPO11/dCAS9-SPO11 expressing the UAS1-YCR48W guide RNA (sgRNA) (ANT2529).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after genomic DNA digestion by the restriction enzyme AseI. The DNA was probed with a fragment internal to the YCR048W locus. The bands were quantified using the ImageJ software.

Figure 6:
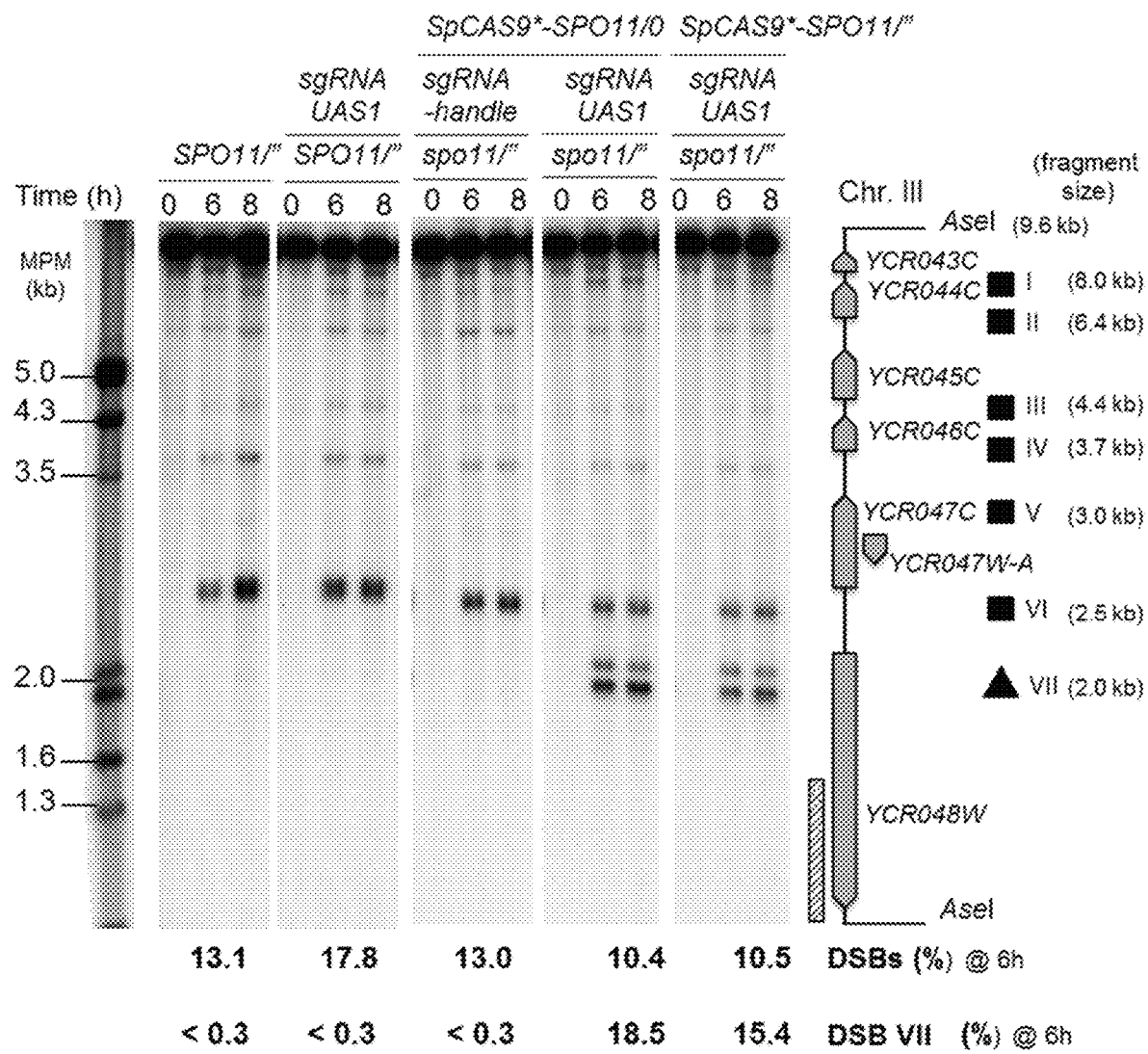
FIG. 6: Targeting of meiotic DSBs by the SpCas9*-Spo11 fusion protein and a guide RNA specific for the YCR048W region. On the right of the gel, a chart indicates the position of the genes (coding regions, gray arrows) and the position of the probe. The black squares indicate the natural DSB sites. The black triangle indicates the DSB sites targeted by the UAS1 YCR048W guide RNA. The percentage of DSBs corresponds to the ratio between the signal intensity of the fragment concerned and the total signal of the lane.

The results presented in FIG. 6 show that the expression of the SpCas9*-Spo11 construction (dCAS9-SPO11) induces meiotic DNA double-strand breaks (DSBs) at the natural cleavage sites of the Spo11 protein (YCR043C-YCR048W region of chromosome III (DSBs I to VI symbolized by black squares in FIG. 6) and at the UAS1 site (DSB VII, black triangle) targeted by the UAS1-YCR048W guide RNA and located in the coding region of the YCR048W gene.

7. Targeting of Meiotic Double-Strand Breaks by the SpCas9*-Spo11 Fusion Protein and a Guide RNA Specific for the YCR048W Region The SpCas9*-Spo11 expression cassette (dCAS9-SPO11) was integrated into the chromosomal TRP1 locus (chromosome IV). The UAS1-YCR048W or UAS2-YCR048W (SEQ ID NO: 11) guide RNA (sgRNA) was expressed by the multicopy replicative (non integrative) plasmid as described in FIG. 2A. The fusion gene carrying the dCAS9-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the dCAS-9-SPO11 construction was confirmed by Southern blot.

The following strains were used:
SPO11/SPO11 (ORD7304),
SPO11/SPO11 expressing the UAS1-YCR048W guide RNA (sgRNA) (ANT2524),
SPO11/SPO11 dCAS9-SPO11/0 expressing the guide RNA handle, i.e., a guide RNA without the SDS region which is specific for the chromosomal target (ANT2518),
SPO11/SPO11 dCAS9-SPO11/0 expressing the UAS1-YCR048W guide RNA (sgRNA) (ANT2519),
SPO11/SPO11 dCAS9-SPO11/dCAS-9-SPO11 expressing the UAS1-YCR48W guide RNA (sgRNA) (ANT2522),
SPO11/SPO11 dCAS9-SPO11/0 expressing the UAS2-YCR048W guide RNA (sgRNA) (ANT2520),
SPO11/SPO11 dCAS9-SPO11/dCAS-9-SPO11 expressing the UAS2-YCR048W guide RNA (sgRNA) (ANT2523), and
spo11/spo11 dCAS9-SPO11/0 expressing the UAS1-YCR048W guide RNA (sgRNA) (ANT2528).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after digestion of genomic DNA by the restriction enzymes AseI and SacI. The DNA was probed with a fragment internal to the YCR048W locus. The bands were quantified using the ImageJ software.

Figure 7:
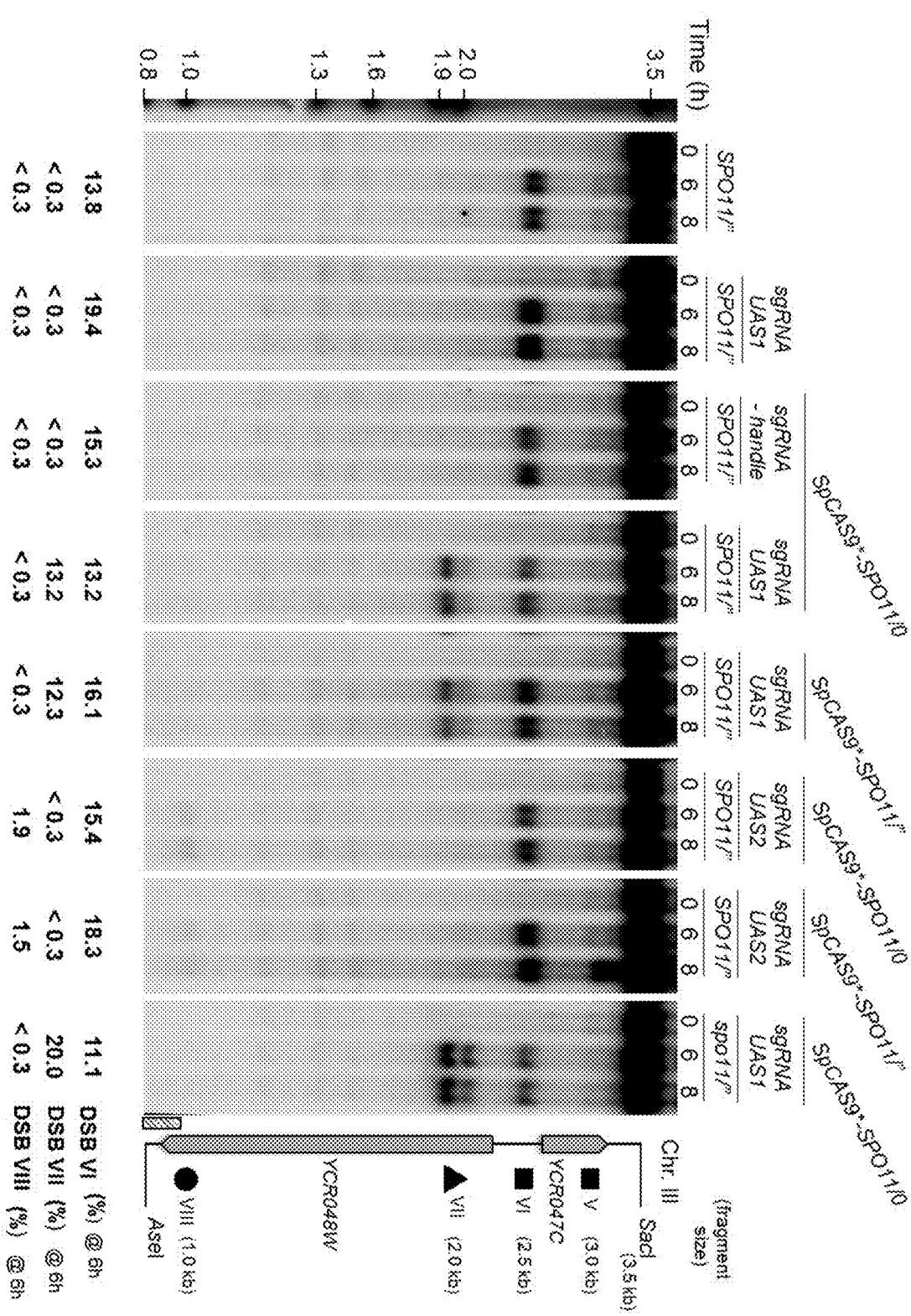
FIG. 7: Targeting of meiotic DSBs by the SpCas9*-Spo11 fusion protein and two guide RNAs specific for the YCR048W region. On the right of the gel, a chart indicates the position of the genes (coding regions, gray arrows) and the position of the probe. The black squares indicate the natural DSB sites. The black triangle indicates the DSB sites targeted by the UAS1-YCR048W guide RNA. The black circle indicates the DSB sites targeted by the UAS2-YCR048W guide RNA. The percentage of DSBs corresponds to the ratio between the signal intensity of the fragment concerned and the total signal of the lane.

The results presented in FIG. 7 indicate that the expression of the dCAS-9-SPO11 construction induces meiotic DNA double-strand breaks (DSBs) at the natural cleavage sites of the Spo11 protein (YCR047C-YCR048W region of chromosome III (DSBs V and VI symbolized by squares) and at the UAS1-YCR048W site (DSB VII symbolized by a triangle) targeted by the UAS1-YCR048W guide RNA in the 5' coding region of the YCR048W gene and at the UAS2 YCR048W site (DSB VIII symbolized by a circle) targeted by the UAS2-YCR048W guide RNA in the 3' coding region of the YCR048W gene. These results show that the targeting is effective in the strains carrying the wild-type SPO11 gene or the mutated spo11 gene.

8. Targeting of Meiotic Double-Strand Breaks by the SpCas9*-Spo11 Fusion Protein and a Guide RNA Specific for the GAL2 Region The SpCas9*-Spo11 expression cassette (dCAS9-SPO11) was integrated into the chromosomal TRP1 locus (chromosome IV). The UAS D/E-GAL2 guide RNA (sgRNA) (SEQ ID NO: 12) was expressed by the multicopy replicative (non-integrative) plasmid as described in FIG. 2A. The fusion gene carrying the dCAS9-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the dCAS9-SPO11 construction was confirmed by Southern blot.

The following strains were used:
SPO11/SPO11 (ORD7304),
spo11/spo11 GAL4/GAL4 dCAS9-SPO11/0 expressing the guide RNA handle, i.e., a guide RNA without the SDS region which is specific for the chromosomal target (ANT2527),
spo11/spo11 gal4/gal4 dCAS9-SPO11/0 expressing the guide RNA handle (ANT2536) (both alleles of the GAL4 gene are mutated and thus inactive),
spo11/spo11 GAL4/GAL4 dCAS9-SPO11/0 expressing the UAS D/E-GAL2 guide RNA (ANT2530), and
spo11/spo11 gal4/gal4 dCAS9-SPO11/0 expressing the UAS D/E-GAL2 guide RNA (ANT2533).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after digestion of genomic DNA by the restriction enzyme XbaI. The DNA was probed with the terminal portion of the GAL2 gene. The bands were quantified using the ImageJ software.

Figure 8:
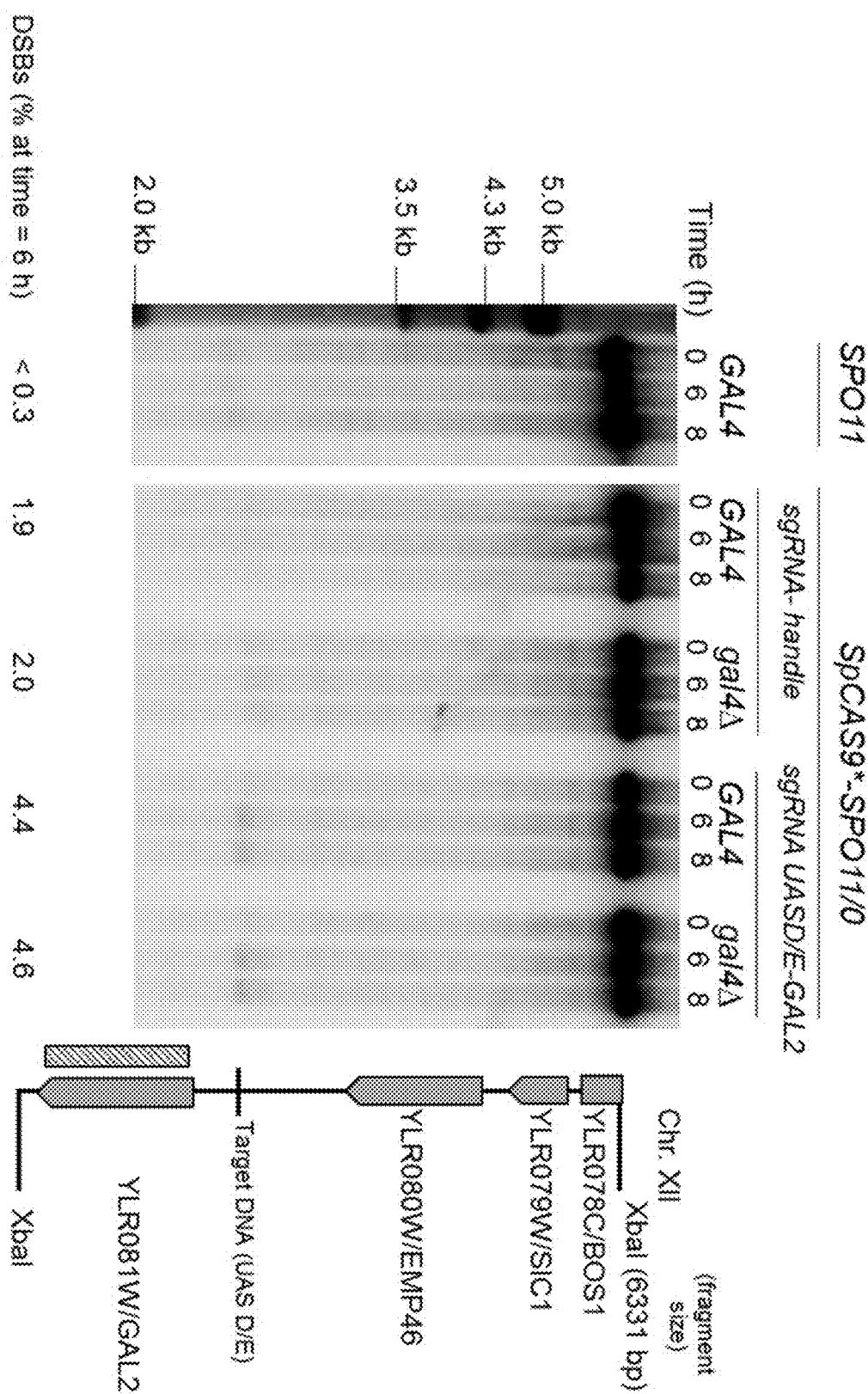
FIG. 8: Targeting of meiotic DSBs by the SpCas9*-Spo11 fusion protein and a guide RNA specific for the GAL2 region. On the right of the gel, a chart indicates the position of the genes (coding regions, gray arrows) and the position of the probe. The percentage of DSBs corresponds to the ratio between the signal intensity of the fragment concerned and the total signal of the lane.

The results presented in FIG. 8 show that the expression of the dCAS9-SPO11 construction induces meiotic DNA double-strand breaks (DSBs) at the UAS D/E site of the GAL2 gene promoter targeted by the UAS D/E-GAL2 guide RNA.

9. Targeting of Meiotic Double-Strand Breaks by the SpCas9*-Spo11 Fusion Protein and a Guide RNA Specific for the SWC3 Region The SpCAS9*-SPO11 expression cassette (dCas9-SPO11) was integrated into the chromosomal TRP1 locus (chromosome IV). The SWC3 guide RNA ($sgRNA_{SWC3}$) (SEQ ID NO: 13) was expressed by the multicopy replicative (non-integrative) plasmid as described above (FIG. 2A). The fusion gene carrying the SpCAS9*-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the SpCAS9*-SPO11 construction was confirmed by Southern blot.

The following strains were used:
SPO11/SPO11 (ORD7304),
spo11/spo11 SpCAS9*-SPO11/0 expressing the guide RNA handle, i.e., a guide RNA without the SDS region which is specific for the chromosomal target (ANT2527),
spo11/spo11 SpCAS9*-SPO11/0 expressing the SWC3 guide RNA ($sgRNA_{SWC3}$) (ANT2564).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after digestion of genomic DNA by the restriction enzymes PacI and AvrII. The DNA was probed with a fragment internal to the SPOT locus. The bands were quantified using the ImageJ software.

Figure 9:
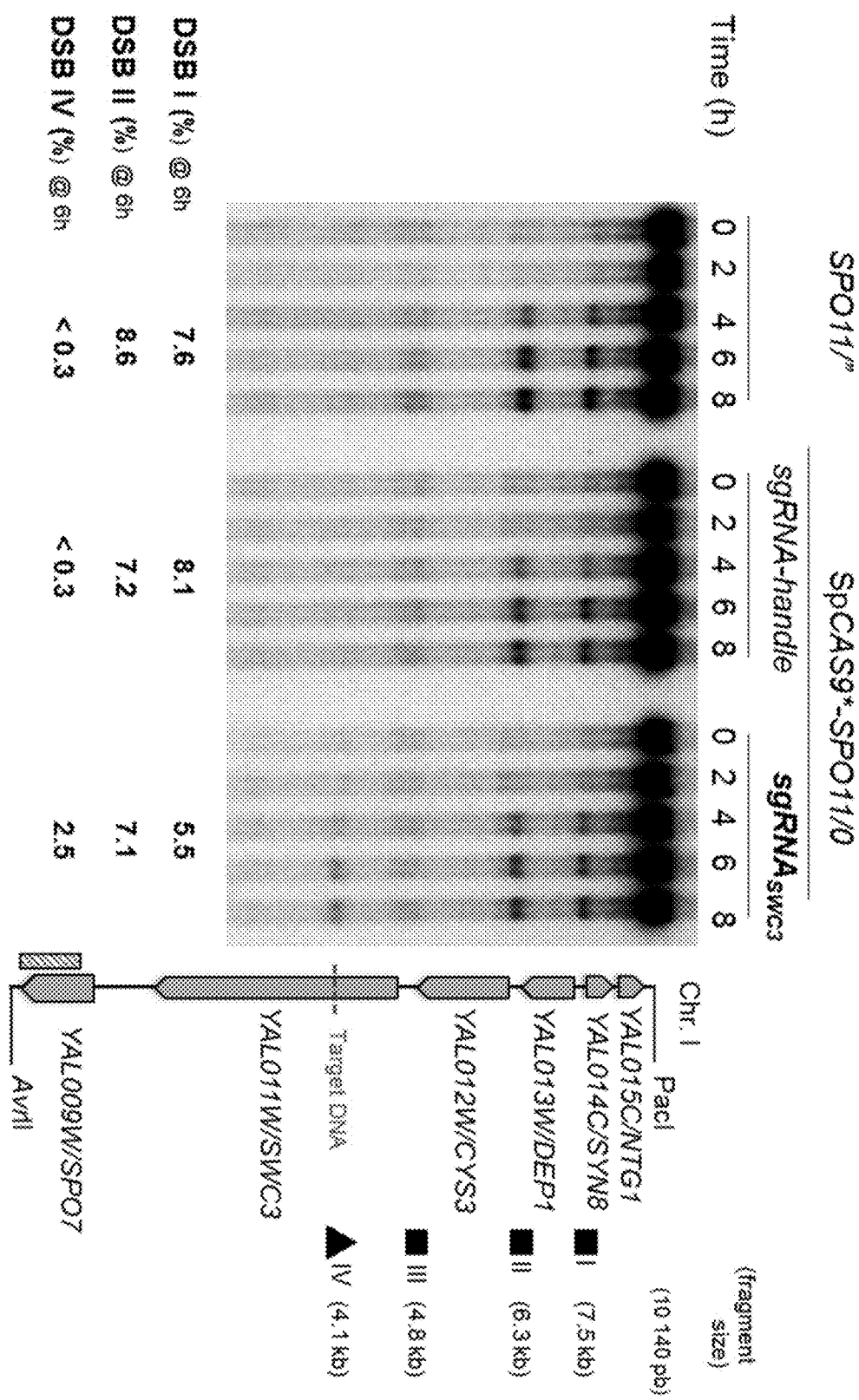
FIG. 9: Targeting of meiotic DSBs by the SpCas9*-Spo11 fusion protein and a guide RNA specific for the SWC3 region. On the right of the gel, a chart indicates the position of the genes (coding regions, gray arrows) and the position of the probe (hatched rectangle). The percentage of DSBs corresponds to the ratio between the signal intensity of the fragment concerned and the total signal of the lane.

The results presented in FIG. 9 show that the expression of the SpCAS9*-Spo11 construction induces meiotic DNA double-strand breaks (DSBs) at the natural cleavage sites of the Spo11 protein (SIN8-SWC3 region) of chromosome I (DSBs I, II and III symbolized by black squares in FIG. 9) and at the target site (DSBs IV symbolized by a circle) by the SWC3 guide RNA (sgRNA$_{SWC3}$) and located in the coding region of the SWC3 gene.

10. Targeting of Meiotic DNA Double-Strand Breaks by the SpCas9*-Spo11 Protein and Several Multiplexed RNA Guides Specific for the GAL2 Region The SpCAS9*-Spo11 expression cassette (dCas9-SPO11) was integrated into the chromosomal TRP1 locus (chromosome IV). The UAS-A guide RNA (sgRNA$_{UAS-A}$) (SEQ ID NO: 14), UAS-B guide RNA (sgRNA$_{UAS-B}$) (SEQ ID NO: 15) and UAS-D/E guide RNA (sgRNA$_{UAS-D/E}$) (SEQ ID NO: 12) were expressed individually and in multiplex (Multi gRNAs) by the multicopy replicative (non-integrative) plasmid as described above (FIG. 2A). The fusion gene carrying the SpCAS9*-SPO11 construction was expressed under the control of the constitutive ADH1 promoter. The guide RNAs were expressed under the control of the constitutive RPR1 promoter. The yeast cells were transformed by the conventional electroporation method. The integration of the cassette carrying the SpCAS9*-SPO11 construction was confirmed by Southern blot.

The following strains were used:
spo11/spo11 GAL4/GAL4 SpCAS9*-SPO11/0 expressing the guide RNA handle, i.e., a guide RNA without the SDS region which is specific for the chromosomal target (ANT2527),
spo11/spo11 GAL4/GAL4 SpCAS9*-SPO11/0 expressing the UAS-A guide RNA (sgRNA$_{UAS-A}$) (ANT2532),
spo11/spo11 gal4/gal4 SpCAS9*-SPO11/0 expressing the UAS-A guide RNA (sgRNA$_{UAS-A}$) (ANT2534),
spo11/spo11 GAL4/GAL4 SpCAS9*-SPO11/0 expressing the UAS-D/E guide RNA (sgRNA$_{UAS-D/E}$) (ANT2530),
spo11/spo11 gal4/gal4 SpCAS9*-SPO11/0 expressing the UAS-D/E guide RNA (sgRNA$_{UAS-D/E}$) (ANT2533),
spo11/spo11 GAL4/GAL4 SpCAS9*-SPO11/0 expressing in multiplex the UAS-A guide RNA (sgRNA$_{UAS-A}$), the UAS-B guide RNA (sgRNA$_{UAS-B}$) and the UAS-D/E guide RNA (sgRNA$_{UAS-D/E}$) (MultigRNAs) (ANT2551),
spo11/spo11 gal4/gal4 SpCAS9*-SPO11/0 expressing in multiplex the UAS-A guide RNA (sgRNA$_{UAS-A}$), the UAS-B guide RNA (sgRNA$_{UAS-B}$) and the UAS-D/E guide RNA (sgRNA$_{UAS-D/E}$) (MultigRNAs) (ANT2552).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after digestion of genomic DNA by the restriction enzyme XbaI. The DNA was probed with the terminal portion of the GAL2 gene. The bands were quantified using the ImageJ software.

Figure 10:
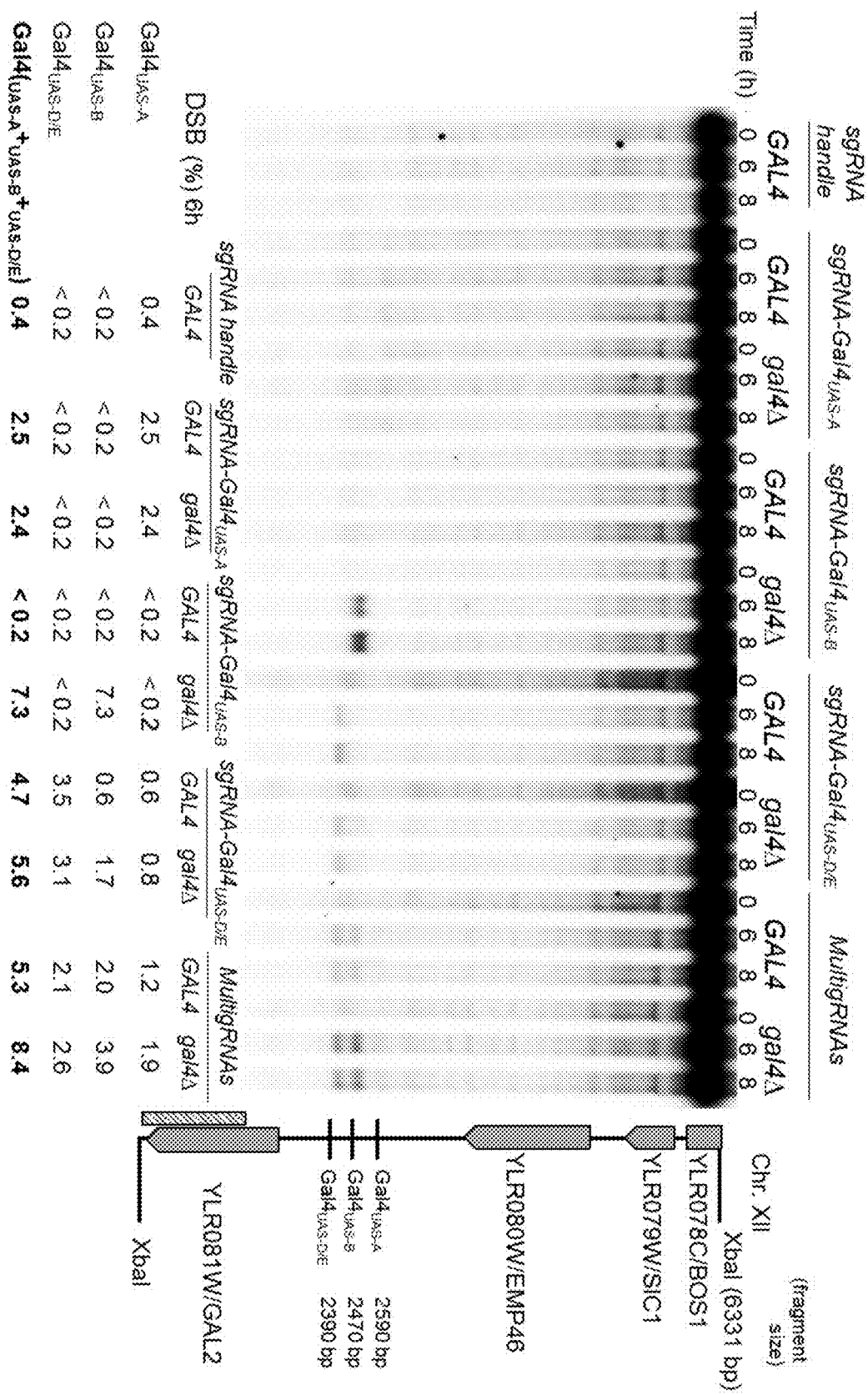
FIG. 10: Multiplexed targeting of meiotic DSBs by the SpCas9*-Spo11 fusion protein and several guide RNAs specific for the GAL2 region. On the right of the gel, a chart indicates the position of the genes (coding regions, gray arrows) and the position of the probe (hatched rectangle). The percentage of DSBs corresponds to the ratio between the signal intensity of the fragment concerned and the total signal of the lane.

The results presented in FIG. 10 indicate that the expression of the SpCAS9*-Spo11 construction (dCas9-SPO11) induces meiotic DNA double-strand breaks (DSBs) at the target sites in the GAL2 gene promoter on chromosome XII by the guide RNA(s). In particular, the co expression of SpCas9*-Spo11 with the individual sgRNAs sgRNA$_{UAS-A}$ and sgRNA$_{UAS-D/E}$ leads to the generation of DSBs, respectively, at the UAS-A and UAS-D/E sites. Interestingly, the targeting of SpCas9*-Spo11 by the co-expression of sgRNA$_{UAS-A}$, sgRNA$_{UAS-B}$ and sgRNA$_{UAS}$-D/E leads to the formation of multiplex DSBs at the various target sites.

Figure 11:
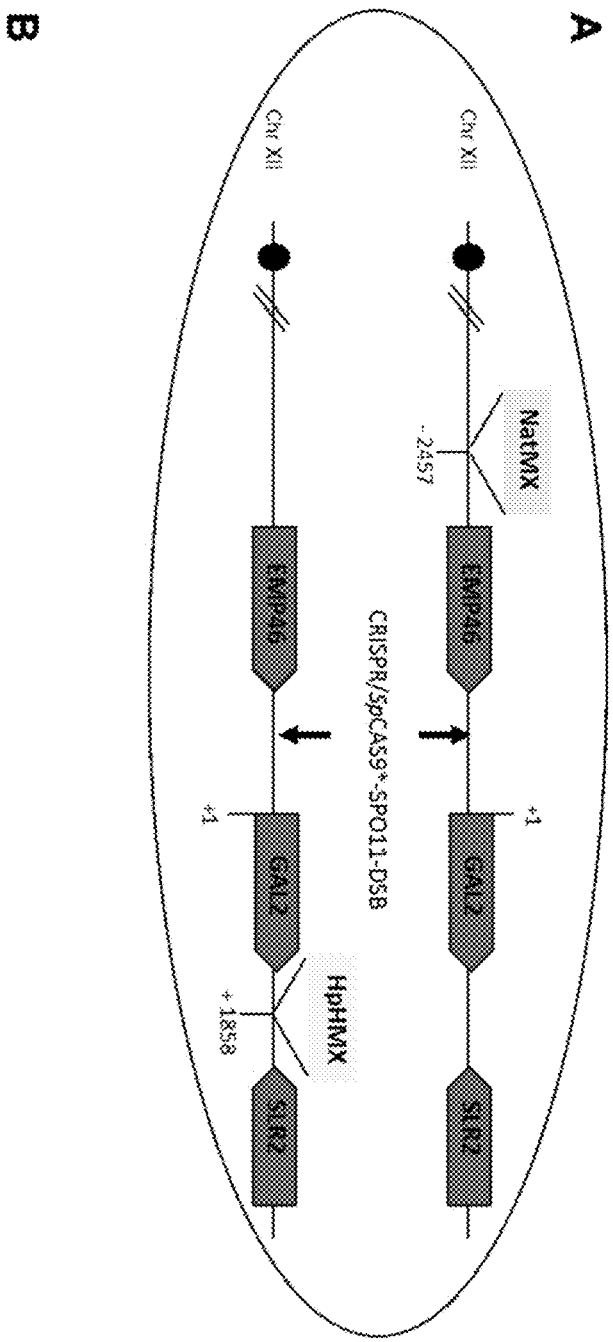
FIG. 11: Stimulation of meiotic recombination by the SpCas9*-SPO11 protein and a guide RNA in the GAL2 target region. (A) Diagram of the genetic test for detecting recombinants at the GAL2 site. (B) Test for genetic recombination at the GAL2 locus.

11. Stimulation of Meiotic Recombination by the SpCas9*-SPO11 Protein and Several Multiplexed Guide RNAs in the GAL2 Target Region In order to detect the crossovers induced by the expression of CRISPR/SpCas9*-Spo11, the NatMX and HphMX cassettes (which respectively confer resistance to nourseothricin and to hygromycin) were trans inserted upstream and downstream of the GAL2 gene in diploid cells (see FIG. 11A).

The SpCAS9*-Spo11 expression cassette (dCAS9-SPO11) was integrated into the chromosomal TRP1 locus (chromosome IV). The UAS-D/E guide RNA (sgRNA$_{UAS-D/E}$) (SEQ ID NO: 12) was expressed by the multicopy replicative (non-integrative) plasmid as described above (FIG. 2A). The multiplex expression of the UAS-A guide RNA (sgRNA$_{UAS-A}$) (SEQ ID NO: 14), the UAS-B guide RNA (sgRNA$_{UAS-B}$) (SEQ ID NO: 15) and the UAS-D/E guide RNA (sgRNA$_{UAS-D/E}$) (SEQ ID NO: 12) was carried out from the same guide RNA expression plasmid described above (Multi gRNAs). The fusion gene carrying the SpCAS9*-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the SpCAS9*-SPO11 construction was confirmed by Southern blot.

The following strains were used:
SPO11/SPO11 pEMP46::NatMX/0 tGAL2::KanMX/0 (ANT2527),
spo11/spo11 pEMP46::NatMX/0 tGAL2::KanMX/0 SpCAS9*-SPO11/0 expressing the guide RNA handle, i.e., a guide RNA without the SDS region which is specific for the chromosomal target (ANT2539),
spo11/spo11 pEMP46::NatMX/0 tGAL2::KanMX/0 SpCAS9*-SPO11/0 expressing the UAS-D/E guide RNA (sgRNA$_{UAS-D/E}$) (ANT2540),
spo11/spo11 pEMP46::NatMX/0 tGAL2::KanMX/0 SpCAS9*-SPO11/0 expressing in multiplex the UAS-A guide RNA (sgRNA$_{UAS-A}$), the UAS-B guide RNA (sgRNA$_{UAS-B}$) and the UAS-D/E guide RNA (sgRNA$_{UAS-D/E}$) (MultigRNAs) (ANT2557).

After sporulation, the tetrads composed of 4 spores were dissected and the spores genotyped after germination for nourseothricin and hygromycin segregation. The number of tetrads showing a parental ditype (PD) was compared with those showing a tetratype (T) and a non-parental ditype (NPD). The genetic distance in centimorgans was determined according to the formula cM=100(T+6NPD)/2(PD+T+NPD). The increase in the number of tetratypes in the cells expressing SpCAS9*-SPO11 (strains ANT2540 and ANT2557) was tested statistically with Fisher's test by calculating the p-value with respect to the cells co-expressing SpCAS9*-SPO11 and the guide RNA handle (strain ANT2539).

The results presented in FIG. 11B show that the expression of the SpCas9*-SPO11 construction (dCAS9-SPO11) stimulates meiotic recombination in the GAL2 target region.

12. Targeting of Meiotic DNA Double-Strand Breaks by the SpCas9*-Spo11 Fusion Protein and a Guide RNA Specific for the Sequence Encoding the PUT4 Gene The SpCAS9*-Spo11 expression cassette (dCAS9-SPO11) was integrated into the chromosomal TRP1 locus (chromosome IV). The PUT4 guide RNA (sgRNA$_{PUT4}$) (SEQ ID NO: 16) was expressed by the multicopy replicative (non-integrative) plasmid as described above (FIG. 2A). The fusion gene carrying the SpCAS9*-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the SpCAS9*-SPO11 construction was confirmed by Southern blot.

The following strains were used:
SPO11/SPO11 (ORD7304),
spo11/spo11 SpCAS9*-SPO11/0 expressing the guide RNA handle, i.e., a guide RNA without the SDS region which is specific for the chromosomal target (ANT2527),
spo11/spo11 SpCAS9*-SPO11/0 expressing the PUT4 guide RNA (sgRNA$_{PUT4}$) (ANT2547).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after digestion of genomic DNA by the restriction enzymes BamHI and XhoI. The DNA was probed with a fragment internal to the CIN1 locus. The bands were quantified using the ImageJ software.

Figure 12:
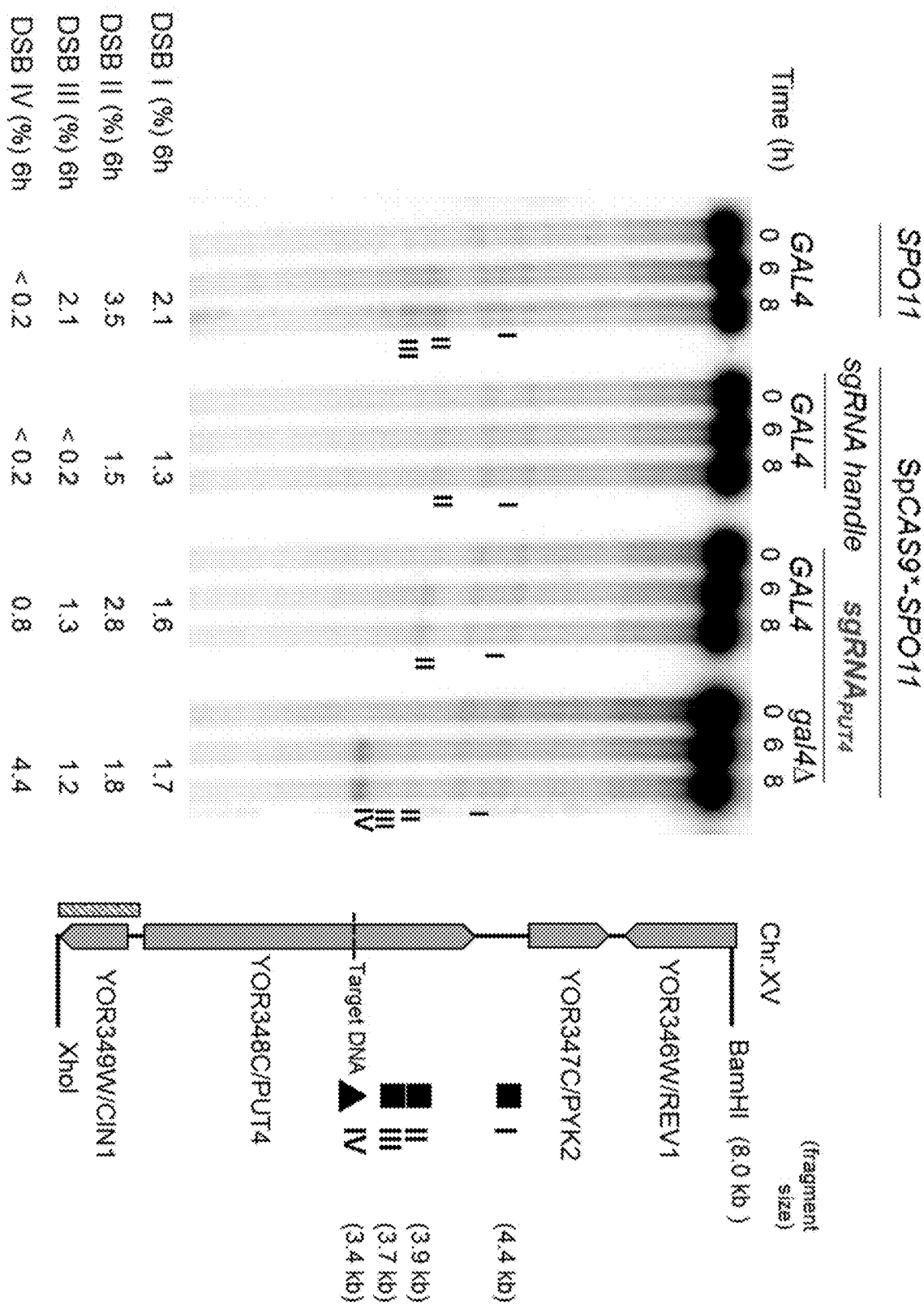
FIG. 12: Targeting of meiotic DSBs by the SpCas9*-Spo11 protein and a guide RNA specific for the PUT4 gene coding sequence. On the right of the gel, a chart indicates the position of the genes (coding regions, gray arrows) and the position of the probe (hatched rectangle). The percentage of DSBs corresponds to the ratio between the signal intensity of the fragment concerned and the total signal of the lane.

The results presented in FIG. 12 show that the expression of the SpCAS9*-SPO11 construction (dCas9-SPO11) induces meiotic DNA double-strand breaks (DSBs) at the natural cleavage sites of the Spo11 protein (PYK2-PUT4 region) of chromosome XV (DSBs I, II, III and V symbolized by black squares in FIG. 11) and at the target site (DSBs IV symbolized by a black triangle) by the PUT4 guide RNA (sgRNA$_{PUT4}$) and located in the coding region of the PUT4 gene.

13. Conclusion

The results presented in FIGS. 5 to 12 show that:
the expression of the SpCas9*-Spo11 fusion protein (dCAS9-SPO11) complements the inviability of spores derived from sporulation of SPO11 gene-inactivated strains,
the expression of the SpCas9*-Spo11 fusion protein (dCAS9-SPO11) induces the formation of meiotic double-strand breaks at natural DSB sites,
the co-expression of the SpCas9*-Spo11 fusion protein (dCAS9-SPO11) and a gRNA induces the formation of meiotic double-strand breaks at natural DSB sites and at the target site,
the co-expression of the SpCas9*-Spo11 fusion protein (dCAS9-SPO11) and multiplexed gRNA induces the formation of meiotic double-strand breaks (DSBs) at the various target sites, and
the targeting is effective in the strains having the wild-type SPO11 and the mutated spo11 genetic background.

Figure 14:
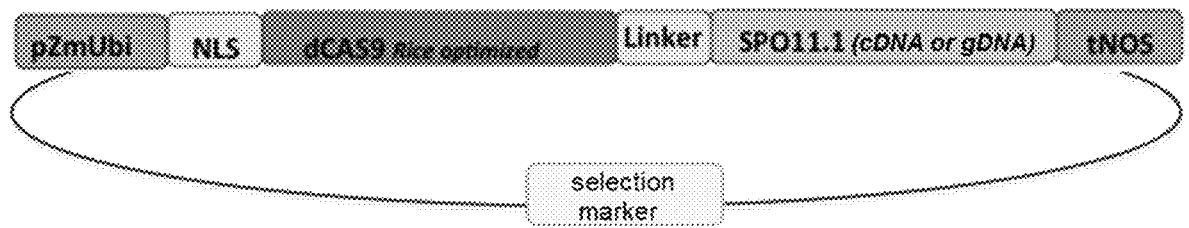
FIG. 14: Diagram of the construction for expressing the dCas9-Spo11 fusion protein in rice. pZmUbi and tNOS correspond, respectively, to the promoter and the terminator used in this construction.

14. Induction of Meiotic Double-Strand Breaks by the SpCas9*-Spo11 Fusion Protein in Rice a) Preparation of the dCas9-SPO11 Transformation Vector (See FIG. 14)

Cas9 being a protein of prokaryotic origin, the codons used are optimized for the plant species in which the protein is to be expressed. The codons of the Cas9 protein from *Streptococcus pyogenes* are thus optimized for its expression in rice (see Miao et al., Cell Research, 2013, pp. 1-4). Furthermore, the Cas9 protein is inactivated by mutation of two catalytic sites, RuvC and HNH (Asp$^{10}$→Ala$^{10}$ and His$^{840}$→Ala$^{840}$). The catalytically inactive form of SpCas9 is called SpCas9* or dCas9.

First, the dCas9 stop codon is removed and a linker is added in phase at the C-terminal end of dCas9. The linker may be a sequence already known in the literature for use in the plant species concerned or an optimized sequence. The linker CCGGAATTTATGGCCATGGAGGCCCCGGG-GATCCGT (SEQ ID NO: 17) used in yeast is also compatible with use in rice.

A nuclear localization signal (NLS) is also added at the N-terminal end of dCas9. Optionally, a linker may be added between the NLS and dCas9, such as for example the sequence GGTATTCATGGAGTTCCTGCTGCG (SEQ ID NO: 18).

The SPO11 sequence is then added in phase at the C-terminal end of the NLS-dCas9-Linker construction. It is possible to use a sequence of complementary DNA (cDNA), of genomic DNA (gDNA) or a complementary DNA sequence with addition of several introns. It is possible to use rice SPO11-1 and/or SPO11-2.

The nopaline synthase terminator (tNOS), adapted to rice, is added in phase to the NLS-dCas9-Linker-SPO11 construction.

The maize ubiquitin promoter pZmUbi1 (Christensen A H et al., 1992, Plant Mol Biol, 18(4), pp. 675-689 or Christensen A H and Quail P H, 1995, Transgenic Res, 5(3), pp. 213-218), is a promoter allowing ubiquitous and strong expression in rice.

For stable transformation of rice cells, the transfection is carried out with a binary vector, for example the binary vector pCAMBIA5300 carrying a hygromycin-resistance gene interrupted by an intron of the catalase gene. This resistance gene makes it possible to effectively select, on a selective medium, the individuals having integrated dCas9-SPO11 into their genome. This vector also contains a kanamycin-resistance gene, which facilitates cloning and engineering in bacterial hosts.

b) Preparation of the Construct Carrying the Guide RNA

With regard to the "handle" region of the guide RNA (gRNA), the "native" sequence of the *bacterium S. pyogenes* is used. The SDS region determining the specificity of the gRNA is selected as a function of the zone of interest to be targeted using software freely available on the Internet (for example CRISPR PLANT).

The guide RNA is placed under the control of the rice polymerase III U3 promoter (see Miao et al. Cell Research, 2013, pp. 1-4). Alternatively, it is placed under the control of the U6 promoter.

Single Binary Vector

The construction comprising the guide RNA placed under the control of the U3 promoter is integrated into the vector comprising dCAS9-SPO11.

Separate Binary Vectors

In order to target several regions, the guide RNAs are carried by a separate vector, a binary vector carrying a resistance to geneticin (pCAMBIA2300), which makes it possible to apply a dual selection for the presence of the dCas9-SPO11 T-DNA and the gRNA T-DNA.

Several transformation strategies are possible:
Co-transformation: Starting with two binary vectors, one carrying dCas9-SPO11 and the other the gRNA(s). They are introduced into the same bacterial strain or two different bacterial strains which are then mixed before co-culture with the plant cells.
Sequential transformations: Stable transformants carrying the dCas9-SPO11 construct are produced and their seeds used to produce calli which are then used for transformation with the gRNA construct by *Agrobacterium* or by bombardment.
Independent transformations: Plants carrying dCAS9-SPO11 without a guide and plants carrying gRNAs alone are generated. The stable transformants are then crossed so as produce multiple combinations.

c. Transformation of Rice

The transformation of rice is carried out from calli of mature seed embryos according to the protocol detailed in Sallaud C et al., 2003, Theor Appl Genet, 106(8), pp. 1396-1408.

Use of the dCas9-SPO11 Technology to Induce a Targeted Recombination in Wild-Type SPO11

The dCas9-SPO11 fusion protein is produced with the native SPO11 protein (SPO11-1 or SPO11-2), as gDNA or cDNA.

by direct transformation of calli derived from F1 seeds: calli are induced from mature F1 seed embryos obtained by castration and manual fertilization between two parental lines of agronomic interest. The calli are transformed simultaneously with the T-DNA or T-DNAs carrying dCas9-SPO11 and the gRNA(s) (co-transformation). Transformants without gRNA or with a gRNA targeting another region are used as controls to test the efficacy of the system. The recombination analysis is carried out on the F2 plants.

by separate transformation of calli of each parent: a line is transformed stably and homozygously with the dCas9-SPO11 construct and crossed with the other line carrying the gRNA(s) with heterozygous insertion. The F1 plants carrying both constructs or only the dCas9 SPO11 construct are selected. The recombinations at the target locus (loci) are quantified in the F2 populations derived from the two types of plants.

Use of the dCAS-9-SPO11 Technology to Induce a Targeted Recombination in Mutant Spo11

One of the parental lines (seeds carried by a SPO11/spo11 heterozygote) is transformed with the dCas9-SPO11 construct and plants homozygous for the transgene and the spo11 mutation are obtained in T1 generation. The second parental line (seeds carried by a SPO11/spo11 heterozygote) is transformed with the construct carrying the gRNA(s). Plants heterozygous for the gRNA construct and the spo11 mutation are obtained in T1 generation. The two types of plants are crossed: 4 genotypes of F1 seeds are obtained, all carrying the dCas9-SPO11 construct but carrying or not carrying the gRNA and producing or not producing endogenous SPO11. The recombination analysis is carried out on the F2 populations.

The invention claimed is:

1. A method for inducing targeted meiotic recombinations in a yeast cell comprising:
introducing into a yeast cell:
a) a fusion protein comprising a Cas9 protein lacking nuclease activity and a Spo11 protein, or a nucleic acid encoding said fusion protein; and
b) one or more guide RNAs or one or more nucleic acids encoding said guide RNAs, said guide RNAs comprising an RNA structure for binding to the Cas9 protein of the fusion protein and a sequence complementary to a targeted chromosomal region; and
inducing said cell to enter meiotic prophase I
thereby inducing meiotic recombination(s) at the targeted chromosomal region.

2. The method according to claim 1, wherein the fusion protein further comprises a nuclear localization signal sequence.

3. The method according to claim 1, wherein the nucleic acid encoding said fusion protein is operably linked to a constitutive, inducible or meiosis-specific promoter.

4. The method according to claim 1, further comprising introducing one or more additional guide RNAs targeting one or more other chromosomal regions, or nucleic acids encoding said additional guide RNAs.

5. A method for generating variants of a non-human eukaryotic organism comprising introducing into a cell of said non-human eukaryotic organism:
a) a fusion protein comprising a Cas9 protein lacking nuclease activity and a Spo11 protein, or a nucleic acid encoding said fusion protein; and
b) one or more guide RNAs, or one or more nucleic acids encoding said guide RNAs, said guide RNAs comprising an RNA structure for binding to the Cas9 protein and a sequence complementary to a targeted chromosomal region;
inducing said cell to enter meiotic prophase I;
obtaining a cell or cells having recombination(s) at the targeted chromosomal region(s); and
generating a variant of the organism from said recombinant cell,
wherein the non-human eukaryotic organism is a yeast or a plant.

6. A method for identifying or locating genetic information encoding a characteristic of interest in a eukaryotic cell genome comprising:
introducing into the eukaryotic cell:
a) a fusion protein comprising a Cas9 protein lacking nuclease activity and a Spo11 protein, or a nucleic acid encoding said fusion protein; and
b) one or more guide RNAs, or one or more nucleic acids encoding said guide RNAs, said guide RNAs comprising an RNA structure for binding to the Cas9 protein and a sequence complementary to a targeted chromosomal region;
inducing said cell to enter meiotic prophase I;
obtaining a cell or cells having recombination(s) at the targeted chromosomal region(s); and
analyzing genotypes and phenotypes of the recombinant cells in order to identify or to locate the genetic information encoding the characteristic of interest,
wherein the eukaryotic cell is a yeast or a plant cell.

7. The method according to claim 6, wherein the characteristic of interest is a quantitative trait of interest (QTL).

* * * * *

UNITED STATES PATENT AND TRADEMARK OFFICE
CERTIFICATE OF CORRECTION

PATENT NO. : 11,248,240 B2
APPLICATION NO. : 15/547084
DATED : February 15, 2022
INVENTOR(S) : Giacomo Bastianelli, Alexandre Serero and Alain Nicolas It is certified that error appears in the above-identified patent and that said Letters Patent is hereby corrected as shown below:

In the Specification

Column 11,
Line 21, "Etag," should read --E-tag,--.
Line 21, "Stag," should read --S-tag,--.
Lines 60-61, "C and/or" should read --C- and/or--.

Column 12,
Line 10, "6N-methylysine," should read --6-N-methylysine,--.
Line 11, "alloisoleucine," should read --allo-isoleucine,--.
Line 14, "cyclohexylalanine." should read --cyclohexyl-alanine.--.
Lines 33-34, "basepair interactions between the transactivating" should read --base-pair interactions between the trans-activating--.
Line 36, "stemloop" should read --stem-loop--.
Line 45, "82 nucleotide" should read --82-nucleotide--.

Column 13,
Line 31, "H phosphonates" should read --H-phosphonates--.
Line 32, "alkylphosphonates," should read --alkyl-phosphonates,--.

Column 19,
Line 35, "nonembryonic." should read --non-embryonic.--.

Column 20,
Line 27, "nonlimiting" should read --non-limiting--.

Column 21,
Line 5, "2 micron (4)" should read --2-micron (2μ)--.

Signed and Sealed this
Eighth Day of November, 2022

Katherine Kelly Vidal
*Director of the United States Patent and Trademark Office*

Column 24,
Line 63, "SPOT locus." should read --*SPO7* locus.--.

In the Claims

Column 86,
Lines 9-10, "is a yeast or a plant." should read --is a yeast.--.
Line 29, "is a yeast or a plant cell." should read --is a yeast cell.--.